(12) United States Patent
Sato et al.

(10) Patent No.: US 7,914,905 B2
(45) Date of Patent: Mar. 29, 2011

(54) π-CONJUGATED AROMATIC RING-CONTAINING COMPOUND AND ORGANIC ELECTROLUMINESCENT DEVICE

(75) Inventors: Fumie Sato, Fujisawa (JP); Yuuki Takayama, Funabashi (JP)

(73) Assignees: Fumie Sato, Fujisawa-Shi (JP); Nissan Chemical Industries, Ltd., Tokyo (JP)

( * ) Notice: Subject to any disclaimer, the term of this patent is extended or adjusted under 35 U.S.C. 154(b) by 968 days.

(21) Appl. No.: 10/591,950

(22) PCT Filed: Mar. 8, 2005

(86) PCT No.: PCT/JP2005/003950
§ 371 (c)(1),
(2), (4) Date: Mar. 7, 2007

(87) PCT Pub. No.: WO2005/085176
PCT Pub. Date: Sep. 15, 2005

(65) Prior Publication Data
US 2007/0176164 A1  Aug. 2, 2007

(30) Foreign Application Priority Data
Mar. 9, 2004 (JP) ................. 2004-065446

(51) Int. Cl.
C09K 11/06 (2006.01)
H01L 51/54 (2006.01)

(52) U.S. Cl. ... 428/690; 428/917; 313/504; 252/301.16; 564/433; 556/413; 556/431; 546/286

(58) Field of Classification Search ............. None
See application file for complete search history.

(56) References Cited

U.S. PATENT DOCUMENTS
3,530,325 A  9/1970  Mehl et al.

FOREIGN PATENT DOCUMENTS
EP  1 067 165 A2  1/2001
JP  59-194393 A  11/1984
JP  3-152897 A  6/1991

OTHER PUBLICATIONS

Edelmann et al. Chimica 2001, 55, 132-138. Date of publication: Mar. 2001.*
Kaafarani et al. J. Org. Chem. 2003, 68, 5377-5380. Date of publication: Jun. 3, 2003.*
Hwang et al. J. Am. Chem. Soc. 2003, 125, 11241-11248. Date of publication: Aug. 20, 2003.*
Utesch et al. Org. Biomol. Chem. 2003, 1, 237-239. Date of publication: Dec. 9, 2002.*
Wan et al. Eur. J. Org. Chem. 2001, 3485-3490. Date of publication: Aug. 12, 2001.*
Giesa et al. Polymer International 1994 33, 43-60. Date of publication: Jan. 2004.*
Bestmann et al., Liebigs Annalen der chemie, 1980, (12), pp. 2061-2071.
Fomina, et al., Polymer, 1996, 37(9), pp. 1723-1728.
Takayama et al., Organic Letters, 2004, 6(23), pp. 4253-4256.
Nakano et al., Organic Letters, 2004, 6(14), pp. 2373-2376.
"Japanese Journal of Applied Physics" vol. 27, No. 2, pp. L269-L271, Japan Society of Applied Physics Corporation Aggregate of Japan (1988).

* cited by examiner

Primary Examiner — D. Lawrence Tarazano
Assistant Examiner — Andrew K Bohaty
(74) Attorney, Agent, or Firm — Birch, Stewart, Kolasch & Birch, LLP

(57) ABSTRACT

A π-conjugated aromatic ring-containing compound represented by the formula (1) below is relatively stable and useful as a light-emitting material for light from blue-violet region to red region.

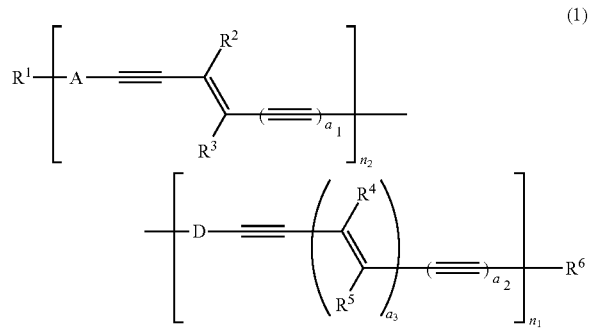

[In the formula, $R^1$-$R^6$ independently represent a hydrogen atom or the like; A and D independently represent a pyridine ring, pyrimidine ring, pyridazine ring, pyrazine ring, furan ring, pyrrole ring, pyrazole ring, imidazole ring, thiophene ring, benzothiadiazole ring, thieno[3,4-b]pyrazine ring, furo[3,4-b]pyrazine ring, 6H-pyrrolo[3,4-b]pyrazine ring or the like; $a_1$, $a_2$ and $a_3$ independently represent 0 or 1; and $n_1$ and $n_2$ independently represent an integer of 1-5.]

15 Claims, 4 Drawing Sheets

US 7,914,905 B2

π-CONJUGATED AROMATIC RING-CONTAINING COMPOUND AND ORGANIC ELECTROLUMINESCENT DEVICE

This Nonprovisional application is the national phase of PCT International Application No. PCT/JP2005/003950, filed Mar. 8, 2005, which claims priority under 35 U.S.C. §119(a) on Patent Application No(s). JP 2004-065446 filed in Japan on Mar. 9, 2004, the entire contents of each application being hereby incorporated by reference.

TECHNICAL FIELD

This invention relates to a π-conjugated aromatic ring-containing compound and more particularly, to a π-conjugated aromatic ring-containing compound that can be favorably used as a light-emitting material, for example, for organic electroluminescent device.

BACKGROUND ART

Conventionally, inorganic electroluminescent devices have been in use as a planar light source. Because an alternating high voltage is needed for driving the device and blue light emission is difficult, a difficulty has been involved in full colorization based on the three prime colors of RGB.

On the other hand, electroluminescent devices using organic materials have been extensively investigated up to now. For instance, reports have been made on the use of single crystal anthracene or the like as a fluorescent organic compound (Patent Document 1: U.S. Pat. No. 3,530,325 specification), a combination of a hole transport layer and an emission layer (Patent Document 2: JP-A 59-194393), a combination of a hole transport layer, an emission layer and an electron transport layer (Non-Patent Document 1: Japanese Journal of Applied Physics), and the like.

Organic electroluminescent devices should meet requirements for energy conversion efficiency, luminous efficiency and stability of light-emitting materials. The above-mentioned organic electroluminescent devices are not satisfactory with respect to these characteristic properties and thus, further improvements are demanded.

With a full color display, light-emitting materials for red, green and blue constituting the three prime colors are necessary, with the attendant problem on color purities thereof. It is known that currently known organic electroluminescent devices are not satisfactory with respect to the red light emission efficiency.

To cope with this deficiency, there has been developed an organic electroluminescent device wherein blue or bluish green light emission from an organic light-emitting material is subjected to color conversion with a fluorescent dye to emit red light (Patent Document 4: JP-A 3-152897).

In the technique of this Patent Document 4, a difficulty is involved in that because blue or bluish green light generated from an organic light-emitting material is absorbed and only a little number of dyes having a red fluorescence is known, blue to red color conversion is carried out by one step. In the technique of the Patent Document 4, although a stepwise technique using a plurality of dyes is adopted, this technique has a problem in that the emission efficiency of device lowers.

Further, taking these techniques into account, there has been developed an organic electroluminescent device wherein an organic light-emitting material capable of generating light in a bluish violet region and a fluorescent dye absorbing light in the bluish violet region (Patent Document 5: EP-A 1067165).

In the technique of this patent document 5, because a dye having absorption of light in a bluish violet region and also having a red fluorescence is used, conversion to red is possible by one step and its efficiency can be improved over the case using the two-step conversion. However, this method makes use of conversion of bluish violet into red and thus, a lowering of emission efficiency is not avoidable. In addition, when using conventional organic light-emitting materials, an emission intensity after conversion into red is not always satisfactory.

For organic light-emitting materials of organic electroluminescent devices, stable light-emitting materials having excellent charge transportability have been demanded.

[Patent Document 1]
U.S. Pat. No. 3,530,325 specification
[Patent Document 2]
JP-A 59-194393
[Patent Document 3]
JP-A 63-295695
[Patent Document 4]
JP-A 3-152897
[Patent Document 5]
EP-A 1067165
[Non-Patent Document 1]
"Japanese Journal of Applied Physics (Jpn. J. Appl. Phys.)", Japan Society of Applied Physics, Corporation Aggregate of Japan, 1988 Vol. 27, pp. L269-L271

DISCLOSURE OF THE INVENTION

Problems to be Solved by the Invention

Under these circumstances, the invention has for its object the provision of a π-conjugated aromatic ring-containing compound that is useful as a light-emitting material for emission in bluish violet to red regions and is relatively stable and also of an electroluminescent device provided with an organic thin layer constituted to contain the compound.

Means for Solving the Problems

In order to achieve the above object, we made intensive studies and, as a result, found that a π-conjugated aromatic ring-containing compound having an enyne π-conjugated chain, preferably an enediyne π-conjugated chain, and an aromatic ring moiety has a relatively high fluorescence intensity in a bluish violet region, may serve as a red light-emitting material depending on the type of heteroaromatic ring, and can serve as a stable light-emitting material having excellent charge transportability, and that the compound is suited for a light-emitting material for organic electroluminescent device.

More particularly, the invention provides:

1. A π-conjugated aromatic ring-containing compound, characterized by being represented by the formula (1),

[Chemical Formula 1]

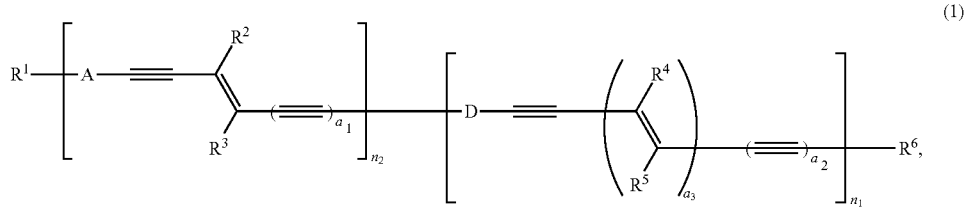

{wherein $R^1$ represents a hydrogen atom, a halogen atom, a cyano group, a nitro group, a dimethylamino group, a diphenylamino group, an alkoxy group having 1 to 3 carbon atoms, an alkyl group having 1 to 10 carbon atoms, a halogenated alkyl group that has 1 to 10 carbon atoms and may be optionally substituted with a fluorine atom or chlorine atom, or a group represented by the following formula (2) or a group represented by the following formula (3),

[Chemical Formula 2]

$$E\!-\!\!=\!\!-\!\!-\quad (2)$$

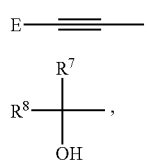

[wherein E represents a hydrogen atom, a substituted silyl group, a phenyl group, a naphthyl group, a pyridyl group, a pyrimidinyl group, a pyridazinyl group, a pyrazinyl group, a furanyl group, a pyrrolyl group, a pyrazolyl group, an imidazolyl group, a thienyl group (provided that the phenyl group, naphthyl group, pyridyl group, pyrimidinyl group, pyridazinyl group, pyrazinyl group, furanyl group, pyrrolyl group, pyrazolyl group, imidazolyl group or thienyl group may be optionally substituted with a halogen atom, a cyano group, a pyridyl group, pyrimidinyl group, pyridazinyl group, pyrazinyl group, furanyl group, pyrrolyl group, pyrazolyl group, imidazolyl group or thienyl group may be optionally substituted with a halogen atom, a cyano group, a nitro group, a dimethylamino group, a diphenylamino group, an alkoxy group having 1 to 3 carbon atoms, an alkyl group having 1 to 10 carbon atoms, or a halogenated alkyl group that has 1 to 10 carbon atoms and may be optionally substituted with a fluorine or chlorine atom), a group represented by the afore-indicated formula (2) or a group represented by the afore-indicated formula (3), A and D independently represent a naphthalene ring, an anthracene ring, a phenanthrene group, a phenarene ring, a fluorene ring, a triphenylene ring, a pyrene ring, a perylene ring, a pyridine ring, a pyrimidine ring, a pyridazine ring, a pyrazine ring, a furan ring, a pyrrole ring, a pyrazole ring, an imidazole ring, a thiophene ring, a benzothiadiazole ring, a thieno[3,4-b]pyrazine ring, a furo[3,4-b]pyrazine ring or a 6H-pyrrolo[3,4-b]pyrazine ring (provided that these rings may be optionally substituted with a phenyl group, a halogen atom, a cyano group, a nitro group, a dimethylamino group, a diphenylamino group, an alkoxy group having 1 to 3 carbon atoms, an alkyl group having 1 to 10 carbon atoms or a halogenated alkyl group that has 1 to 10 carbon atoms and may be optionally substituted with a fluorine atom or a chlorine atom), $a_1$, $a_2$, and $a_3$ are independently 0 or 1, and $n_1$ and $n_2$ are independently an integer of 1 to 5};

2. A π-conjugated aromatic ring-containing compound, characterized by being represented by the formula (4),

[Chemical Formula 3]

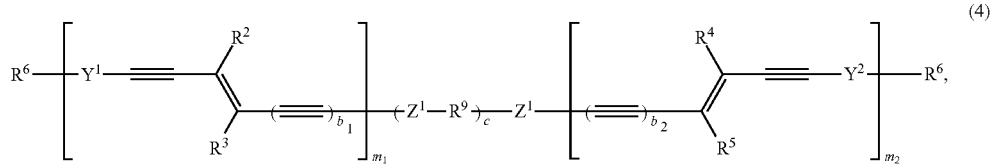

nitro group, a dimethylamino group, a diphenylamino group, an alkoxy group having 1 to 3 carbon atoms, an alkyl group having 1 to 10 carbon atoms, or a halogenated alkyl group that has 1 to 10 carbon atoms and may be optionally substituted with a fluorine or chlorine atom), $R^7$ and $R^8$ independently represent an alkyl group having 1 to 10 carbon atoms], $R^2$, $R^3$, $R^4$, and $R^5$ independently represent a hydrogen atom or an alkyl group having 1 to 10 carbon atoms, $R^6$ represents a hydrogen atom, a substituted silyl group, a phenyl group, a naphthyl group, a pyridyl group, a pyrimidinyl group, a pyridazinyl group, a pyrazinyl group, a furanyl group, a pyrrolyl group, a pyrazolyl group, an imidazolyl group, a thienyl group (provided that the phenyl group, naphthyl group,

[wherein $R^2$, $R^3$, $R^4$, $R^5$ and $R^6$, respectively, have the same meanings as defined above, $Z^1$, $Y^1$, and $Y^2$ independently represent a benzene ring, a naphthalene ring, an anthracene ring, a phenanthrene group, a phenarene ring, a fluorene ring, a triphenylene ring, a pyrene ring, a perylene ring, a pyridine ring, a pyrimidine ring, a pyridazine ring, a pyrazine ring, a furan ring, a pyrrole ring, a pyrazole ring, an imidazole ring, a thiophene ring, a benzothiadiazole ring, a thieno[3,4-b] pyrazine ring, a furo[3,4-b]pyrazine ring or a 6H-pyrrolo[3,4-b]pyrazine ring (provided that these rings may be optionally substituted with a phenyl group, a halogen atom, a cyano group, a nitro group, a dimethylamino group, a diphenylamino group, an alkoxy group having 1 to 3 carbon atoms, an alkyl group having 1 to 10 carbon atoms or a halogenated alkyl group that has 1 to 10 carbon atoms and may be optionally substituted with a fluorine atom or a chlorine atom), $R^9$ represents a single bond, —O—, —S—, —S(O)—, —S(O$_2$)—, —C(O)O—, —OC(O)—, —C(S)O—, —OC(S)—, —C(O)NH—, —NHC(O)—, —C(S)NH—, —NHC(S)—, —NH— or a divalent saturated or unsaturated hydrocarbon group that has 1-8 carbon atoms and may be branched, $b_1$ and $b_2$ are independently 0 or 1, c is an integer of 0 to 3, and $m_1$ and $m_2$ are independently an integer of 1 to 5];

3. A π-conjugated aromatic ring-containing compound, characterized by being represented by the formula (5),

[Chemical Formula 4]

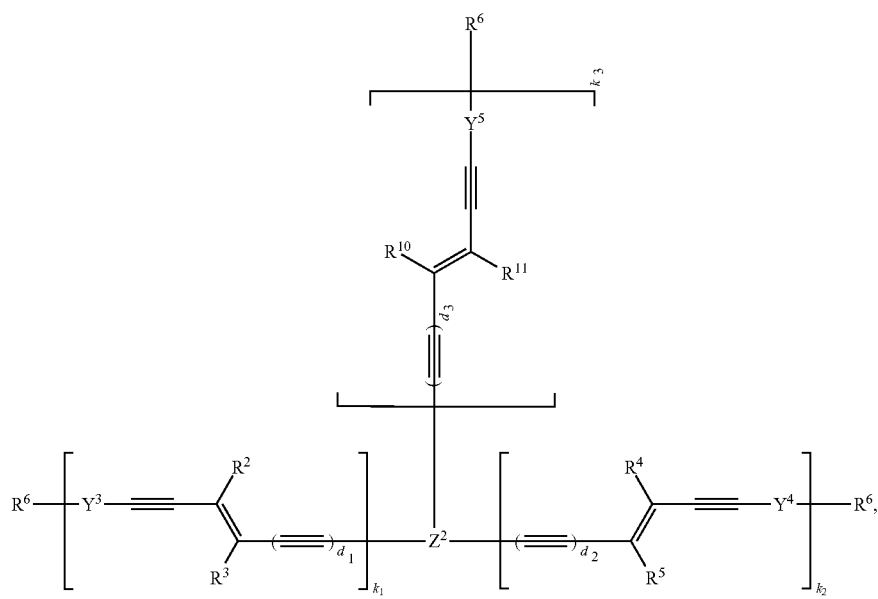

(5)

{wherein $R^2$, $R^3$, $R^4$, $R^5$ and $R^6$, respectively, have the same meanings as defined above, $R^{10}$ and $R^{11}$ independently represent a hydrogen atom or an alkyl group having 1 to 10 carbon atoms, $Y^3$ to $Y^5$ independently represent a benzene ring, a naphthalene ring, an anthracene ring, a phenanthrene group, a phenarene ring, a fluorene ring, a triphenylene ring, a pyrene ring, a perylene ring, a pyridine ring, a pyrimidine ring, a pyridazine ring, a pyrazine ring, a furan ring, a pyrrole ring, a pyrazole ring, an imidazole ring, a thiophene ring, a benzothiadiazole ring, a thieno[3,4-b]pyrazine ring, a furo[3,4-b]pyrazine ring or a 6H-pyrrolo[3,4-b]pyrazine ring (provided that these rings may be optionally substituted with a phenyl group, a halogen atom, a cyano group, a nitro group, a dimethylamino group, a diphenylamino group, an alkoxy group having 1 to 3 carbon atoms, an alkyl group having 1 to 10 carbon atoms or a halogenated alkyl group that has 1 to 10 carbon atoms and may be optionally substituted with a fluorine atom or a chlorine atom), $Z^2$ represents a trivalent aryl group, a group represented by the following formula (6) or a group represented by the following formula (7),

[Chemical Formula 5]

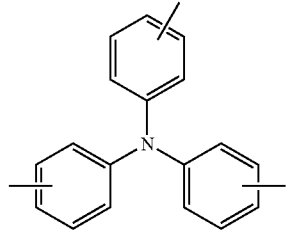

(6)

-continued

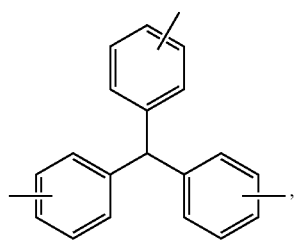

(7)

$d_1$ to $d_3$ are independently 0 or 1, and $k_1$ to $k_3$ are independently an integer of 1 to 5};

4. The π-conjugated aromatic ring-containing compound of 1 above, characterized in that said $R^1$ is a hydrogen atom, a cyano group, a nitro group, a dimethylamino group, a diphenylamino group, a methoxy group, a propoxy group, a methyl group, a trifluoromethyl group, a group represented by the following formula (8) or a group represented by the following formula (9),

[Chemical Formula 6]

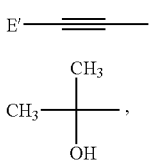

(8)
(9)

[wherein E' represents a hydrogen atom, a trimethylsilyl group, a tri-1-propylsilyl group, a phenyl group, a pyridyl group, a thienyl group (provided that the phenyl group, pyrdyl group or thienyl group may be optionally substituted with a cyano group, a nitro group, a dimethylamino group, a diphenylamino group, a methoxy group, an n-propoxy group, a methyl group or a trifluoromethyl group)];

5. The π-conjugated aromatic ring-containing compound of any one of 1-4, characterized in that said $R^2$, $R^3$, $R^4$, and $R^5$ independently represent a hydrogen atom, a methyl group, an ethyl group or an n-propyl group;

6. The π-conjugated aromatic ring-containing compound of any one of 1-5, characterized in that said $R^6$ is a hydrogen atom, a trimethylsilyl group, a tri-i-propylsilyl group, a phenyl group, a pyridyl group, a thienyl group (provided that said phenyl group, pyridyl group or thienyl group may be optionally substituted with a cyano group, a nitro group, a dimethylamino group, a diphenylamino group, a methoxy group, an n-propoxy group, a methyl group or a trifluoromethyl group), a group represented by the following formula (8) or a group represented by the following formula (9),

[Chemical Formula 7]

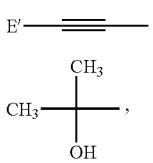

(8)
(9)

(wherein E' has the same meaning as defined before);

7. The π-conjugated aromatic ring-containing compound of 1, characterized in that said A and D independently represent a pyridine ring, a pyrimidine ring, a pyridazine ring, a pyrazine ring, a furan ring, a pyrrole ring, a pyrazole ring, an imidazole ring, a thiophene ring, a benzothiadiazole ring, a thieno[3,4-b]pyrazine ring, a furo[3,4-b]pyrazine ring or a 6H-pyrrolo[3,4-b]pyrazine ring (provided that these rings may be optionally substituted with a phenyl group, a halogen atom, a cyano group, a nitro group, a dimethylamino group, a diphenylamino group, an alkoxy group having 1 to 3 carbon atoms, an alkyl group having 1 to 10 carbon atoms or a halogenated alkyl group that has 1 to 10 carbon atoms and may be optionally substituted with a fluorine atom or a chlorine atom);

8. The π-conjugated aromatic ring-containing compound of 7, characterized in that said A and D independently represent a pyridine ring, a pyridazine ring, a thiophene ring, a benzothiadiazole ring or a thieno[3,4-b]pyrazine ring (provided that these rings may be optionally substituted with a phenyl group, a cyano group, a methoxy group, an n-propoxy group, a methyl group or a trifluoromethyl group);

9. The π-conjugated aromatic ring-containing compound of 2, 5, or 6, characterized in that said $Z^1$, $Y^1$, and $Y^2$ independently represent a benzene ring, a naphthalene ring, an anthracene ring, a pyridine ring, a pyridazine ring, a thiophene ring, a pyrrole ring, a benzothiadiazole ring or a thieno[3,4-b]pyrazine ring (provided that these rings may be optionally substituted with a phenyl group, a cyano group, a methoxy group, an n-propoxy group, a methyl group or a trifluoromethyl group), and $R^9$ represents a single bond or —O—, $b_1$ and $b_2$ are both 1, and c is 0 or 1;

10. The π-conjugated aromatic ring-containing compound of 3, 5, or 6, characterized in that said $Y^3$ to $Y^5$ independently represent a phenylene ring, a naphthalene ring, an anthracene ring, a pyridine ring, a pyridazine ring, a thiophene ring, a pyrrole ring, a benzothiadiazole ring or a thieno[3,4-b]pyrazine ring (provided that these rings may be optionally substituted with a phenyl group, a cyano group, a methoxy group, an n-propoxy group, a methyl group or a trifluoromethyl group), $Z^2$ is a group represented by the following formula (10) or a group represented by the following formula (11), and $d_1$ to $d_3$ are all 1,

[Chemical Formula 8]

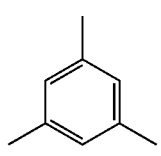

(10)

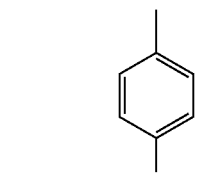

(11)

; and

11. An organic electroluminescent device of the type which includes an anode and a cathode, and an organic thin film layer interposed their between, characterized in that said organic thin film layer is a layer constituted to contain the π-conjugated aromatic ring-containing compound of 1-10.

EFFECTS OF THE INVENTION

The π-conjugated aromatic ring-containing compound of the invention has such an enyne, (enediyne) chain structure as shown in (1), (4), or (5) above, and is relatively excellent in stability because it is not a metal complex. Where a heteroaromatic ring site is included, the compound has a relatively high fluorescent intensity in a bluish violet region and also has a red fluorescence, which is conventionally difficult to achieve with a single organic material, depending on the kind of heteroaromatic ring. Especially, the compound represented by the formula (5) has such a structure that conjugated systems extend in three directions and thus, has excellent charge transportability.

For these reasons, the π-conjugated aromatic ring-containing compound of the invention can be conveniently used as a light-emitting material for organic electroluminescent device. The organic electroluminescent device using the π-conjugated aromatic ring-containing compound can be favorably used as a planar light source for use as a backlight, a light emitting source, an illumination device, display devices such as a flat panel display, and the like.

BEST MODE FOR CARRYING OUT THE INVENTION

Figure 1:
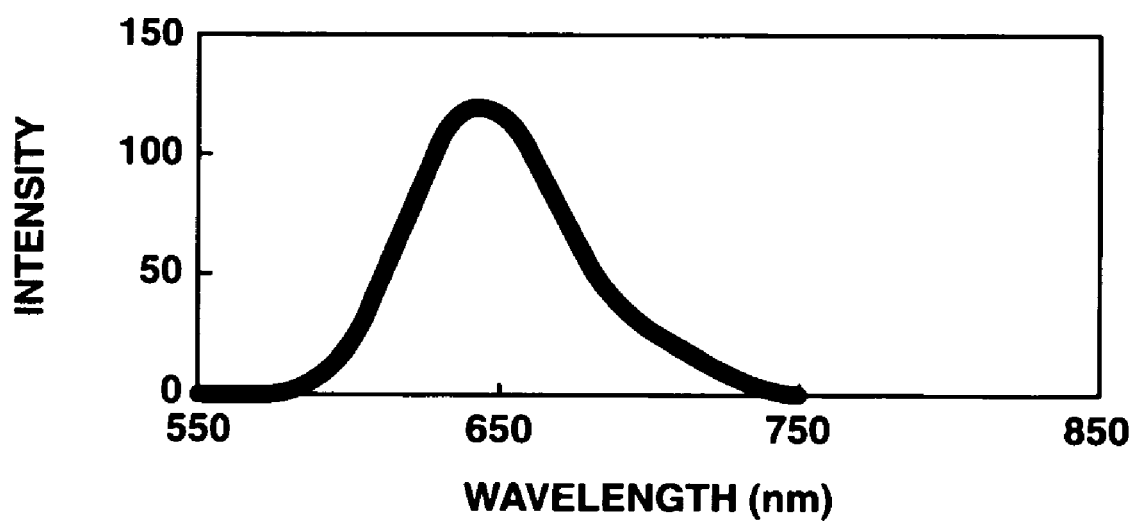
FIG. 1 is a fluorescent spectrum of compound 36.

The invention is now described in more detail.
The π-conjugated aromatic ring-containing compound of the invention is characterized by being represented by the above-indicated formula (1), (4), or (5).
In the formula (1), (4), or (5), for the halogen atom, mention is made of a fluorine atom, a chlorine atom, a bromine atom or an iodine atom.
For the alkoxy group having 1 to 3 carbon atoms, mention is made of a methoxy group, an ethoxy group, a propoxy group, or an isopropoxy group.
For the alkyl group having 1 to 10 carbon atoms, the group may be linear, branched or cyclic and includes, for example, a methyl, ethyl, n-propyl, i-propyl, n-butyl, i-butyl, s-butyl, t-butyl, n-pentyl, i-amyl, t-amyl, neo-pentyl, n-hexyl, heptyl, octyl, nonyl or decyl group, or the like.
For the halogenated alkyl group that has 1 to 10 carbon atoms and may be optionally substituted with a fluorine atom or chlorine atom, mention is made of a trifluoromethyl, 2,2,2-trifluoroethyl, 1,1,2,2,2-pentafluoroethyl, 2,2,3,3,3-pentafluoropropyl group, or the like.
For the substituted silyl group, mention is made of trimethylsilyl, triethylsilyl, tri-n-propylsilyl, tri-i-propylsilyl, tri-n-butylsilyl, tri-i-butylsilyl, tri-n-hexylsilyl, dimethylethylsilyl, dimethyl-n-propylsilyl, dimethyl-n-butylsilyl, dimethyl-i-butylsilyl, dimethyl-t-butylsilyl, dimethyl-n-pentylsilyl, dimethyl-n-octylsilyl, dimethylcyclohexylsilyl, dimethylhexylsilyl, dimethyl-2,3-dimethylpropylsilyl, dimethyl-2-(bicycloheptyl)silyl, dimethylbenzylsilyl, dimethylphenylsilyl, dimethyl-p-tolylsilyl, dimethylflophemethylsilyl, methyldiphenylsilyl, triphenylsilyl, diphenyl-t-butylsilyl, tribenzylsilyl, diphenylvinylsilyl, diphenyl-n-butylsilyl, phenylmethylvinylsilyl or the like.
In the formula (4), specific examples of the divalent saturated or unsaturated hydrocarbon group that has 1-8 carbon atoms and may be branched include —CH$_2$—, —CH$_2$CH$_2$—, —CH$_2$CH$_2$CH$_2$—, —CH$_2$CH$_2$CH$_2$CH$_2$—, —CHMe-, —CMe$_2$-, —CHEt—, —CEt$_2$-, —CMeEt-, —CHMeCH$_2$—, —CH$_2$CHMe-, —CMe$_2$CH$_2$—, —CH$_2$CMe$_2$-, —CHMeCHMe-, —CMe$_2$CHMe-, —CHMeCMe$_2$-, —CMe$_2$CMe$_2$-, —CHEtCH$_2$—, —CH$_2$CHEt—, —CEt$_2$CH$_2$—, —CH$_2$CEt$_2$-, —CHEtCHEt—, —CEt$_2$CHEt—, —CEt$_2$CHEt—, —CHEtCEt$_2$-, —CMeEtCH$_2$—, —CH$_2$CMeEt—, —CHMeCHEt—, —CHEtCHMe-, —CMeEtCHEt—, —CEt$_2$CHMe-, —CHMeCEt$_2$-, —CHEtCMeEt—, —CH=CH—, —CH=CHCH$_2$—, —CH$_2$CH=CH—, —CH=CHCH$_2$CH$_2$—, —CH$_2$CH=CHCH$_2$—, —CH$_2$CH$_2$CH=CH—, —CH=CHCH=CH—, —CMe=CH—, —CH=CMe-, —CMe=CMe-, —CEt=CH—, —CH=CEt-, —CMe=CEt-, —CMe=CHCH$_2$—, —CH=CMeCH$_2$—, —CH=CHCHMe-, —CMe=CMeCH$_2$—, —CMe=CHCHMe-, —CH=CMeCHMe-, —CH=CHCMe$_2$-, —CMe=CMeCHMe-, —CMe=CHCMe$_2$-, —CH=CMeCMe$_2$-, —CMe=CMeCMe$_2$-, —CH$_2$CMe=CH—, —CHMeCH=CH—, —CH$_2$CH=CMe-, —CHMeCH=CMe-, —CH$_2$CMe=CMe-, —CMe$_2$CH=CH—, —CHMeCMe=CMe-, —CMe$_2$CMe=CH—, —CMe$_2$CH=CMe-, —CMe$_2$CMe=CMe-, —CMe=CHCH=CH—, —CH=CMeCH=CH—, —CH=CHCMe=CH—, —CH=CHCH=CMe-, —CMe=CMeCH=CH—, —CMe=CHCMe=CH—, —CMe=CHCH=CMe-, —CH=CMeCH=CMe-, —CH=CMeCMe=CH—, —CH=CHCMe=CMe-, —CMe=CMeCMe=CMe-, —C≡C—, —C≡CCH$_2$—, —CH$_2$C≡C—, —C≡CCH$_2$CH$_2$—, —CH$_2$C≡CCH$_2$—, —CH$_2$CH$_2$C≡C—, —C≡CC≡C—, —C≡CCHMe-, —CHMeC≡C—, —C≡CCHEt-, —CHEtC≡C—, —C≡CCMe$_2$-, —CMe$_2$C≡C—, —C≡CCCEt$_2$-, —CEt$_2$C≡C—, —C≡CCMeEt-, —CMeEtC≡C—, and the like.

In the formula (5), specific examples of the trivalent aryl group include a trivalent benzene ring, naphthalene ring, anthracene ring, phenanthrene ring, phenarene ring, fluorine ring, triphenylene ring, pyrene ring, perylene ring, pyridine ring, primidine ring, pridazine ring, pyrazine ring, furan ring, pyrrole ring, pyrazole ring, imidazole ring, thiopehene ring, benzothiadiazole ring, thieno[3,4-b]pyrazine ring, furo[3,4-b]pyrazine ring or 6H-pyrrolo[3,4-b]ring.

In the formula (1), $R^1$ preferably includes a hydrogen atom, a cyano group, a nitro group, a dimethylamino group, a diphenylamino group, a methoxy group, a propoxy group, a methyl group, a trifluoromethyl group, a group represented by the following formula (8) or a group represented by the following formula (9).

[Chemical Formula 9]

(8)

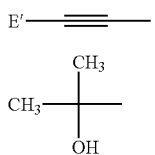

(9)

In the formula (8), E' includes a hydrogen atom, a trimethylsilyl group, a tri-i-propylsilyl group, a phenyl group, a pyridyl group, a thienyl group (provided that the phenyl group, pyridyl group or thienyl group may be optionally substituted with a cyano group, a nitro group, a dimethylamino group, a diphenylamino group, a methoxy group, an n-propoxy group, a methyl group or a trifluoromethyl group).

In the formulas (1), (4), and (5), it is preferred that $R^2$ to $R^5$ independently represent a hydrogen atom, or a methyl, ethyl or n-propyl group.

In the formulas (1), (4), and (5), $R^6$ preferably includes a hydrogen atom, a trimethylsilyl group, a tri-i-propylsilyl group, a phenyl group, a pyridyl group, a thienyl group (provided that the phenyl group, pyridyl group or thienyl group may be optionally substituted with a cyano group, a nitro group, a dimethylamino group, a diphenylamino group, a methoxy group, an n-propoxy group, a methyl group or a trifluoromethyl group), a group represented by the above formula (8) or a group represented by the formula (9).

In the formula (4), $R^9$ preferably includes a single bond or —O—.

In the formula (5), it is preferred that $R^{10}$ and $R^{11}$ independently represent a hydrogen atom, a methyl, ethyl, or n-propyl group.

In the formula (1), it is preferred that A and D include a pyridine ring, a pyrimidine ring, a pyridazine ring, a pyrazine ring, a furan ring, a pyrrole ring, a pyrazole ring, an imidazole ring, a thiophene ring, a benzothiadiazole ring, a thieno[3,4-b]pyrazine ring, a furo[3,4-b]pyrazine ring or a 6H-pyrrolo[3,4-b]pyrazine ring (provided that these rings may be optionally substituted with a phenyl group, a halogen atom, a cyano group, a nitro group, a dimethylamino group, a diphenylamino group, an alkoxy group having 1 to 3 carbon atoms, an alkyl group having 1 to 10 carbon atoms or a halogenated alkyl group that has 1 to 10 carbon atoms and may be optionally substituted with a fluorine atom or a chlorine atom), and more preferably, a pyridine ring, a pyridazine ring, a thiophene ring, a benzothiadiazole ring or a thieno[3,4-b]pyrazine ring (provided that these rings may be optionally substituted with a phenyl group, a cyano group, a methoxy group, an n-propoxy group, a methyl group or a trifluoromethyl group).

In the formula (4), $Z^1$, $Y^1$, and $Y^2$ preferably include a benzene ring, a naphthalene ring, an anthracene ring, a pyridine ring, a pyridazine ring, a thiophene ring, a pyrrole ring, a benzothiadiazole ring or a thieno[3,4-b]pyrazine ring (provided that these rings may be optionally substituted with a phenyl group, a cyano group, a methoxy group, an n-propoxy group, a methyl group or a trifluoromethyl group).

In the formula (5), $Y^3$ to $Y^5$ preferably include a phenylene ring, a naphthalene ring, an anthracene ring, a pyridine ring, a pyridazine ring, a thiophene ring, a pyrrole ring, a benzothiadiazole ring or a thieno[3,4-b]pyrazine ring (provided that these rings may be optionally substituted with a phenyl group, a cyano group, a methoxy group, an n-propoxy group, a methyl group or a trifluoromethyl group).

For $Z^2$, a group represented by the following formula (10) or a group represented by the following group (11) is preferred.

[Chemical Formula 8]

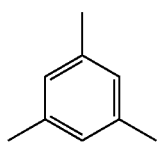

(10)

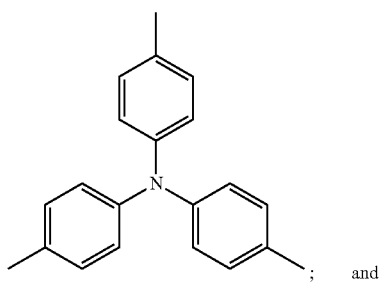

(11)

; and

In the formula (1), $a_1$, $a_2$, and $a_3$ are independently 0 or 1, and such a combination that $a_1$ is 1 and $a_2$ and $a_3$ are each 0 and such a combination that $a_1$, $a_2$, and $a_3$ are each 0 are preferred. $n_1$ and $n_2$ are independently an integer of 1 to 5, preferably an integer of 1 to 3.

In the formula (4), $b_1$ and $b_2$ are independently 0 or 1 and c is an integer of 0 to 3, and it is preferred that $b_1$ and $b_2$ are each 1 and c is an integer of 0 or 1. $m_1$ and $m_2$ are independently an integer of 1 to 5, preferably an integer of 1 to 3.

In the formula (5), $d_1$ to $d_3$ are independently 0 or 1 and it is preferred that $d_1$ to $d_3$ are each 1. $k_1$ to $k_3$ are independently an integer of 1 to 5, preferably an integer of 1 to 3.

It will be noted that in the above illustrations, n means normal, i means iso, s means secondary, and t means tertiary.

The π-conjugated aromatic ring-containing compound represented by the formulas (1), (4), and (5) can be obtained, for example, by the following processes 1 to 7.

It is to be noted that in the following processes, no limitation is placed on the type of reaction solvent provided that it is stable under reaction conditions and is so inert as not to impede the reaction. For instance, solvents are mentioned including water, alcohols (e.g. methanol, ethanol, propanol, butanol, octanol and the like), cellosolves (e.g. methoxyethanol, ethoxyethanol and the like), aprotic organic solvents (e.g. dimethylformamide, dimethylsulfoxide, dimethylacetamide, tetramethylurea, sulforan, N-methylpyrrolidone, N,N-dymethylimidazolidinone, and the like), ethers (e.g. diethyl ether, diisopropyl ether, t-butyl methyl ether, tetrahydrofuran, dioxane, and the like), aliphatic hydrocarbons (e.g. pentane, hexane, c-hexane, octane, decane, decalin, petroleum ether and the like), aromatic hydrocarbons (benzene, chlorobenzene, o-dichlorobenzene, nitrobenzene, toluene, xylene, mesitylene, tetralin and the like), halogenated hydrocarbons (e.g. chloroform, dichloromethane, dichloroethane, carbon tetrachloride and the like), ketones (acetone, methyl ethyl ketone, methyl butyl ketone, methyl isobutyl ketone and the like), lower aliphatic acid esters (e.g. methyl acetate, ethyl acetate, butyl acetate, methyl propionate and the like), alkoxyalkanes (e.g. dimethoxyethane, diethoxyethane and the like), nitriles (e.g. acetonitrile, propionitrile, butyronitrile and the like), and the like.

These solvents maybe appropriately selected while taking the ease in occurrence of reaction into account. In this case, the solvents may be used singly or in combination of two or more. In some cases, an appropriate type of dehydrator or drying agent may be used for use as a non-aqueous solvent.

(1) Process 1

As shown in the following scheme 1, the process 1 is one wherein aromatic ring-containing terminal acetylene (A) and a vinyl halide derivative (B) are subjected to Sonogashira reaction in the presence of a palladium catalyst to prepare intermediate (C), followed by further Sonogashira reaction with a halogenated heteroaromatic compound (D).

Scheme 1

[Chemical Formula 11]

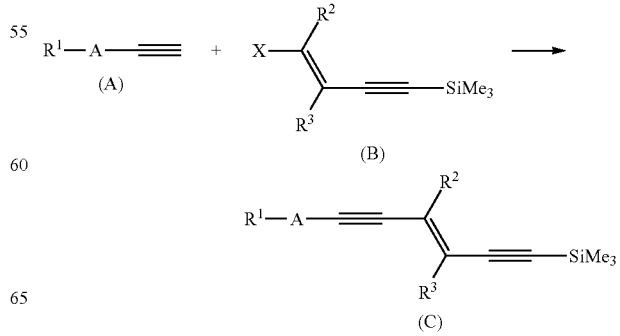

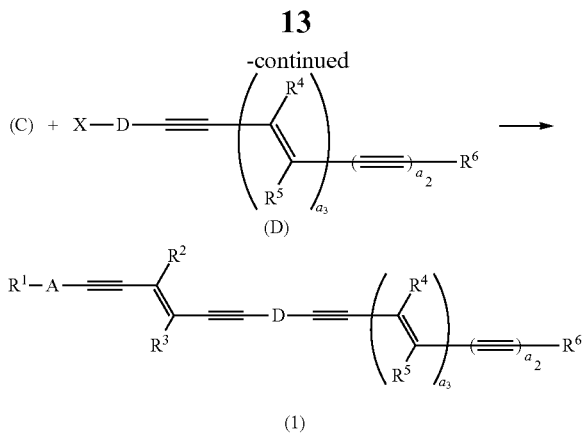

(wherein $R^1$ to $R^6$, A, D, $a_2$, and $a_3$, respectively, have the same meanings as defined before, and X represents a chlorine atom, a bromine atom or an iodine atom).

For the palladium catalyst, those having a variety of structures may be used, of which so-called low-valent palladium complexes are preferably used and especially, zero-valent complexes having a tertiary phosphine or tertiary phosphite ligand are more preferred. Alternatively, an appropriate precursor that is readily converted into a zero-valent complex in a reaction system may also be used. Still alternatively, a complex containing neither a tertiary phosphine nor tertiary phosphite ligand and a tertiary phosphine or a tertiary phosphite may be mixed together to produce a low-valent complex having a tertiary phosphine or tertiary phosphite ligand.

For the tertiary phosphine or tertiary phosphite used as a ligand, mention is made, for example, of triphenylphosphine, diphenylmethylphospine, phenyldimethylphosphine, 1,2-bis(diphenylphosphino)ethane, 1,3-bis(diphenylphosphino)propane, 1,4-bis(diphenylphosphino)butane, 1,1'-bis(diphenylphosphino)ferrocene, trimethylphosphite, triethylphosphite, triphenylphosphite and the like, and complexes containing a mixture of two or more of these ligands.

The use, as a catalyst, of a tertiary phosphine-free or tertiary phosphite-free palladium complex and/or a tertiary phosphine-containing or tertiary phosphite-containing complex, and such a ligand as indicated above in combination is a preferred embodiment.

The tertiary phosphine-free or tertiary phosphite-free palladium complex used in combination with the ligand includes bis(benzylideneacetone) palladium, palladium acetate or the like. For a complex in which a tertiary phosphine or tertiary phosphite is already contained as a ligand, mention is made of dimethylbis(triphenylphosphine)palladium, dimethylbis(diphenylmethylphospine)palladium, (ethylene)bis(triphenylphosphine)palladium, tetrakis(triphenylphosphine)palladium and the like although not limited thereto.

The amount of the palladium catalyst may be a so-called catalytic amount. In general, 20 mole % or below relative to a substrate (B or D) is sufficient and 5 mole % or below is for usual use.

The reaction solvent is not limited in type so far as it does not take part in the reaction and such a solvent as indicated hereinbefore may be used.

The reaction temperature may usually be from −100° C. to a boiling point of a solvent used, preferably within a range of −50° C. to 50° C.

The reaction time may usually be from 0.1 to 1000 hours.

After completion of the reaction, an intended product is extracted with an appropriate solvent, followed by concentration of a solvent under reduced pressure to obtain a crude product.

Further, purification is carried out by a usual method such as distillation, recrystallization, silica gel column chromatography and the like, thereby isolating pure intended product (1).

(2) Process 2

As shown in the following scheme 2, the process 2 is one wherein an aromatic ring-containing vinyl halide derivative (E) and an aromatic ring-containing terminal acetylene derivative (F) are subjected to Sonogashira reaction in the presence of a palladium catalyst.

Scheme 2

[Chemical Formula 12]

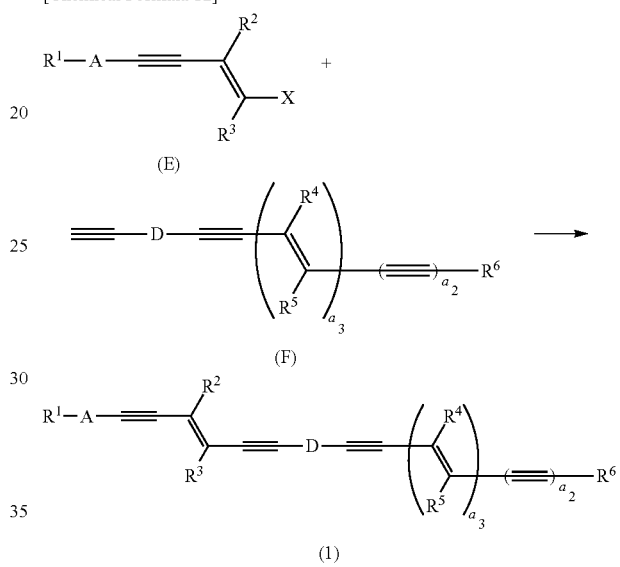

(wherein $R^1$ to $R^6$, A, D, $a_2$, $a_3$, and X, respectively, have the same meanings as defined before).

The intermediate (E) can be prepared according to the following procedure.

More particularly, titanapentadiene intermediate (J), which is obtained by cross coupling reaction between an aromatic ring-containing terminal acetylene (A) and an internal acetylene (H) by means of a divalent titanium reaction agent Ti(O-i-Pr)$_4$/2i-PrMgCl, is treated with iodine or bromine to obtain intermediate (K) (Journal of Organic Chemistry (J. Org. Chem.) (U.S.A.) 1998, Vol. 63, p. 10060 and Journal of American Chemical Society (J. Am. Chem. Soc.) (U.S.A.) 1999, Vol. 121. p. 7342).

Intermediate (L) obtained by dehalogenation reaction of the intermediate (K) is alkyl-substituted, followed by halogen-substitution of the silyl group to obtain intended intermediate (E).

[Chemical Formula 13]

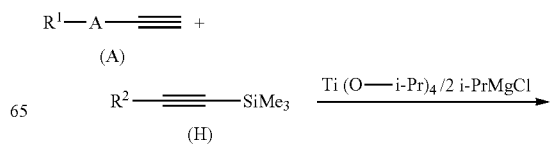

15

-continued

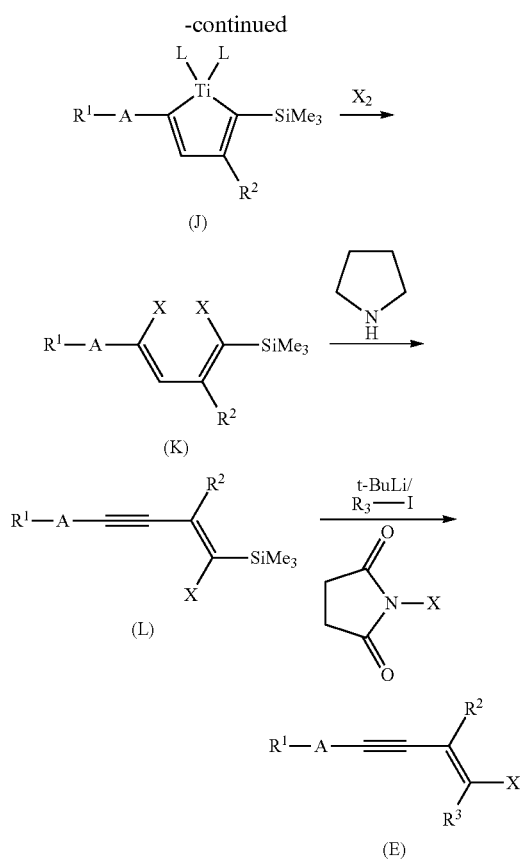

(wherein $R^1$ to $R^3$, A, and X, respectively, have the same meanings as defined before).

(3) Process 3

As shown in the following scheme 3, the process 3 is one wherein aromatic ring-containing terminal acetylene (A) and aromatic ring-containing vinyl halide derivative (G) are subjected to Sonogashira reaction in the presence of a palladium catalyst. The reaction can be carried out under similar conditions as in Process 1.

Scheme 3

[Chemical Formula 14]

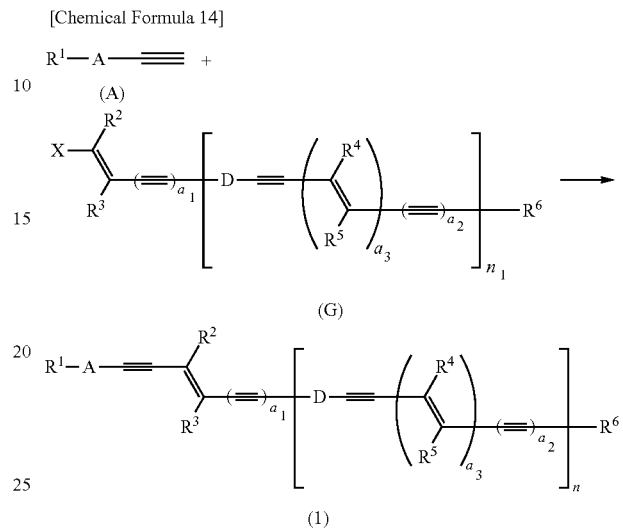

(wherein $R^1$ to $R^6$, A, D, $a_1$ to $a_3$, $n_1$ and X, respectively, have the same meanings as defined before).

(4) Process 4

As shown in the following scheme 4, the process 4 is one wherein aromatic ring-containing terminal acetylene (1a: $R^6$ is a hydrogen atom) and a halogenated aromatic ring (X—$R^{12}$) are subjected to Sonogashira reaction in the presence of a palladium catalyst. The reaction can be carried out under similar conditions as in Process 1.

Scheme 4

[Chemical Formula 15]

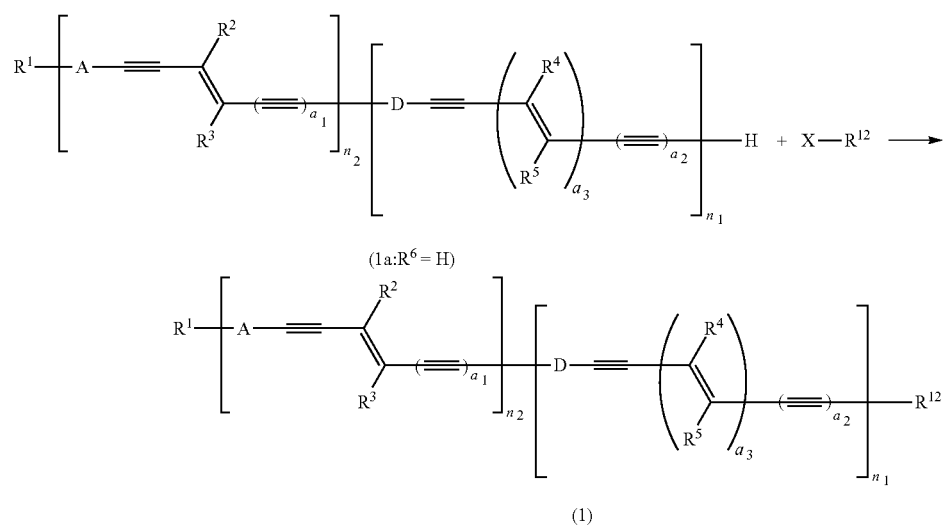

(wherein $R^1$ to $R^5$, A, D, $a_1$ to $a_3$, $n_1$, $n_2$, and X, respectively, have the same meanings as defined before, and $R^{12}$ represents a phenyl group, a naphthyl group, a pyridyl group, a pyrimidinyl group, a pyridazinyl group, a pyrazinyl group, a furanyl group, a pyrrolyl group, a pyrazolyl group, an imidazolyl group or a thienyl group (provided that the phenyl group, naphthyl group, pyridyl group, pyrimidinyl group, pyridazinyl group, pyrazinyl group, furanyl group, pyrrolyl group, pyrazolyl group, imidazolyl group or thienyl group may be optionally substituted with a halogen atom, a cyano group, a nitro group, a dimethylamino group, a diphenylamino group, an alkoxy group having 1 to 3 carbon atoms, an alkyl group having 1 to 10 carbon atoms, or a halogenated alkyl group that has 1 to 10 carbon atoms and may be optionally substituted with a fluorine or chlorine atom)).

(5) Process 5

As shown in the following scheme 5, the process 5 is one wherein heteroaromatic ring-containing vinyl halide derivative (E) and heteroaromatic ring-containing bis terminal acetylene derivative (J) are subjected to Sonogashira reaction in the presence of a palladium catalyst. The reaction can be carried out under similar conditions as in Process 1.

Scheme 5

[Chemical Formula 16]

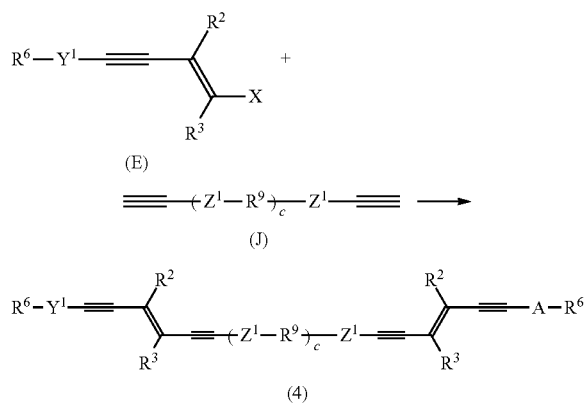

(wherein $R^2$, $R^3$, $R^6$, $R^9$, $Y^1$, $Z^1$, c, and X, respectively, have the same meanings as defined before).

(6) Process 6

As shown in the following scheme 6, the process 6 is one wherein heteroaromatic ring-containing vinyl halide derivative (E) and heteroaromatic ring-containing tris terminal acetylene derivative (K) are subjected to Sonogashira reaction in the presence of a palladium catalyst. The reaction can be carried out under similar conditions as in Process 1.

Scheme 6

[Chemical Formula 17]

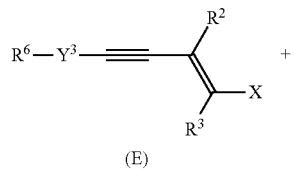

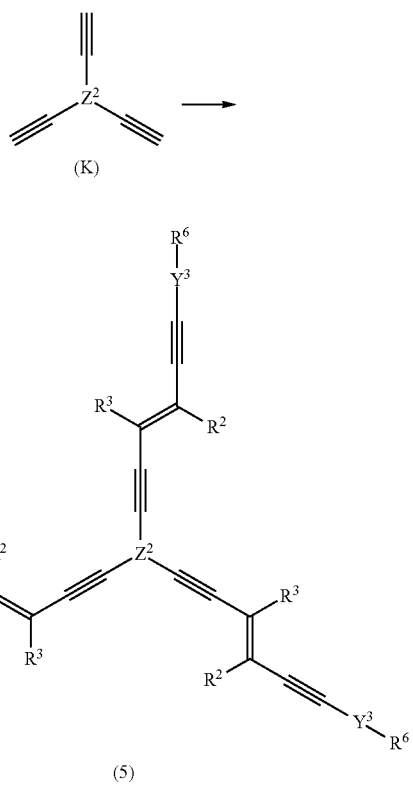

(wherein $R^2$, $R^3$, $R^6$, $Y^3$, $Z^2$, and X, respectively, have the same meanings as defined before).

(7) Process 7

As shown in the following scheme 7, the process 7 is one wherein heteroaromatic ring-containing vinyl halide derivative (E) and tri(ethynylphenyl)amine derivative (L) are subjected to Sonogashira reaction in the presence of a palladium catalyst. The reaction can be carried out under similar conditions as in Process 1.

Scheme 7

[Chemical Formula 18]

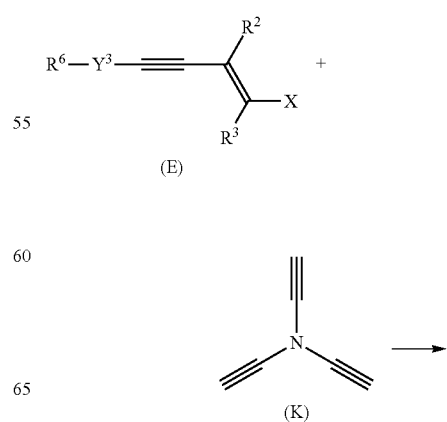

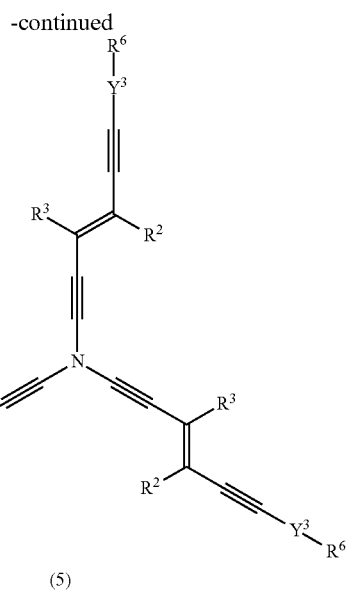

(5)

(wherein $R^2$, $R^3$, $R^6$, $Y^3$, $Z^2$, and X, respectively, have the same meanings as defined before, and N represents a nitrogen atom).

The organic electroluminescent device (hereinafter referred to as organic EL device) of the invention includes an anode and a cathode, and an organic thin film layer interposed their between, wherein the organic thin film layer contains such a π-conjugated aromatic ring-containing compound. Materials other than the π-conjugated aromatic ring-containing compound may be materials known for organic EL devices.

Specific examples of a device arrangement include a device wherein a pair of electrodes are disposed on opposite sides of an emission layer made of a π-conjugated aromatic ring-containing compound, a device wherein a pair of electrodes are disposed on opposite sides of an emission layer made of a mixtures of a π-conjugated aromatic ring-containing compound and a charge transport material (which is intended to generically mean an electron transport material and a hole transport material), and the like. In this case, the electron transport material or hole transport material is not critical in type and may be used by appropriate selection of known ones.

For the formation of the emission layer, various types of known emission materials other than the π-conjugated aromatic ring-containing compound may be appropriately mixed depending on the purpose.

The devices may be provided with an electron transport layer containing an electron transporting material between the cathode and the emission layer, and also a hole transport layer containing a hole transport material between the anode and the emission layer.

Further, the emission layer and the charge transport layer may be constituted of a single layer or a multilayer, respectively.

The method of fabricating an organic EL device using a π-conjugated aromatic ring-containing compound of the invention is not critical and includes, for example, the following methods.

Initially, a transparent or semi-transparent electrode made of an anode material is formed on a transparent substrate such as of glass, a transparent plastic or the like. For the anode material, conductive metal oxide films, semi-transparent metal thin films and the like are used. More particularly, conductive glasses such as indium/tin/oxide (ITO), tin oxide and the like, Au, Pt, Ag, Cu and the like are used. For the formation of the electrode, the mention is made of those methods of forming a thin film such as by a vacuum deposition method, a sputtering method, a plating method and the like.

An emission layer containing, as a light-emitting material, a π-conjugated aromatic ring-containing compound or both a π-conjugated aromatic ring-containing compound and a charge transport material is formed on the resulting anode.

For the formation method, mention is made of a spin coating method, a casting method, a dipping method, a bar coating method, a roll coating method, a gravure coating method, a flexo printing method, a spray coating method and the like using a melt, solution or mixed solution of these materials.

Where thin film formation is carried out according to a coating method such as a spin coating method, it is preferred to dry under heating conditions in a reduced or inert atmosphere so as to remove a solvent therefrom.

It will be noted that in case where an emission layer and a charge transport layer are stacked, a hole transport layer and/or electron transport layer may be formed by a method wherein the hole transport layer is formed on the anode prior to formation of an emission layer by the above-mentioned method, or by a method wherein an electron transport layer is formed after formation of the emission layer. In this case, although the method of forming the charge transport layer is not critical, mention is made of a method of vacuum deposition from a powdery state, or a spin coating method, casting method, dipping method, bar coating method, roll coating method or the like using a charge transport material solution.

Subsequently, a cathode by forming an electrode made of a cathode material is formed on the emission layer (or electron transport layer), i.e. on the substrate as with the case of the anode to obtain an organic EL device. In the case, a cathode material is not critical in type, and materials whose ionization energy is small are preferred. For instance, Al, In, Mg, Ca, Li, Mg—Ag alloy, In—Ag alloy, Mg—In alloy, Mg—Al alloy, Mg—Li alloy, Al—Li alloy, Al—Ca alloy, graphite thin films and the like are mentioned. For the stacking method of a cathode material on the substrate, mention is made of a vacuum deposition method, a sputtering method and the like.

EXAMPLES

The invention is more particularly described by way of examples, which should not be construed as limiting the invention thereto.

It will be noted that analyzing conditions used in the examples are as follows.

Measuring conditions of $^1$H NMR (300 MHz) and $^{13}$C NMR (75 MHz)
  Apparatus: Varian Gemini-300
  Solvent for measurement: CDCl$_3$
  Standard substance: tetramethylsilane (TMS)
    (δ 0.0 ppm for $^1$H)
    CDCl$_3$ (δ 77.0 ppm for $^{13}$C)
IR measuring apparatus: JASCO A-100
UV/Vis measuring apparatus: HITACHI U-2000
MALDI-TOF-MS measuring apparatus: SHIMADZU
  MALDI-TOFMS AXIMA-CFR
Melting point measuring apparatus: Yanaco MP-J3
Elementary analyzer: Elementar Vario-EL

[1] Synthesis of π-Conjugated Aromatic Ring-Containing Compounds

Example 1

Synthesis of Trans-Silylated (Thiophene-Enediyne) Compound 8

(a) Synthesis of 4-thienyl-1,4-diiodo-1,3-diene compound 3

[Chemical Formula 19]

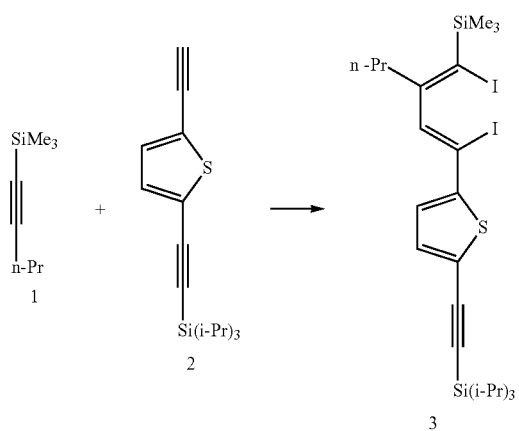

(wherein Me represents a methyl group, n-Pr represents an n-propyl group and i-Pr represents an i-propyl group).

Tetra-i-propoxytitanium (1.24 ml, 4.19 mmols) was added to an ether (40 ml) solution of 1-trimethylsiyl-1-pentyn 1 (0.534 g, 3.81 mmols), followed by cooing to −78° C. and gradual addition of i-propylmagnesium chloride (1.95M/ether solution, 4.30 ml, 8.38 mmols).

The temperature was raised to −50° C. in 1 hour, at which agitation was carried out over 4 hours.

An ether (5 ml) solution of a terminal acetylene compound 2 (0.896 g, 3.05 mmols) was added, followed by agitation at −50° C. for 3 hours.

Iodine (2.41 g, 9.53 mmols) was added, followed by agitation at −50° C. for 30 minutes and further agitation at room temperature for 2 hours.

Water was added to the resulting reaction solution at 0° C. and agitated for 30 minutes, followed by celite filtration. A saturated sodium thiosulfate aqueous solution was added to the resulting filtrate. After confirmation of excess iodine being not found, an aqueous phase after funnel separation was further extracted with hexane, and a combined organic phase was dried over anhydrous magnesium sulfate.

After filtration, the crude product obtained by concentrating the resulting filtrate under reduced pressure was confirmed with NMR and used for subsequent reaction as it is.

$^1$H NMR (300 MHz, CDCl$_3$) δ 7.15 (d, J=3.9 Hz, 1H), 7.12 (d, J=3.9 Hz, 1H), 6.73 (s, 1H), 2.56-2.46 (m, 2H), 1.65-1.50 (m, 2H), 1.20-1.05 (m, 21H), 0.91 (t, J=7.5 Hz, 3H), 0.36 (s, 9H).

(b) Synthesis of Cis-Thienyliodo-Enyne Compound 4

[Chemical Formula 20]

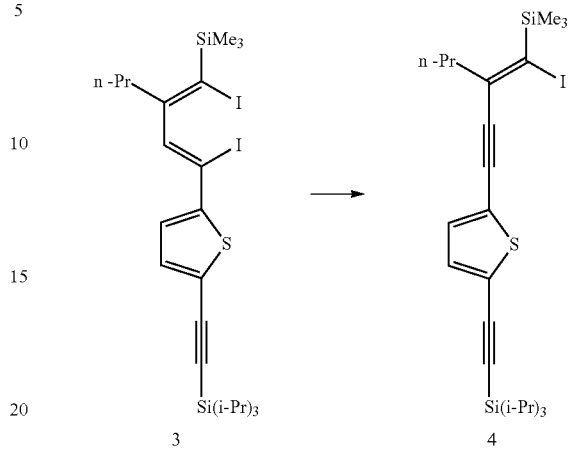

(wherein Me represents a methyl group, n-Pr represents an n-propyl group, and i-Pr represents an i-propyl group).

A THF (6 ml) solution of the crude product of the thus obtained 4-thienyl-1,4-diiodo-1,3-diene compound 3 was cooled down to 0° C., to which pyrrolidine (1.27 ml, 15.3 mmols) was added and agitated for 12 hours, followed by addition of water to the reaction solution at 0° C. for quenching.

After funnel separation, the resulting aqueous phase was further extracted with hexane and a combined organic phase was washed with a saturated saline solution, followed by drying the organic phase over anhydrous magnesium sulfate.

After filtration, the crude product obtained by concentrating the resulting filtrate under reduced pressure was confirmed with NMR and used as it is for subsequent reaction.

$^1$H NMR (300 MHz, CDCl$_3$) δ 7.10 (d, J=3.6 Hz, 1H), 7.08 (d, J=3.6 Hz, 1H), 2.44-2.32 (m, 2H), 1.72-1.55 (m, 2H), 1.20-1.05 (m, 21H), 0.94 (t, J=6.9 Hz, 3H), 0.33 (s, 9H).

(c) Synthesis of Thienylsilylenyne Compound 5

[Chemical Formula 21]

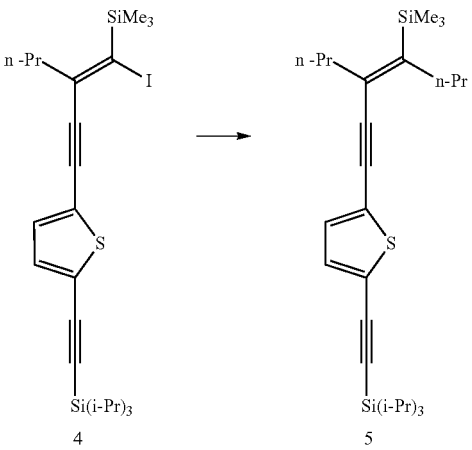

(wherein Me represents a methyl group, n-Pr represents an n-propyl group, and i-Pr represents an i-propyl group).

The thus obtained crude product of cis-thienyliodoeyne compound 4 was dissolved in ether (7 ml) and cooled down to −78° C.

t-butyl lithium (1.50 M/pentane solution, 2.83 ml, 4.24 mmols) was added, followed by agitation for 40 minutes as it is.

Iodopropane (0.640 ml, 6.06 mmols) was dropped and agitated at room temperature overnight, after which water was added to the reaction solution at 0° C. for quenching.

The resulting product was extracted from an aqueous phase with ether and washed with a saturated saline solution, and the resulting organic phase was dried over anhydrous magnesium sulfate.

After filtration, the crude product obtained by concentrating the resulting filtrate under reduced pressure was confirmed with NMR and used as it is for subsequent reaction.

$^1$H NMR (300 MHz, CDCl$_3$) δ 7.06 (d, J=3.9 Hz, 1H), 6.96 (d, J=3.9 Hz, 1H), 2.38 (t, J=7.5 Hz, 2H), 2.25 (d, J=7.5 Hz, 2H), 1.70-1.50 (m, 4H), 1.20-1.05 (m, 21H), 0.97 (t, J=7.5 Hz, 6H), 0.19 (s, 9H).

(d) Synthesis of Trans-Thienyliodo-Enyne Compound 6

[Chemical Formula 22]

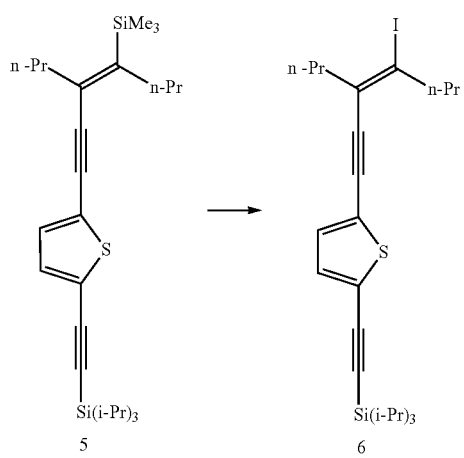

(wherein n-Pr represents an n-propyl group, and i-Pr represents an i-propyl group).

The thus obtained crude product of thienylsilylenyne compound 5 was dissolved in dichloromethane (10 ml), to which N-iodosuccinimide (0.893 g, 4.04 mmols) was added and agitated at room temperature under light-shielded conditions for 2 hours, followed by addition of a saturated sodium thiosulfate aqueous solution to the reaction solution at 0° C. and quenching. The organic phase obtained by extracting the resulting reaction product with dichloromethane from an aqueous phase was washed with a saturated saline solution, followed by drying over anhydrous magnesium sulfate.

After filtration, the crude product obtained by concentrating the resulting filtrate under reduced pressure was purified by use of silica gel column chromatography (hexane) to obtain trans-thienyliodo-enyne compound 6 at a four-step ((a)-(d)) yield of 39% (0.616 g).

$^1$H NMR (300 MHz, CDCl$_3$) δ 7.08 (d, J=3.9 Hz, 1H), 7.01 (d, J=3.9 Hz, 1H), 2.90 (t, J=7.5 Hz, 2H), 2.42 (t, J=7.5 Hz, 2H), 1.70-1.58 (m, 4H), 1.19-1.06 (m, 21H), 1.01 (t, J=7.5 Hz, 3H), 0.98 (t, J=7.2 Hz, 3H).

$^{13}$C NMR (75 MHz, CDCl$_3$) δ 132.31, 131.00, 127.71, 125.06, 124.43, 118.17, 98.81, 97.08, 90.73, 86.74, 45.75, 43.16, 22.59, 21.17, 18.52, 13.43, 12.70, 11.17.

IR (neat) 2959, 2866, 2142, 1462, 883, 736, 675 cm$^{-1}$.

Anal. Calculated for C$_{25}$H$_{37}$ISSi: C, 57.24; H, 7.11. Found: C, 57.40; H, 7.46.

(e) Synthesis of Trans-Silylated (Thiophene-Enediyne) Compound 8

[Chemical Formula 23]

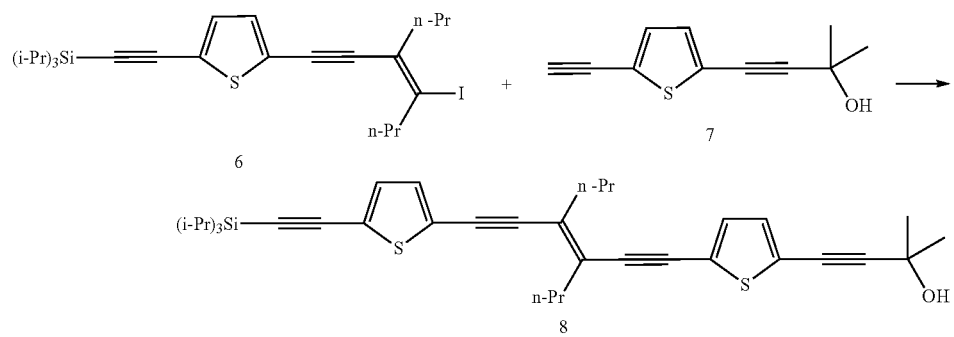

(wherein n-Pr represents an n-propyl group, and i-Pr represents an i-propyl group).

The thus obtained trans-thienyliodo-enyne compound 6 (0.943 g, 1.80 mmols) was dissolved in degassed THF (5 ml), to which tetrakistriphenylphosphine palladium (52.0 mg, 0.450 mmols), cuprous iodide (17.1 mg, 0.0900 mmols) and diethylamine (3.7 ml) were added, followed by dropping a degassed THF (10 ml) solution of thiophene acetylene compound 7 (0.285 g, 1.50 mmols).

The reaction solution was agitated at room temperature for six hours, to which water was added to the reaction solution for quenching.

The organic phase obtained by extracting the reaction product from the aqueous phase with ether was washed with a saturated saline solution, followed by drying over anhydrous magnesium sulfate.

After filtration, the crude product obtained by concentrating the resulting filtrate under reduced pressure was purified with silica gel column chromatography (hexane) to obtain trans-silylated (thiophene-enediyne) compound 8 at 89% (0.784 g).

$^1$H NMR (300 MHz, CDCl$_3$) δ 7.09 (d, J=3.9 Hz, 1H), 7.06-6.95 (m, 3H), 2.50 (t, J=7.5 Hz, 4H), 2.16 (br.s, 1H), 1.72-1.56 (m, 4H), 1.61 (s, 6H), 1.23-1.05 (m, 21H), 0.98 (t, J=7.2 Hz, 6H).

$^{13}$C NMR (75 MHz, CDCl$_3$) δ 132.39, 132.11, 131.29, 131.21, 129.92, 129.78, 125.19, 124.74, 124.53, 124.25, 98.80, 98.67, 97.31, 94.08, 93.90, 91.84, 91.68, 75.13, 65.72, 36.83 (×2), 31.15, 21.75 (×2), 18.50, 13.52 (×2), 11.14.

IR (neat) 3373, 2957, 2866, 2141, 1461, 1164, 884, 802, 752, 674 cm$^{-1}$.

UV/Vis (CHCl$_3$): λ$_{max}$ (ε) [nm]=385 (23 400).

MALDI-TOF-MS (DHB): 586.3 (calculated for C$_{36}$H$_{46}$OS$_2$Si: 586.3).

Anal. Calculated for C$_{36}$H$_{46}$OS$_2$Si: C, 73.66; H, 7.90. Found: C, 73.48; H, 7.83.

Example 2

Synthesis of Trans-(Thiophene-Enediyne) Compound 9

[Chemical Formula 24]

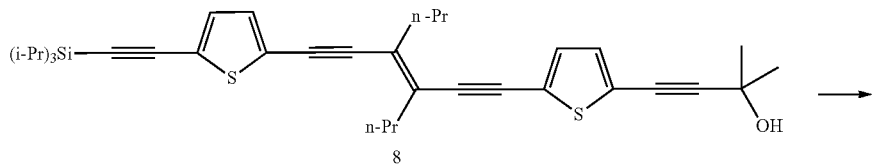

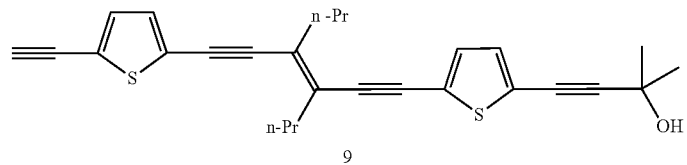

(wherein n-Pr represents an n-propyl group, and i-Pr represents an i-propyl group).

The trans-silylated (thiophene-enediyne) compound 8 (0.729 g, 1.24 mmols) obtained in Example 1 was dissolved in THF (4 ml), to which tetrabutylammonium fluoride (1.0 M/THF solution, 1.87 ml, 1.87 mmols) was added at 0° C., followed by agitation for 3 minutes.

The reaction solution was diluted with ether and water and, after funnel separation, the resulting aqueous solution was extracted with ether. A combined organic phase was dried over anhydrous magnesium sulfate.

After filtration, the crude product obtained by concentrating the resulting filtrate under reduced pressure was confirmed with NMR and used as it is for subsequent reaction.

Example 3

Synthesis of Trans-Silylated (Thiophene-Enediyne) Dimer Compound 10

[Chemical Formula 25]

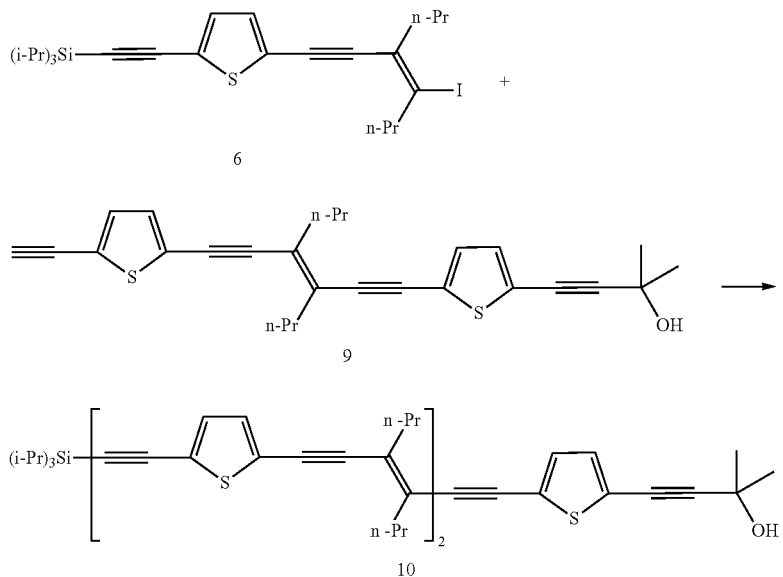

(wherein n-Pr represents an n-propyl group, and i-Pr represents an i-propyl group).

The trans-thienyliodo-enyne compound 6 (0.780 g, 1.49 mmols) obtained in Example 1-(d) was dissolved in degassed THF (4 ml), to which tetrakistriphenylphosphine palladium (43.0 mg, 0.0372 mmols), cuprous iodide (14.0 mg, 0.0740 mmols) and diethylamine (3.1 ml) were added at room temperature, in which a degassed THF (8 ml) solution of the crude product of the trans(thiophene-enediyne) compound 9 obtained in Example 2 was dropped.

The reaction solution was agitated as it is at room temperature for 6 hours, after which water was added to the reaction solution for quenching.

After extraction with ether from an aqueous phase and washing with a saturated saline solution, the resulting organic phase was dried over anhydrous magnesium sulfate.

After filtration, the crude product obtained by concentrating the resulting filtrate under reduced pressure was purified with silica gel chromatography (hexane) to obtain trans-silylated (thiophene-enediyne) dimer compound 10 at a two-step yield of 69%.

m.p.=73-77° C.

$^1$H NMR (300 MHz, CDCl$_3$) δ 7.13-6.95 (m, 6H), 2.51 (t, J=7.5 Hz, 8H), 2.26 (br.s, 1H), 1.75-1.53 (m, 8H), 1.61 (s, 6H), 1.18-1.05 (m, 21H), 1.00 (t, J=7.2 Hz, 12H).

$^{13}$C NMR (75 MHz, CDCl$_3$) δ 132.39, 132.08, 131.63 (×2), 131.29, 131.19, 129.88 (×2), 129.81, 129.80, 125.19, 125.07 125.03, 124.69, 124.53, 124.30, 98.80, 98.73, 97.30, 94.63, 94.59, 94.08, 93.94, 91.91, 91.90, 91.87, 91.76, 75.09, 65.67, 36.81 (×4), 31.12, 21.75 (×4), 18.48, 13.50 (×4), 11.13.

IR (KBr) 3397, 2959, 2866, 1460, 801, 752 cm$^{-1}$.

UV/Vis (CHCl$_3$): λ$_{max}$ (0 [nm]=407 (52 000).

MALDI-TOF-MS (DHB): 826.4 (calculated for C$_{52}$H$_{62}$OS$_3$Si: 826.4).

Anal. Calculated for C$_{52}$H$_{62}$OS$_3$Si: C, 75.49; H, 7.55. Found: C, 75.07; H, 7.19.

Example 4

Synthesis of Trans-(Thiophene-Enediyne)Dimer Compound 11

[Chemical Formula 26]

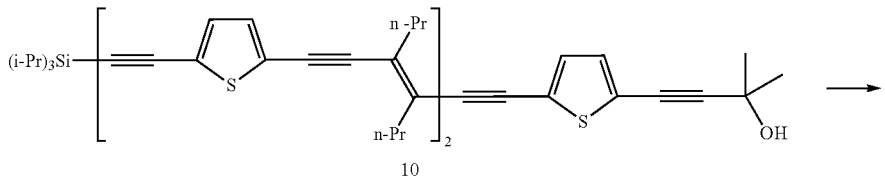

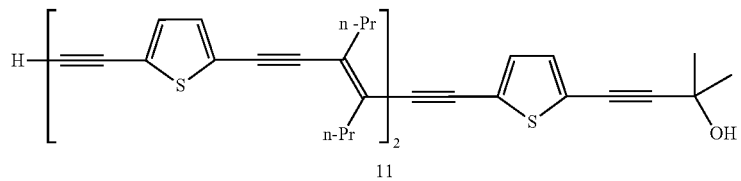

(wherein n-Pr represents an n-propyl group, and i-Pr represents an i-propyl group).

Using the trans-silylated (thiophene-enediyne) dimer compound 10 obtained in Example 3, trans-(thiophene-enediyne) dimer compound 11 was obtained in the same manner as in Example 2. The resulting crude product was confirmed with NMR and used as it is for subsequent reaction.

Example 5

Synthesis of Trans-Silylated (Thiophene-Enediyne) Trimer Compound 12

[Chemical Formula 27]

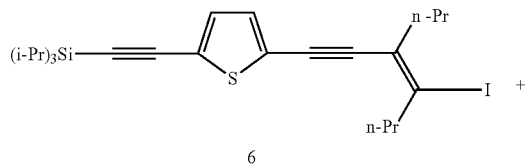

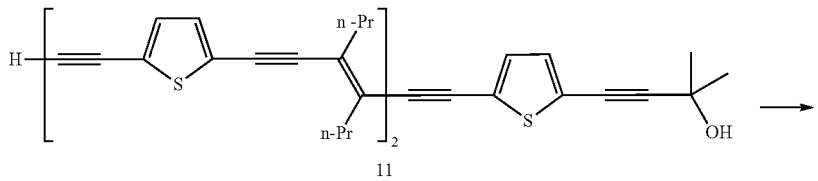

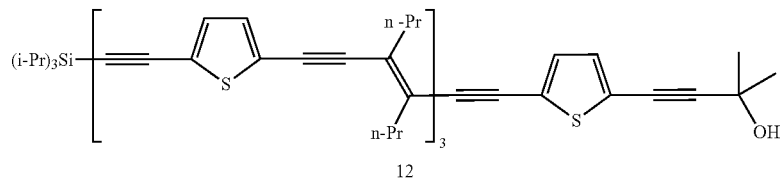

(wherein n-Pr represents an n-propyl group, and i-Pr represents an i-propyl group).

Using the trans-(thiophene-enediyne) dimer compound 11 obtained in Example 4, trans-silylated (thiophene-enediyne) trimer compound 12 was obtained at a two-step yield of 63% in the same manner as in Example 3.

$^1$H NMR (300 MHz, CDCl$_3$) δ 7.13-6.95 (m, 8H), 2.58-2.44 (m, 12H), 2.15 (br.s, 1H), 1.75-1.54 (m, 12H), 1.62 (s, 6H), 1.17-1.06 (m, 21H), 1.03-0.95 (m, 18H).

$^{13}$C NMR: δ 132.40, 132.11, 131.67 (×4), 131.32, 131.21, 129.88 (×3), 129.85 (×2), 129.81, 125.19, 125.09 (×2), 125.06 (×2), 124.71, 124.53, 124.29, 98.80, 98.71, 97.32, 94.65 (×3), 94.09, 93.97, 93.94, 91.97, 91.95, 91.92 (×2), 91.90, 91.77, 75.10, 65.71, 36.83 (×6), 31.15, 21.77 (×6), 18.50, 13.53 (×6), 11.14.

IR (neat) 3375, 2959, 2866, 1461, 1378, 1199, 1162, 800, 751 cm$^{-1}$.

UV/Vis (CHCl$_3$): λ$_{max}$ (ε) [nm]=427 (58 200).

MALDI-TOF-MS (DHB): 1066.2 (calculated for $C_{68}H_{78}OS_4Si$: 1066.5). Anal. Calculated for $C_{68}H_{78}OS_4Si$: C, 76.49; H, 7.36. Found: C, 76.55; H, 7.53.

Example 6

Synthesis of Trans-Silylated (Pyridine-Enediyne) Compound 19

(a) Synthesis of 4-pyridyl-1,4-diiodo-1,3-diene compound 14

[Chemical Formula 28]

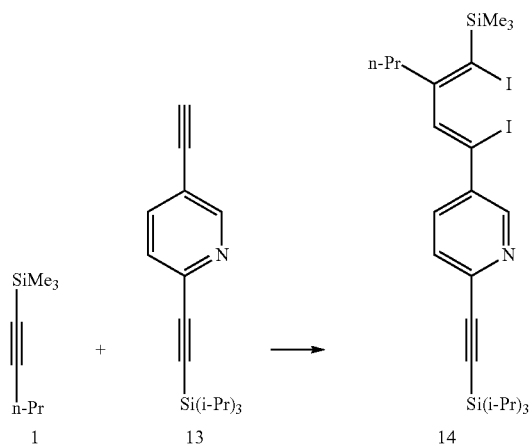

(wherein Me represents a methyl group, n-Pr represents an n-propyl group, and i-Pr represents an i-propyl group).

Tetra-i-propoxy titanium (7.40 ml, 25.1 mmols) was added to an ether (250 ml) solution of 1-triemthylsilyl-1-pentyne 1 (2.94 g, 20.9 mmols) and subsequently cooled down to −78° C., followed by gradual addition of i-propylmagnesium chloride (2.10 M/ether solution, 24.0 ml, 50.2 mmols).

The temperature was raised to −50° C. in 1 hour, at which agitation was continued for 4 hours.

An ether (20 ml) solution of terminal acetylene compound 13 (5.34 g, 18.9 mmols) was added, followed by agitation at −50° C. for 3 hours.

Iodine (13.3 g, 52.3 mmols) was added, followed by agitation at −50° C. for 30 minutes and further agitation at room temperature for 2 hours.

Water was added to the resulting reaction solution at 0° C. and agitated for 30 minutes, followed by celite filtration. A saturated sodium thiosulfate aqueous solution was added to the filtrate and after confirmation of the absence of excess iodine, an aqueous phase after funnel separation was extracted with hexane and a combined organic phase was dried over anhydrous magnesium sulfate.

After filtration, the crude product obtained by concentrating the resulting filtrate under reduced pressure was confirmed with NMR and used as it is for subsequent reaction.

$^1$H NMR (300 MHz, CDCl$_3$) δ 8.77 (d, J=2.1 Hz, 1H), 7.79 (dd, J=2.1, 8.1 Hz, 1H), 7.42 (d, J=8.1 Hz, 1H), 6.68 (s, 1H), 2.60-2.48 (m, 2H), 1.60-1.45 (m, 2H), 1.20-1.10 (m, 21H), 0.94 (t, J=6.9 Hz, 3H), 0.36 (s, 9H).

(b) Synthesis of Cis-Pyridyliodo-Enyne Compound 15

[Chemical Formula 29]

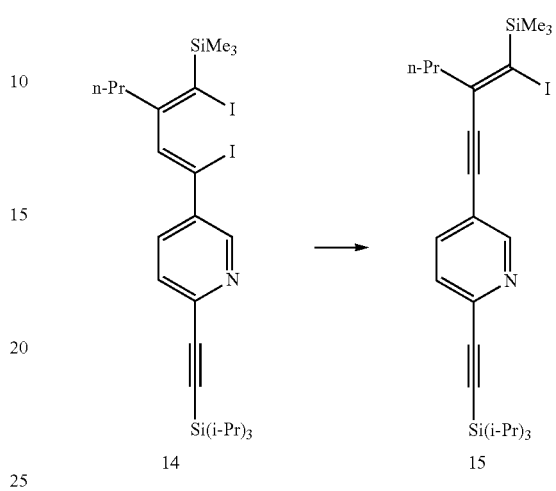

(wherein Me represents a methyl group, n-Pr represents an n-propyl group, and i-Pr represents an i-propyl group).

The THF (38 ml) solution of the crude product of 4-pyridyl-1,4-diiodo-1,3-diene compound 14 obtained above was cooled down to 0° C., to which pyrrolidine (7.90 ml, 94.5 mmols) was added, followed by agitation for 3 hours. Water was added to the reaction solution for quenching.

After funnel separation, an aqueous phase was extracted with hexane, and a combined organic phase was washed with a saturated saline solution, after which the organic phase was dried over anhydrous magnesium sulfate.

After filtration, the crude product obtained by concentrating the resulting filtrate under reduced pressure was confirmed with NMR and used as it is for subsequent reaction.

$^1$H NMR (300 MHz, CDCl$_3$) δ 8.69 (dd, J=0.9, 2.1 Hz, 1H), 7.73 (dd, J=2.1, 8.1 Hz, 1H), 7.41 (dd, J=0.9, 8.1 Hz, 1H), 2.44-2.36 (m, 2H), 1.75-1.60 (m, 2H), 1.20-1.10 (m, 21H), 0.96 (t, J=7.2 Hz, 3H), 0.34 (s, 9H).

(c) Synthesis of Pyridylsilyl-Enyne Compound 16

[Chemical Formula 30]

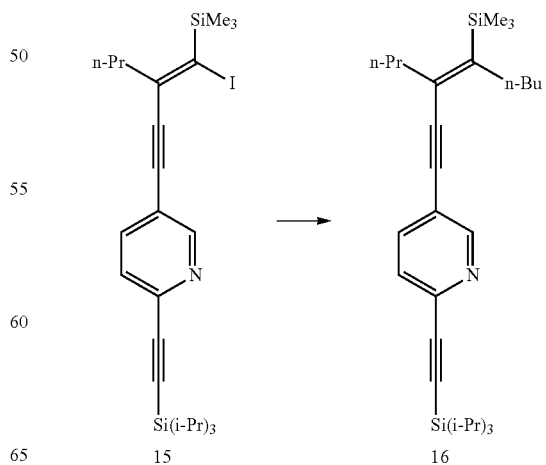

(wherein Me represents a methyl group, n-Pr represents an n-propyl group, i-Pr represents an i-propyl group and n-Bu represents an n-butyl group).

n-Butyl lithium (1.58 M/hexane, 38.9 ml, 61.5 mmols) was dropped in a THF (150 ml) solution of thiophenol (6.30 ml, 61.5 mmols) at 0° C., followed by agitation for 30 minutes to prepare lithium thiophenolate.

Separately, a THF (150 ml) suspension of cuprous iodide (11.7 g, 61.5 mmols) was cooled to 0° C., to which the THF solution of the prepared lithium thiophenolate was added. The reaction solution was agitated at 0° C. until the solution turned yellow and transparent. After cooling the reaction solution to −78° C., n-butyl lithium (1.58 M/hexane solution, 36.7 ml, 58.0 mmols) was added and agitated for 10 minutes. A THF (20 ml) solution of the crude product of cis-pyridyliodo-enyne compound 15 obtained above as added to the reaction solution at −78° C., followed by agitation at the temperature for 1 hour as it is. Moreover, the temperature was raised to 0° C. and agitation was continued overnight, followed by addition of a saturated sodium hydrogencarbonate aqueous solution for quenching.

After funnel separation, an aqueous phase was extracted with ether, and a combined organic phase was washed with a saturated saline solution, after which the organic phase was dried over anhydrous magnesium sulfate.

After filtration, the crude product obtained by concentrating the resulting filtrate under reduced pressure was confirmed with NMR and used as it is for subsequent reaction.

$^1$H NMR (300 MHz, CDCl$_3$) δ 8.60-8.58 (m, 1H), 7.61 (dd, J=2.1, 8.1 Hz, 1H), 7.39 (dd, J=0.9, 8.1 Hz, 1H), 2.46-2.40 (m, 2H), 2.31-2.24 (m, 2H), 1.75-1.55 (m, 4H), 1.40-1.30 (m, 2H), 1.20-1.10 (m, 21H), 0.97 (t, J=7.2 Hz, 3H), 0.94 (t, J=7.5 Hz, 3H), 0.19 (s, 9H).

(d) Synthesis of Trans-Pyridyliodo-Enyne Compound 17

[Chemical Formula 31]

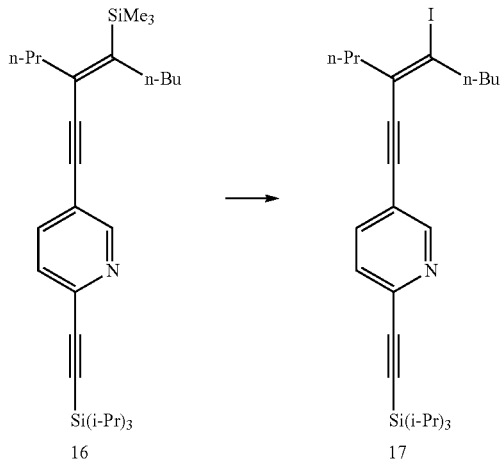

(wherein n-Pr represents an n-propyl group, i-Pr represents an i-propyl group and n-Bu represents an n-butyl group).

The thus obtained crude product of pyridylsilylenyne compound 16 was dissolved in dichloromethane (37 ml), to which N-iodosuccinimide (3.25 g, 14.7 mmols) was added and agitated at room temperature under light-shielded conditions.

After confirmation (about five days) of the disappearance of the pyridylsilylenyne compound 16 with TLC, a saturated sodium thiosulfate aqueous solution was added to the reaction solution at 0° C. for quenching.

After extraction from an aqueous phase with dichloromethane and washing with a saturated saline solution, the organic phase was dried over anhydrous magnesium sulfate.

After filtration, the crude product obtained by concentrating the resulting filtrate under reduced pressure was purified by use of silica gel column chromatography (hexane/ether=30/1) to obtain trans-pyridyliodo-enyne compound 17 at a four-step yield of 32% (3.25 g).

$^1$H NMR (300 MHz, CDCl$_3$) δ 8.57 (d, J=2.1 Hz, 1H), 7.61 (dd, J=2.1, 7.8 Hz, 1H), 7.38 (d, J=7.8 Hz, 1H), 2.91 (t, J=7.2 Hz, 2H), 2.38 (t, J=6.9 Hz, 2H), 1.66-1.50 (m, 4H), 1.40-1.28 (m, 2H), 1.20-1.10 (m, 21H), 0.97 (t, J=7.2 Hz, 3H), 0.92 (t, J=6.9 Hz, 3H).

$^{13}$C NMR (75 MHz, CDCl$_3$) δ 151.84, 141.63, 137.72, 127.08, 126.89, 119.50, 119.36, 105.53, 93.74, 90.92, 90.35, 43.63, 43.18, 31.36, 21.36, 21.18, 18.56, 13.94, 13.48, 11.12.

IR (neat) 2957, 2866, 2200, 2160, 1583, 1540, 1465, 1365, 1249, 1017, 995, 882, 837, 676 cm$^{-1}$.

Anal. Calculated for C$_{27}$H$_{40}$INSi: C, 60.77; H, 7.56. Found: C, 60.69; H, 7.73.

(e) Synthesis of Trans-Silylated (Pyridine-Enediyne) Compound 19

[Chemical Formula 32]

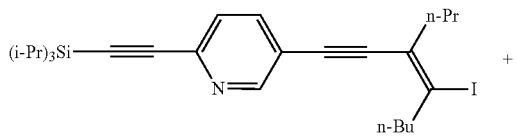

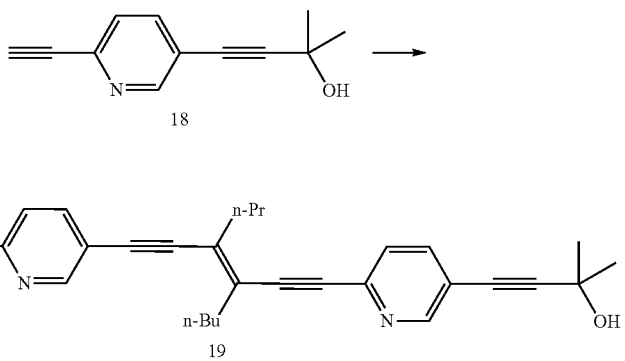

(wherein n-Pr represents an n-propyl group, i-Pr represents an i-propyl group and n-Bu represents an n-butyl group).

The thus obtained trans-pyridyliodo-enyne compound 17 (0.1635 g, 0.311 mmols) was dissolved in a degassed THF (1 ml), to which tetrakistriphenylphosphine palladium (18.0 mg, 0.0160 mmols), cuprous iodide (6.00 mg, 0.0320 mmols) and diethylamine (0.162 ml, 5.28 mmols) were added at room temperature, followed by dropping a degassed THF (2 ml) solution of pyridyl acetylene compound 18 (52.0 mg, 0.280 mmols).

The reaction solution was agitated at room temperature for 3 hours as it is, to which water was added to the reaction solution for quenching.

After extraction with ether from an aqueous solution and washing with a saturated saline solution, the organic phase was dried over anhydrous magnesium sulfate.

After filtration, the crude product obtained by concentrating the resulting filtrate under reduced pressure was purified with silica gel column chromatography (hexane/ether=3/1) to obtain trans-silylated (pyridine-enediyne) compound 19 at 67% (0.110 g).

m.p. 76-83° C.

$^1$H NMR (300 MHz, CDCl$_3$) δ 8.65-8.61 (m, 2H), 7.66 (dd, J=2.1, 8.1 Hz, 1H), 7.64 (dd, J=2.1, 8.1 Hz, 1H), 7.42 (d, J=8.1 Hz, 1H), 7.37 (d, J=8.1 Hz, 1H), 2.69 (br.s, 1H), 2.59 (t, J=7.5 Hz, 4H), 1.76-1.60 (m, 4H), 1.63 (s, 6H), 1.44-1.32 (m, 2H), 1.20-1.10 (m, 21H), 0.99 (t, J=8.0 Hz, 3H), 0.94 (t, J=7.5 Hz, 3H).

$^{13}$C NMR (75 MHz, CDCl$_3$) δ 152.64, 152.15, 142.10, 141.94, 138.65, 138.03, 131.27, 130.60, 127.11, 126.54, 119.65, 118.96, 105.65, 99.23, 97.88, 95.81, 94.14, 93.76, 90.68, 78.73, 65.47, 36.89, 34.73, 31.23, 30.59, 22.08, 21.70, 18.52, 13.80, 13.47, 11.10.

IR (KBr) 3375, 2928, 2866, 2153, 1909, 1658, 1505, 1462, 1378, 1164, 883, 836 cm$^{-1}$.

UV/Vis (CHCl$_3$): λ$_{abs}$ (ε) [nm]=312 (21 400), 337 (38 300), 359 (53 100), 386 (34 400).

MALDI-TOF-MS (DHB): 590.4 (calculated for: 590.4).

Anal. Calculated for: C, 79.27; H, 8.53; N, 4.74. Found: C, 79.08; H, 8.45; N, 4.61.

Example 7

Synthesis of Trans-(Pyridine-Enediyne) Compound 20

[Chemical Formula 33]

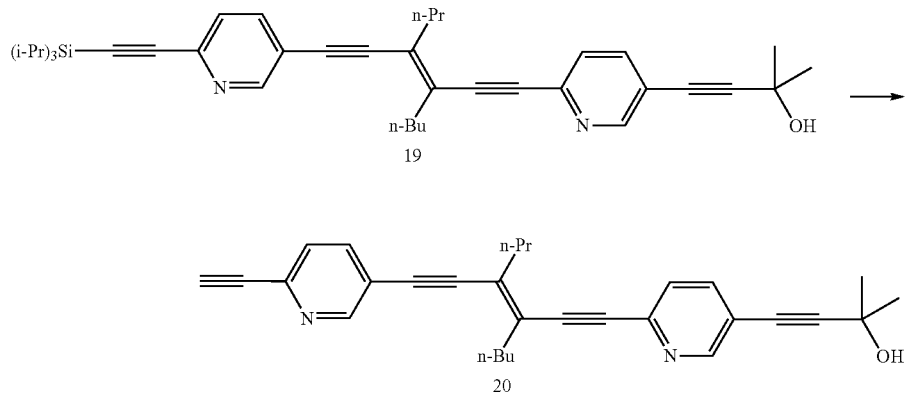

(wherein n-Pr represents an n-propyl group, i-Pr represents an i-propyl group and n-Bu represents an n-butyl group).

The trans-silylated (pyridine-enediyne) compound 19 (61.5 mg, 0.104 mmols) obtained in Example 6 was dissolved in THF (6 ml), to which tetrabutylammonium fluoride (1.0 M/THF solution, 0.156 ml, 0.156 mmols) was added at 0° C., followed by agitation for 30 minutes.

The reaction solution was diluted with ether and water and, after funnel separation, the aqueous phase was further extracted with ether. A combined organic phase was dried over anhydrous magnesium sulfate.

After filtration, the crude product obtained by concentrating the resulting filtrate under reduced pressure was confirmed with NMR and used as it is for subsequent reaction.

Example 8

Synthesis of Trans-Silylated (Pyridine-Enediyne) Dimer Compound 21

After extraction from an aqueous phase with chloroform and washing with a saturated saline solution, the organic phase was dried over anhydrous magnesium sulfate.

After filtration, the crude product obtained by concentrating the resulting filtrate under reduced pressure was purified by silica gel column chromatography (hexane/ether=2/1) to obtain trans-silylated (pyridine-enediyne) dimer compound 21 at a two-step yield of 75% (65.6 mg).

m.p. 120-123° C.

$^1$H NMR (300 MHz, CDCl$_3$) δ 8.65-8.61 (m, 3H), 7.72-7.63 (m, 3H), 7.44-7.35 (m, 3H), 2.60 (t, J=7.2 Hz, 8H), 2.33 (br.s, 1H), 1.76-1.57 (m, 8H), 1.64 (s, 6H), 1.48-1.34 (m, 4H), 1.20-1.10 (m, 21H), 1.00 (t, J=7.5 Hz, 6H), 0.95 (t, J=7.8 Hz, 6H).

$^{13}$C NMR (75 MHz, CDCl$_3$) δ 152.65, 152.37, 152.15, 142.09, 142.08, 141.95, 138.63, 138.09, 138.01, 131.29,

[Chemical Formula 34]

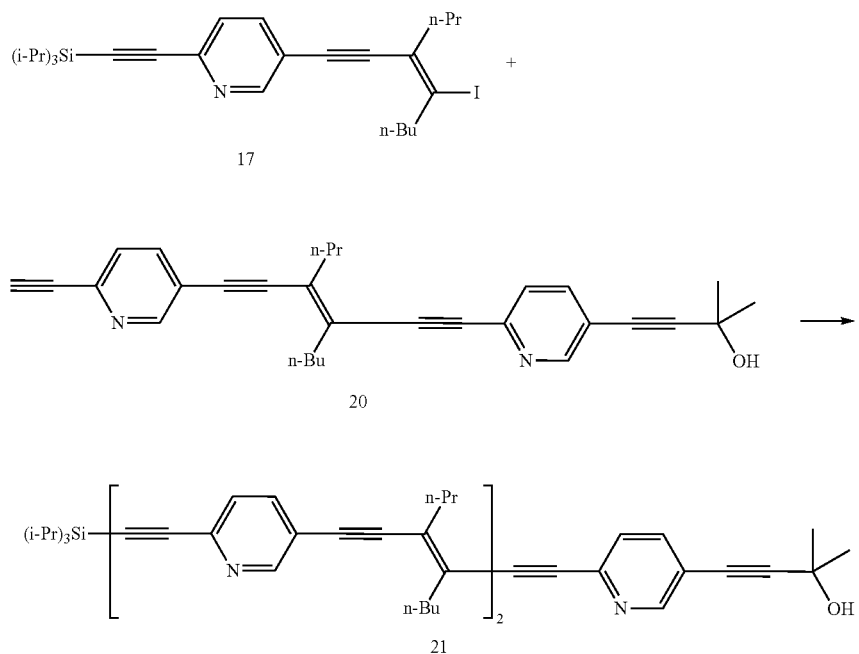

(wherein n-Pr represents an n-propyl group, i-Pr represents an i-propyl group and n-Bu represents an n-butyl group).

The trans-pyridylodo-enyne compound 17 (84.0 mg, 0.156 mmols) obtained in Example 6-(d) was dissolved in degassed THF (0.5 ml), to which tetrakistriphenylphosphine palladium (6.07 mg, 0.00525 mmols), cuprous iodide (2.00 mg, 0.0105 mmols) and diethylamine (0.05 ml) were added at room temperature, followed by dropping a THF (1.5 ml) solution of the crude product of trans-(pyridine-enediyne) compound 20 obtained in Example 7.

The reaction solution was agitated as it is at room temperature overnight, to which water was added at 0° C. for quenching.

131.24, 130.65, 130.63, 127.09, 126.62, 126.51, 119.64, 119.46, 118.96, 105.68, 99.21, 98.16, 97.97, 95.90, 95.87, 94.10, 93.92, 93.79, 90.88, 90.61, 78.70, 65.44, 36.92, 36.89, 34.74, 34.71, 31.24, 30.61 (×2), 22.08 (×2), 21.70 (×2), 18.51, 13.81 (×2), 13.47 (×2), 11.10.

IR (KBr) 3427, 2925, 2862, 2198, 1654, 1540, 1465, 1365, 1255, 1018, 836, 676 cm$^{-1}$.

UV/Vis (CHCl$_3$): λ$_{abs}$ (ε) [nm]=336 (49 800), 354 (70 500), 385 (94 200), 415 (55 700).

MALDI-TOF-MS (DHB): 839.6 (calculated for C$_{57}$H$_{69}$N$_3$O$_1$Si: 839.5).

Anal. Calculated for C$_{57}$H$_{69}$N$_3$OSi: C, 81.48; H, 8.28. Found: C, 81.37; H, 8.42.

Example 9

Synthesis of Trans-(Pyridine-Enediyne)Dimer Compound 22

[Chemical Formula 35]

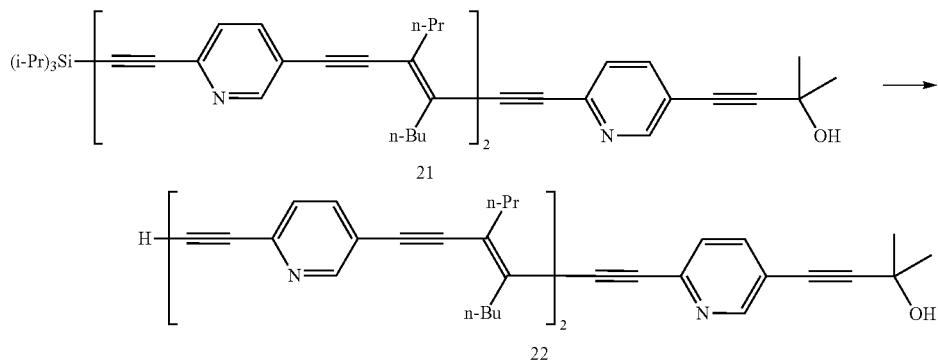

(wherein n-Pr represents an n-propyl group, i-Pr represents an i-propyl group, and n-Bu represents an n-butyl group).

Using the trans-silylated (pyridine-enediyne) dimer compound 21 obtained in Example 8, a trans-(pyridine-enediyne) dimer compound 22 was obtained in the same manner as in Example 7. The crude product is confirmed with NMR and used as it is for subsequent reaction.

Example 10

Synthesis of Trans-Silylated (Pyridine-Enediyne) Trimer Compound 23

[Chemical Formula 36]

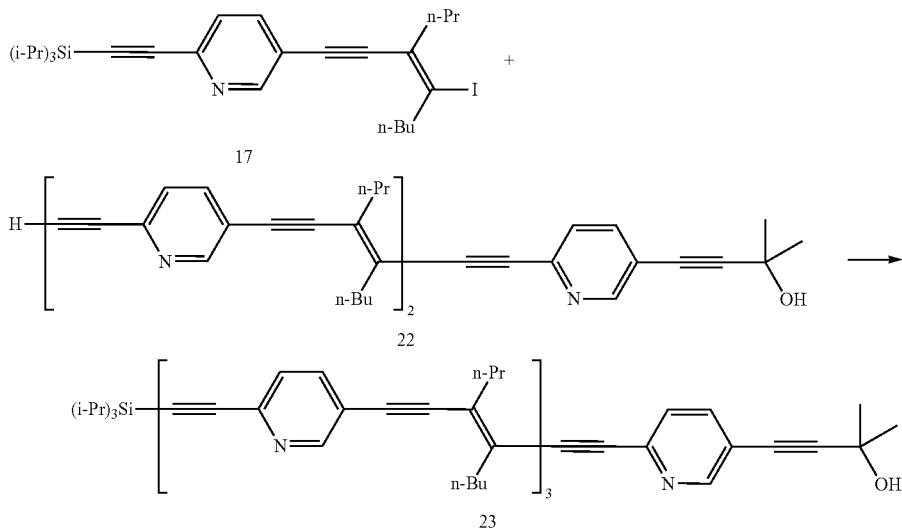

(wherein n-Pr represents an n-propyl group, i-Pr represents an i-propyl group, and n-Bu represents an n-butyl group).

Using the trans-(pyridine-enediyne) dimer compound 22 obtained in Example 9, a trans-silylated (pyridine-enediyne) trimer compound 23 was obtained at a two-step yield of 69% in the same manner as in Example 8.

m.p.=173-175° C.

$^1$H NMR (300 MHz, CDCl$_3$) δ 8.66-8.61 (m, 4H), 7.70-7.65 (m, 4H), 7.44-7.37 (m, 4H), 2.64-2.57 (m, 12H), 2.13 (br.s, 1H), 1.76-1.58 (m, 12H), 1.64 (s, 6H), 1.48-1.36 (m, 6H), 1.20-1.10 (m, 21H), 1.03-0.92 (m, 18H).

$^{13}$C NMR (75 MHz, CDCl$_3$) δ 152.48, 152.22 (×2), 151.99, 141.91, 141.89, 141.88, 141.79, 138.53, 137.99 (×2), 137.91, 131.18 (×2), 131.12, 130.56, 130.53, 130.51, 127.00, 126.54 (×2), 126.43, 119.53, 119.36, 119.35, 118.91, 105.56, 99.33, 98.14, 98.07, 97.87, 95.90, 95.83, 95.80, 94.04, 93.88 (×2), 93.72, 90.83 (×2), 90.58, 78.58, 65.35, 36.96 (×2), 36.92, 34.78 (×3), 31.30, 30.66 (×3), 22.17 (×3), 21.79 (×3), 18.60, 13.93 (×3), 13.58 (×3), 11.18.

IR (KBr) 3428, 2925, 2861, 2199, 1465, 1366, 1260, 1099, 1019, 835, 670 cm$^{-1}$.

UV/Vis (CHCl$_3$): λ$_{abs}$ (ε) [nm]=335 (74 300), 373 (141 000), 394 (158 000), 415 (122 000).

MALDI-TOF-MS (DHB): 1089.7 (calculated for C$_{75}$H$_{88}$N$_4$OSi: 1088.7).

Anal. Calculated for $C_{75}H_{88}N_4OSi$: C, 82.67; H, 8.14. Found: C, 82.86; H, 8.06.

Example 11

Synthesis of Cyanothienyl(Thiophene-Enediyne) Compound 25

[Chemical Formula 37]

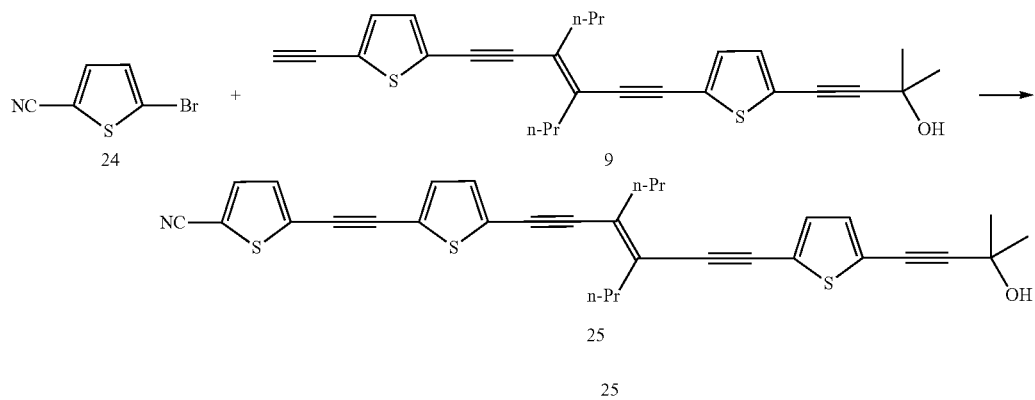

(wherein n-Pr represents an n-propyl group).

Using bromocyanothiophene 24, a cyanothienyl (thiophene-enediyne) compound 25 was obtained at a two-step yield of 57% in the same manner as in Example 3.

$^1$H NMR (300 MHz, CDCl$_3$) δ 7.52 (d, J=3.9 Hz, 1H), 7.221 (d, J=3.9 Hz, 1H), 7.216 (d, J=3.9 Hz, 1H), 7.09 (d, J=3.9 Hz, 1H), 7.05 (d, J=3.9 Hz, 1H), 7.03 (d, J=3.9 Hz, 1H), 2.51 (d, J=7.2 Hz, 4H), 1.71-1.51 (m, 4H), 0.99 (t, J=7.2 Hz, 6H).

UV/Vis (CHCl$_3$): $λ_{max}$ [nm]=372.
$λ_{em}$ [nm]=475.

Example 12

Synthesis of bis[silylated(thienyl-enediyne)]benzothiadiazole compound 30

(a) Synthesis of Disilylated Thienylenediyne Compound 27

[Chemical Formula 38]

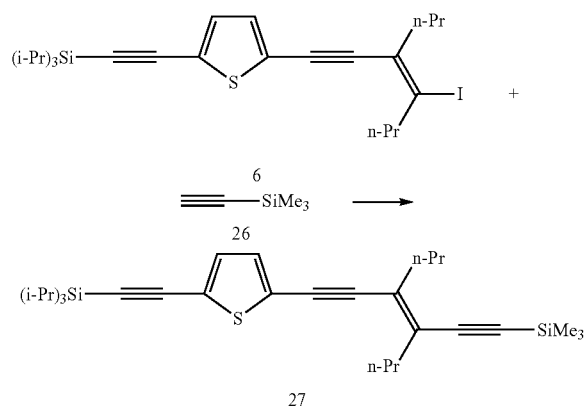

(wherein Me represents a methyl group, n-Pr represents an n-propyl group, and i-Pr represents an i-propyl group).

Using an ethynyltrimethylsilane 26, a disilylated thienylenediyne compound 27 was obtained at a yield of 95% in the same manner as in Example 5.

$^1$H NMR (300 MHz, CDCl$_3$) δ 7.07 (d, J=3.9 Hz, 1H), 6.99 (d, J=3.9 Hz, 1H), 2.46 (t, J=7.4 Hz, 2H), 2.40 (t, J=7.5 Hz, 2H), 1.63-1.55 (m, 4H), 1.18-1.02 (m, 21H), 0.93 (t, J=6.9 Hz, 6H), 0.20 (s, 9H).

(b) Synthesis of Silylated Thienylenediyne Compound 28

[Chemical Formula 39]

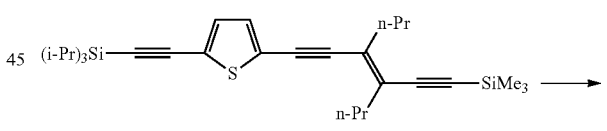

(wherein Me represents a methyl group, n-Pr represents an n-propyl group, and i-Pr represents an i-propyl group).

The thus obtained disilylated thienylenediyne compound 27 (0.934 mg, 1.89 mmols) was dissolved in methanol/THF/water (3.8 ml/1.9 ml/3 droplets), to which potassium carbonate (523 mg, 3.78 mmols) was added, followed by agitation at room temperature for 1 hour.

After confirmation of disappearance of the starting disilylated thienylenediyne compound 27 with TLC, ether and hexane were added to the reaction solution for extraction, and the resulting organic phase was dried over anhydrous magnesium sulfate.

After filtration, the crude product obtained by concentrating the filtrate under reduced pressure was confirmed with NMR and used as it is for subsequent reaction.

$^1$H NMR (300 MHz, CDCl$_3$) δ 7.08 (d, J=3.9 Hz, 1H), 7.00 (d, J=3.9 Hz, 1H), 3.46 (s, 1H), 2.48 (t, J=7.5 Hz, 2H), 2.43 (t, J=7.8 Hz, 2H), 1.66-1.52 (m, 4H), 1.17-1.03 (m, 21H), 0.96 (t, J=7.2 Hz, 6H).

(c) Synthesis of bis[silylated(thienyl-enediyne)]benzothiadiazole compound 30

After filtration, the crude product obtained by concentration of the filtrate under reduced pressure was purified with silica gel column chromatography (hexane/ethyl acetate=20/1) to obtain bis[silylated(thienyl-enediyne)]-benzothiadiazole compound 30 at a two-step yield of 94%.

$^1$H NMR (300 MHz, CDCl$_3$) δ 7.64 (s, 2H), 7.10 (d, J=3.6 Hz, 2H), 7.04 (d, J=3.6 Hz, 2H), 2.72 (t, J=7.2 Hz, 4H), 2.60 (t, J=7.5 Hz, 4H), 1.82-1.64 (m, 8H), 1.16-0.97 (m, 54H).

UV/Vis (CHCl$_3$): λ$_{max}$ [nm]=371, 473.

λ$_{em}$ (nm)=569.

[Chemical Formula 40]

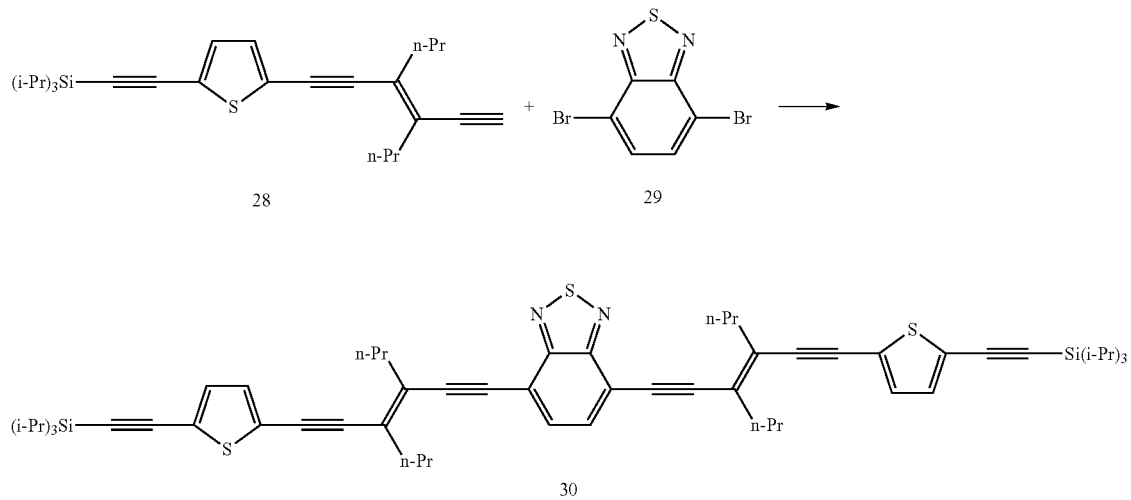

(wherein n-Pr represents an n-propyl group, and i-Pr represents an i-propyl group).

Dibromothiadiazole 29 (118 mg, 0.401 mmols) were dissolved in degassed chloroform (1 ml), to which tetrakistriphenylphosphine palladium (116 mg, 0.100 mmol), cuprous iodide (38.2 mg, 0.201 mmols) and diisopropylamine (1.3 ml) were added at room temperature, followed by dropping of a degassed chloroform (4 ml) solution of the silylated thienyl-enedyne compound 28 (372 mg, 0.882 mmols) obtained above.

The reaction solution was agitated under reflux while heating for 24 hours, and was quenched by addition of water thereto at room temperature.

After extraction from the aqueous phase with chloroform and washing with a saturated saline solution, the resulting organic phase was dried over anhydrous magnesium sulfate.

Example 13

Synthesis of di(thienyl-enediyne)thieno[3,4-b]pyradine compound 36

(a) Synthesis of Silythienyl-Enediyne Compound 33

[Chemical Formula 41]

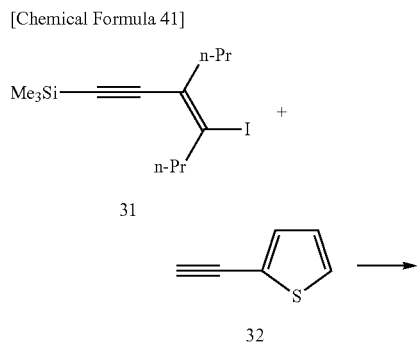

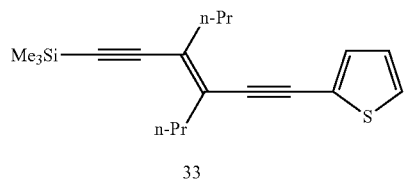

33

(wherein Me represents a methyl group, and n-Pr represents an n-propyl group).

After addition of tetrakistriphenylphosphine palladium (1118 mg, 0.102 mmols), cuprous iodide (38.8 mg, 0.204 mmols) and diethylamine (2.6 ml) to a THF (2 ml) solution of the trans-iodo-enyne compound 31 (0.340 mg, 1.02 mmols), a THF (8 ml) of ethynyl thiophene 32 (132 mg, 1.22 mmols) was dropped.

The reaction solution was agitated at room temperature overnight, after which water was added to the reaction solution for quenching.

After extraction from the aqueous phase with ether and washing with a saturated saline solution, the resulting organic phase was dried over anhydrous magnesium sulfate.

After filtration, the filtrate was concentrated under reduced pressure to obtain a silylthienyl-enediyne compound 33 at a yield of 55% (174 mg).

$^1$H NMR (300 MHz, CDCl$_3$) δ 7.27 (dd, J=1.2, 5.1 Hz, 1H), 7.18 (dd, J=1.2, 3.6 Hz, 1H), 6.99 (dd, J=3.6, 5.1 Hz, 1H), 2.48 (t, J=7.7 Hz, 2H), 2.43 (t, J=7.8 Hz, 2H), 1.70-1.56 (m, 4H), 0.98 (t, J=7.2 Hz, 6H), 0.22 (s, 9H).

$^{13}$C NMR (75 MHz, CDCl$_3$) δ −0.141, 13.54 (×2), 21.59, 21.66, 36.76, 36.82, 91.69, 92.98, 103.98, 104.65, 123.71, 127.23, 127.36, 129.81, 130.47, 131.49.

(b) Synthesis of Thienyl-Enediyne Compound 34

[Chemical Formula 42]

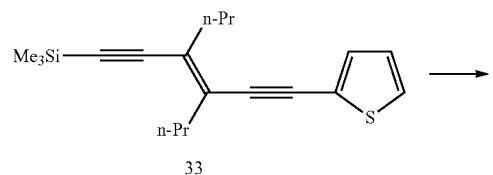

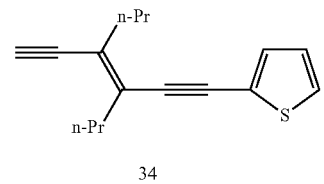

34

(wherein Me represents a methyl group, and n-Pr represents an n-propyl group).

Using the silylthienyl-enediyne compound 33 obtained above, a thienyl-enediyne compound 34 was obtained in the same manner as in Example 12-(b). The resulting crude product was confirmed with NMR and used as it is for subsequent reaction.

$^1$H NMR (300 MHz, CDCl$_3$) δ 7.28 (dd, J=1.2, 5.1 Hz, 1H), 7.20 (dd, J=1.2, 3.6 Hz, 1H), 7.00 (dd, J=3.6, 5.1 Hz, 1H), 3.44 (s, 1H), 2.56-2.43 (m, 4H), 1.72-1.57 (m, 4H), 0.98 (t, J=6.9 Hz, 6H).

(c) Synthesis of di(thienyl-enediyne)thieno[3,4-b]pyradine compound 36

[Chemical Formula 43]

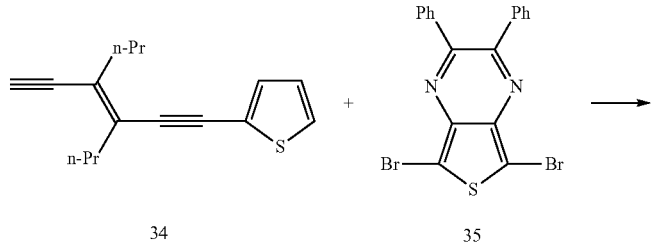

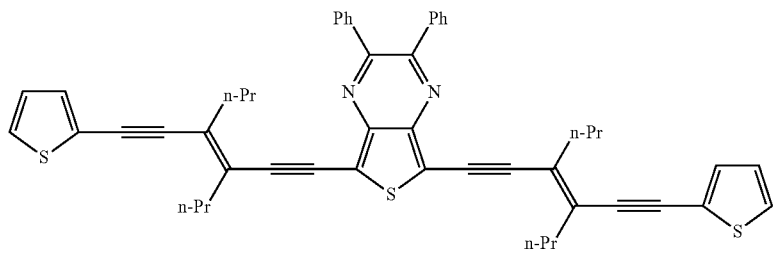

36

(wherein n-Pr represents an n-propyl group).

Using the thienyl-enediyne compound 34 and dibromothieno[3,4-b]pyrazine 35, a di(thienyl-enedyne)-thieno[3,4-b]pyrazine compound 36 was obtained at a two-step yield of 72% in the same manner as in Example 12-(c).

$^1$H NMR (300 MHz, CDCl$_3$) δ 7.60-7.24 (m, 12H), 7.23 (dd, J=0.9, 3.6 Hz, 2H), 7.02 (dd, J=3.6, 5.4 Hz, 2H), 2.71 (t, J=7.5 Hz, 4H), 2.62 (t, J=7.5 Hz, 4H), 1.87-1.65 (m, 8H), 1.12-0.92 (m, 12H).

UV/Vis (CHCl$_3$): λ$_{max}$ [nm]=372, 541.

λ$_{em}$ (nm)=647.

Example 14

Synthesis of Silylated (Pyridine-Enyne) Compound 43

(a) Synthesis of Alkenylalkynylpyridine Compound 38

[Chemical Formula 44]

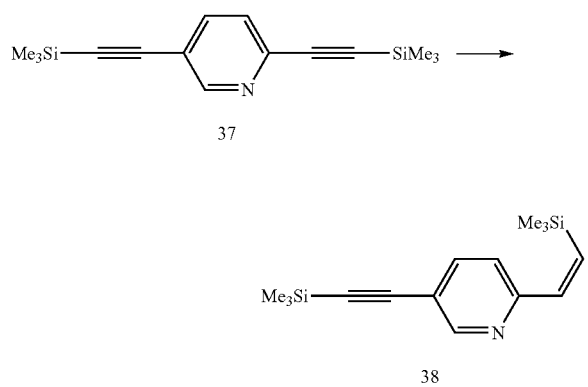

(wherein Me represents a methyl group).

Tetra-i-propoxy titanium (7.31 ml, 24.8 mmols) was added to an ether (250 ml) solution of dialkynyl pyridine compound 37 (6.71 g, 24.8 mmols), which was subsequently cooled to −78° C., followed by gradual addition of i-propylmagnesium chloride (1.94 M/ether solution, 28.0 ml, 54.5 mmols).

The temperature was raised to −50° C. in 1 hour, at which agitation was continued for 4 hours.

Water was added to the reaction solution and, after agitation for 30 minutes, was subjected to celite filtration.

After filtration, the crude product obtained by concentrating the filtrate under reduced pressure was purified with silica gel column chromatography (hexane/ether=100/1) to obtain an alkenylalkynyl pyridine compound 38 at a yield of 95%.

$^1$H NMR (300 MHz, CDCl$_3$) δ 8.66 (d, J=1.5 Hz, 1H), 7.67 (dd, J=2.1, 8.1 Hz, 1H), 7.17 (d, J=14.4 Hz, 1H), 7.09 (d, J=8.1 Hz, 1H), 6.13 (d, J=14.4 Hz, 1H), 0.28 (s, 9H), 0.190 (s, 9H).

$^{13}$C NMR (75 MHz, CDCl$_3$) δ −0.136, 0.562, 98.24, 102.11, 118.22, 122.62, 138.91, 139.85, 142.94, 151.33, 154.99.

IR (neat): 2957.30, 2159.40, 1585.68, 1539.40, 1474.79, 1363.43, 1251.09, 1023.53, 839.37 cm$^{-1}$.

(b) Synthesis of Dibromoralkynylpyridine Compound 39

[Chemical Formula 45]

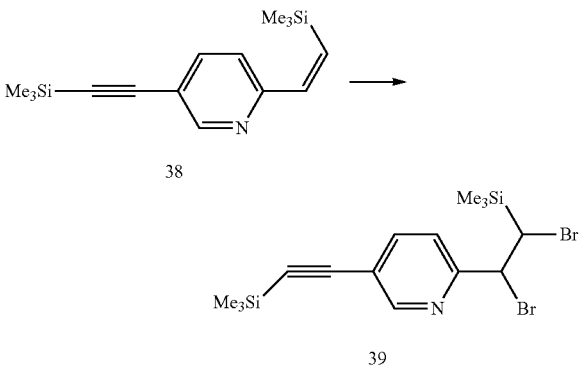

(wherein Me represents a methyl group).

A dichloromethane (36 ml) solution of the thus obtained alkenylalkynyl pyridine compound 38 (4.91 g, 17.8 mmols) was cooled down to −78° C., in which a dichloromethane (11 ml) solution of bromine (1.15 ml, 22.5 mmols) was dropped, followed by agitation for 10 minutes.

Methanol (200 ml) and sodium sulfite (9 g) were added to the reaction solution for quenching. After the quenching, a 10% sodium sulfite aqueous solution was further added, and the resulting aqueous phase was extracted with pentane. Further, the aqueous solution was further extracted with pentane/ether (1/1), and a combined organic phase was washed with water, followed by drying the organic phase over anhydrous magnesium sulfate.

After filtration, the crude product obtained by concentrating the filtrate under reduced pressure was confirmed with NMR and used for subsequent reaction as it is.

$^1$H NMR (300 MHz, CDCl$_3$) δ 8.61 (dd, J=0.9, 2.1 Hz, 1H), 7.74 (dd, J=2.1, 8.1 Hz, 1H), 7.44 (dd, J=0.9, 8.1 Hz, 1H), 5.35 (d, J=8.4 Hz, 1H), 4.06 (d, J=8.4 Hz, 1H), 0.263 (s, 9H), 0.024 (s, 9H).

(c) Synthesis of Alkynylbromoalkenyl Pyridine Compound 40

[Chemical Formula 46]

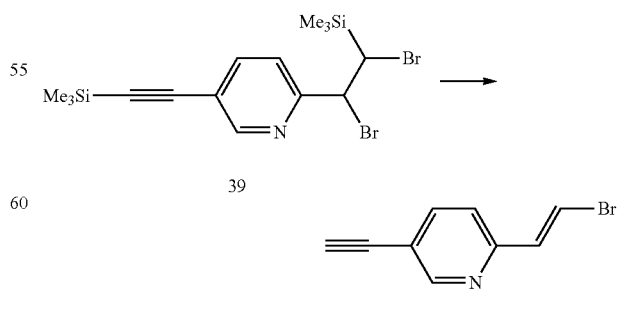

(wherein Me represents a methyl group).

Sodium methoxide (1.0 M/methanol solution, 26.7 ml, 26.7 mmols) was added to a methanol (180 ml) and THF (45 ml) solution of the crude product of the thus obtained dibromoalkynyl pyridine compound 39 at 0° C. and agitated for 1 hour. The temperature was raised to room temperature, followed by agitation for 2 hours.

The reaction solution was diluted with pentane and water and, after funnel separation, the organic phase was dried over anhydrous magnesium sulfate.

After filtration, the crude product obtained by concentrating the filtrate under reduced pressure was purified with silica gel column chromatography (hexane/ether=50/1) to obtain an alkynylbromoalkenyl pyridine compound 40 at a two-step yield of 66%.

$^1$H NMR (300 MHz, CDCl$_3$) δ 8.63-8.62 (m, 1H), 7.72 (dd, J=2.1, 8.1 Hz, 1H), 7.44 (d, J=13.8 Hz, 1H), 7.12 (d, J=13.8 Hz, 1H), 7.11 (dd, J=0.9, 8.1 Hz, 1H), 3.26 (s, 1H)

(d) Synthesis of Silylalkynylbromoalkenyl Pyridine Compound 41

[Chemical Formula 47]

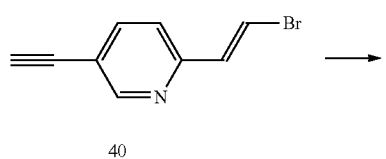

(wherein Me represents a methyl group).

The alkynylbromoalkenyl pyridine compound 41 (1.51 g, 7.26 mmols) obtained above was dissolved in THF (24 ml) and cooled down to −78° C. Sodium bis(trimethylsilyl)amide (1.0 M/THF solution, 9.44 ml, 9.44 mmols) was dropped and agitated for 2 hours. Chlorotrimethylsilane (1.38 ml, 10.9 mmols) was added to the reaction solution at the temperature, after which the temperature was raised to room temperature, followed by overnight agitation.

Water was added to the reaction solution at 0° C. for quenching. Extraction from the aqueous phase was carried out with use of ether, followed by washing with water and drying the organic phase over anhydrous magnesium sulfate.

After filtration, a crude product obtained by concentrating the filtrate under reduced pressure was purified with silica gel column chromatography (hexane/ether=100/1) to obtain a silylalkynylbromoalkenyl pyridine compound 41 at a yield of 86%.

$^1$H NMR (300 MHz, CDCl$_3$) δ 8.58 (d, J=1.8 Hz, 1H), 7.66 (dd, J=2.1, 8.4 Hz, 1H), 7.40 (d, J=13.8 Hz, 1H), 7.09 (d, J=13.8 Hz, 1H), 7.06 (d, J=7.8 Hz, 1H), 0.25 (s, 9H)

$^{13}$C NMR (75 MHz, CDCl$_3$) δ 0.23, 99.07, 101.54, 113.98, 119.08, 120.77, 135.94, 139.44, 152.52, 152.75.

IR (neat): 2959.23, 2159.40, 1472.87, 1249.65, 1162.87, 1022.57, 935.79, 843.22.

(e) Synthesis of Silylated (Pyrdine-Enyne) Compound 43

[Chemical Formula 48]

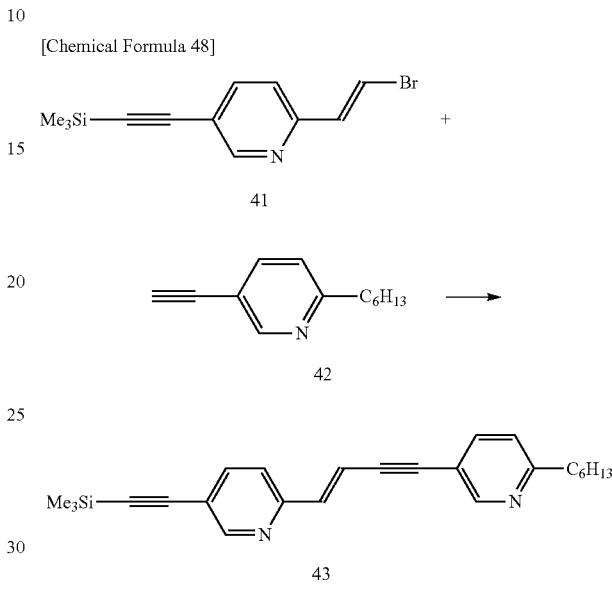

(wherein Me represents a methyl group).

Dichlorobistriphenylphosphine palladium (47.0 mg, 0.0667 mmols), cuprous iodide (25.0 mg, 0.133 mmols) and diethylamine (0.690 ml, 6.67 mmols) were added to a degassed THF (2 ml) solution of the silylalkynylbromolakenyl pyridine compound 41 (0.373 g, 1.33 mmols) obtained above at room temperature, in which a degassed THF (10 ml) solution of a ethynyl pyridine compound 42 (0.274 g, 1.47 mmols) was dropped.

The reaction solution was agitated for 2 hours at room temperature, to which water was added for quenching.

After extraction with ether from the aqueous solution and washing with a saturated saline solution, the organic phase was dried over anhydrous magnesium sulfate.

After filtration, a crude product obtained by concentrating the filtrate under reduced pressure was purified with silica gel column chromatography (hexane/ethyl acetate=100/1) to obtain a silylated (pyridine-enyne) compound 43 at a yield of 78% (0.403 g).

$^1$H NMR (300 MHz, CDCl$_3$) δ 8.632 (s, 1H), 8.626 (s, 1H), 7.69 (d, J=2.1, 8.1 Hz, 1H), 7.66 (dd, J=2.1, 8.1 Hz, 1H), 7.19 (d, J=8.1 Hz, 1H), 7.12 (d, J=8.1 Hz, 1H), 7.04 (d, J=15.6 Hz, 1H), 6.97 (d, J=15.6 Hz, 1H), 2.79 (t, J=7.8 Hz, 2H), 1.79-1.64 (m, 2H), 1.42-1.23 (m, 6H), 0.876 (t, J=6.9 Hz, 3H), 0.265 (s, 9H).

$^{13}$C NMR (75 MHz, CDCl$_3$) δ −0.331, 13.91, 22.44, 28.91, 29.57, 31.57, 38.34, 91.10, 91.41, 99.39, 101.81, 113.33, 117.39, 119.47, 121.56, 122.20, 138.79, 139.41, 139.85, 151.88, 152.81, 153.03, 162.36.

UV/Vis (CHCl$_3$): λ$_{max}$ [nm](ε [M$^{-1}$ cm$^{-1}$])=345 (56 800).

Example 15

Synthesis of (Pyridine-Enyne) Compound 44

[Chemical Formula 49]

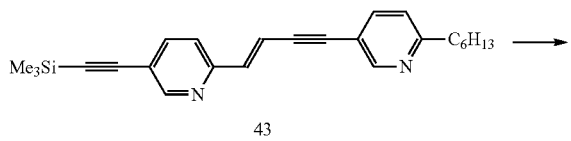

43

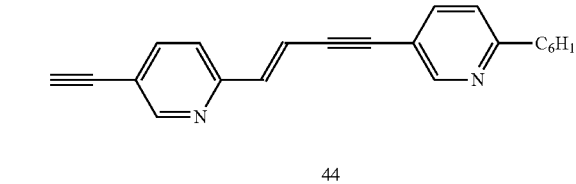

44

(wherein Me represents a methyl group).

Using the thus obtained silylated (pyridine-enyne) compound 43 (0.390 g, 1.01 mmols), a (pyridine-enyne) compound 44 was obtained in the same manner as in Example 2.

The resulting crude product was confirmed with NMR and used as it is for subsequent reaction.

$^1$H NMR (300 MHz, CDCl$_3$) δ 8.67 (d, J=2.4 Hz, 1H), 8.63 (d, J=2.4 Hz, 1H), 7.73 (dd, J=2.4, 8.1 Hz, 1H), 7.66 (dd, J=2.4, 8.1 Hz, 1H), 7.21 (d, J=8.1 Hz, 1H), 7.12 (d, J=8.1 Hz, 1H), 7.06 (d, J=15.9 Hz, 1H), 6.99 (d, J=15.9 Hz, 1H), 3.27 (s, 1H), 2.79 (t, J=7.8 Hz, 2H), 1.78-1.62 (m, 2H), 1.42-1.23 (m, 6H), 0.875 (t, J=6.9 Hz, 3H).

Example 16

Synthesis of Silylated (Pyridine-Enyne) Dimer Compound 45

[Chemical Formula 50]

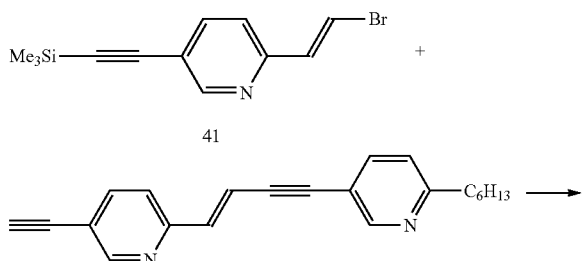

41

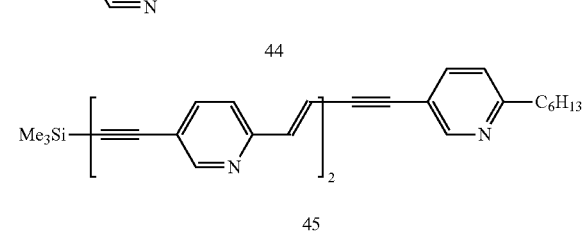

44

45

(wherein Me represents a methyl group).

The silylalkynylbromoalkenyl pyridine compound 41 (0.423 g, 1.51 mmols) obtained in Example 14-(d) was dissolved in degassed THF (3 ml), to which tetrakistriphenylphosphine palladium (58.3 mg, 0.0505 mmols), cuprous iodide (10.0 mg, 0.0505 mmols) and diethylamine (0.522 ml, 5.05 mmols) were added at room temperature, in which a degassed THF (10 ml) solution of the crude product of the (pyridine-enyne) compound 44 obtained above was dropped.

The reaction solution was agitated at room temperature for 2 hours, after which water was added to the reaction solution for quenching.

After extraction with chloroform from an aqueous phase and washing with a saturated saline solution, the resulting organic phase was dried over anhydrous magnesium sulfate.

After filtration, the crude product obtained by concentrating the resulting filtrate under reduced pressure was purified by recrystallization (hexane-chloroform) to obtain silylated (pyridine-enyne) dimer compound 45 at a two-step yield of 75% (0.390 g).

$^1$H NMR (300 MHz, CDCl$_3$) δ 8.67 (d, J=2.1 Hz, 1H), 8.64 (d, J=2.1 Hz, 2H), 7.72 (dd, J=2.1, 8.1 Hz, 1H), 7.70 (dd, J=2.1, 8.1 Hz, 1H), 7.67 (dd, J=2.1, 8.4 Hz, 1H), 7.23 (d, J=8.1 Hz, 1H), 7.20 (d, J=8.4 Hz, 1H), 7.13 (d, J=8.1 Hz, 1H), 7.07 (d, J=15.9 Hz, 1H), 7.06 (d, J=15.9 Hz, 1H), 6.99 (d, J=15.9 Hz, 2H), 2.79 (t, J=7.5 Hz, 2H), 1.78-1.62 (m, 2H), 1.38-1.22 (m, 6H), 0.876 (t, J=6.9 Hz, 3H), 0.267 (s, 9H).

$^{13}$C NMR (75 MHz, CDCl$_3$) δ −0.346, 13.90, 22.43, 28.90, 29.55, 31.55, 38.32, 91.17, 91.37, 91.53, 93.02, 99.51, 101.75, 113.05, 113.34, 117.37, 119.50, 119.59, 121.69, 121.78, 122.20, 138.78, 139.00, 139.41, 139.82, 140.29, 151.86, 152.49, 152.81, 152.84, 153.01, 162.34.

UV/Vis (CHCl$_3$): λ$_{max}$ [nm] (ϵ[M$^{-1}$ cm$^{-1}$])=376 (74 800).

Example 17

Synthesis of (Pyridine-Enyne)Dimer Compound 46

[Chemical Formula 51]

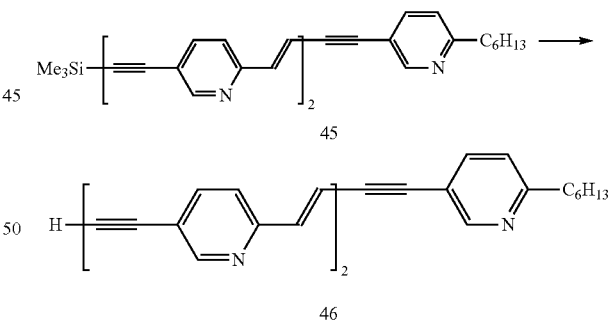

(wherein Me represents a methyl group).

Using the silylated (pyridine-enyne) dimer compound 45 (93.9 mg, 0.183 mmols) obtained in Example 16, (pyridine-enyne) dimer compound 46 was obtained in the same manner as in Example 2.

The resulting crude product was confirmed with NMR and used as it is for subsequent reaction.

NMR (300 MHz, CDCl$_3$) δ 8.69-8.62 (m, 3H), 7.74 (dd, J=2.4, 8.1 Hz, 1H), 7.72 (dd, J=2.1, 8.1 Hz, 1H), 7.67 (dd, J=2.1, 8.1 Hz, 1H), 7.23 (d, J=8.1 Hz, 1H), 7.22 (d, J=8.1 Hz, 1H), 7.13 (d, J=8.1 Hz, 1H), 7.12-7.04 (m, 2H), 7.01 (d,

J=15.6 Hz, 1H), 7.00 (d, J=15.3 Hz, 1H), 3.28 (s, 1H), 2.79 (t, J=7.8 Hz, 2H), 1.79-1.60 (m, 1H), 1.41-1.22 (m, 6H), 0.877 (t, J=6.9 Hz, 3H).

Example 18

Synthesis of Silylated (Pyridine-Enyne) Trimer Compound 47

[Chemical Formula 52]

(wherein Me represents a methyl group).

Using the (pyridine-enyne) dimer compound 46 obtained in Example 17, silylated (pyridine-enyne) trimer compound 47 was obtained in the same manner as in Example 16 at a two-step yield of 42% (49.0 mg).

$^1$H NMR (300 MHz, CDCl$_3$) δ 8.69-8.65 (m, 2H), 8.64-8.61 (m, 2H), 7.76-7.64 (m, 4H), 7.27-6.96 (m, 10H), 2.79 (t, J=7.8 Hz, 2H), 1.78-1.61 (m, 2H), 1.38-1.20 (m, 6H), 0.93-0.84 (m, 3H), 0.269 (s, 1H).

UV/Vis (CHCl$_3$): λ$_{max}$ [nm] (ϵ[M$^{-1}$ cm$^{-1}$])=394 (80 900).

Example 19

Synthesis of Cyanopyridyl (Pyridine-Enyne) Compound 49

[Chemical Formula 53]

Using bromocyano pyridine 48, cyanopyridyl(pyrdine-enyne) compound 49 was obtained in the same manner as in Example 16 at a two-step yield of 77%.

$^1$H NMR (300 MHz, CDCl$_3$) δ 8.89 (dd, J=0.9, 2.1 Hz, 1H), 8.78 (d, J=2.1 Hz, 1H), 8.66-8.63 (m, 1H), 7.97 (dd, J=2.1, 8.1 Hz, 1H), 7.85 (dd, J=2.1, 8.1 Hz, 1H), 7.69-7.61 (m, 2H), 7.32-7.22 (m, 1H), 7.13 (d, J=8.1 Hz, 1H), 7.15-6.96 (m, 2H), 2.80 (t, J=7.5 Hz, 2H), 1.78-1.64 (m, 2H), 1.45-1.15 (m, 6H), 0.868 (t, J=7.2 Hz, 3H).

$^{13}$C NMR (75 MHz, CDCl$_3$) δ 13.89, 22.40, 28.85, 29.30, 31.51, 38.32, 90.72, 91.01, 91.39, 92.09, 108.80, 114.40, 116.25, 117.42, 117.25, 121.85, 122.27, 126.95, 138.84, 139.47, 139.42, 139.75, 146.14, 151.89, 152.76, 152.90, 154.26, 162.46.

UV/Vis (CHCl$_3$): λ$_{max}$ [nm]=366.

Example 20

Synthesis of Pyridyl Silylated (Pyridine-Enyne) Compound 51

[Chemical Formula 54]

(wherein Me represents a methyl group).

Using ethynyl pyridine 50, pyridyl silylated (pyridine-enyne) compound 51 was obtained in the same manner as in Example 14-(e) at a yield of 73%.

$^1$H NMR (300 MHz, CDCl$_3$) δ 8.71 (br.s, 1H), 8.62 (d, J=2.1 Hz, 1H), 8.52 (br, s, 1H), 7.74 (d, J=7.8 Hz, 1H), 7.67 (dd, J=2.1, 8.1 Hz, 1H), 7.25 (dd, J=5.1, 7.8 Hz, 1H), 7.17 (d, J=8.1 Hz, 1H), 7.04 (d, J=15.9 Hz, 1H), 6.96 (d, J=15.9 Hz, 1H), 0.250 (s, 9H).

$^{13}$C NMR (75 MHz, CDCl$_3$) δ −0.369, 90.81, 91.82, 99.45, 101.71, 112.98, 119.55, 120.40, 121.64, 123.08, 138.49, 139.38, 140.26, 148.78, 152.37, 152.75 (×2).

Example 21

Synthesis of Pyridyl (Pyridine-Enyne) Compound 52

[Chemical Formula 55]

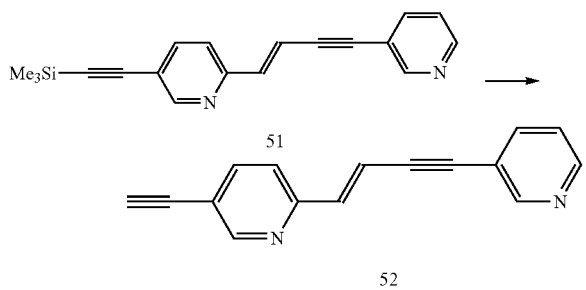

(wherein Me represents a methyl group).

Using the pyridyl silylated (pyridine-enyne) compound 51 obtained in Example 20, pyridyl (pyridine-enyne) compound 52 was obtained in the same manner as in Example 2.

The resulting crude product was confirmed with NMR and used as it is for subsequent reaction.

$^1$H NMR (300 MHz, CDCl$_3$) δ 8.74-8.71 (m, 1H), 8.69-8.66 (m, 1H), 8.56-8.53 (m, 1H), 7.80-7.71 (m, 2H), 7.31-7.21 (m, 2H), 7.08 (d, J=15.9 Hz, 1H), 7.00 (d, J=15.9 Hz, 1H), 3.28 (s, 1H).

Example 22

Synthesis of Alkoxypyridyl (Pyridine-Enyne) Compound 54

[Chemical Formula 56]

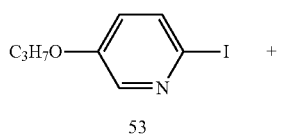 +

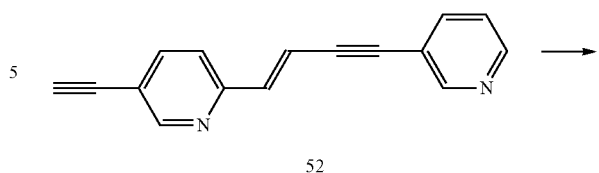

(wherein Me represents a methyl group).

Using iodopropoxy pyridine compound 53 and the alkoxypyridyl (pyridine-enyne) compound 52 obtained in Example 21, alkoxypyridyl (pyridine-enyne) 54 was obtained in the same manner as in Example 16 at a two-step yield of 65%.

$^1$H NMR (300 MHz, CDCl$_3$) δ 8.79-8.77 (m, 1H), 8.74-8.71 (m, 1H), 8.55 (dd, J=1.8, 5.1 Hz, 1H), 8.23 (dd, J=1.8, 4.2 Hz, 1H), 7.84 (dd, J=2.1, 8.4 Hz, 1H), 7.78 (dd, J=1.8, 8.1 Hz, 1H), 7.32-7.21 (m, 4H), 7.10 (d, J=15.6 Hz, 1H), 7.02 (d, J=15.6 Hz, 1H), 4.05 (t, J=6.3 Hz, 2H), 1.98-1.86 (m, 2H), 1.13 (t, J=7.5 Hz, 3H).

$^{13}$C NMR (75 MHz, CDCl$_3$) δ 10.38, 22.38, 70.25, 89.79, 90.39, 90.93, 91.90, 113.09, 118.96, 119.38, 120.41, 121.95, 123.12, 124.15, 133.25, 138.59, 139.33, 140.32, 141.94, 148.85, 152.41, 152.74, 153.03, 156.87.

UV/Vis (CHCl$_3$): λ$_{max}$ [nm]=339.

Example 23

Synthesis of bis[silylated ethynyl(thienyl-enediyne)]benzene compound 56

[Chemical Formula 57]

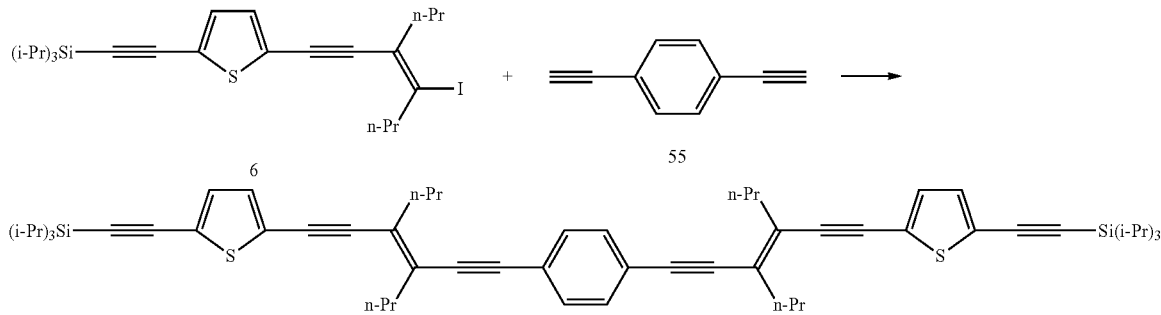

(wherein n-Pr represents an n-propyl methyl group and i-Pr represents an i-propyl group).

The trans-thienyliodo-enyne compound 6 (311 mg, 0.594 mmols) was dissolved in degassed THF (1.3 ml), to which tetrakistriphenylphosphine palladium (11.5 mg, 0.00991 mmols), cuprous iodide (3.77 mg, 0.0198 mmols) and diethylamine (0.62 ml) were added at room temperature, in which a degassed THF (1.3 ml) solution of 1,4-diethynylbenzene 55 (25.0 mg, 0.198 mmols) was dropped.

The reaction solution was agitated at room temperature for 12 hours, after which water was added to the reaction solution for quenching.

After extraction with ether from an aqueous phase and washing with a saturated saline solution, the resulting organic phase was dried over anhydrous magnesium sulfate.

After filtration, the crude product obtained by concentrating the resulting filtrate under reduced pressure was purified by silica gel column chromatography (hexane/ether=3/1) to obtain bis[silylated ethynyl(thienyl-enediyne)]benzene compound 56 at a yield of 89% (163 mg).

$^1$H NMR δ 7.41 (s, 4H), 7.10 (d, J=3.9 Hz, 2H), 7.03 (d, J=3.9 Hz, 2H), 2.57 (t, J=7.5 Hz, 4H), 2.54 (t, J=7.5 Hz, 4H), 1.78-1.58 (m, 8H), 1.20-1.10 (m, 42H), 1.02 (t, J=7.5 Hz, 12H).

$^{13}$C NMR: δ 132.29, 131.27, 131.04, 130.21, 129.55, 125.04, 124.58, 123.27, 98.92, 98.82, 97.21, 94.00, 91.53, 91.24, 37.13, 36.86, 21.88 (×2), 18.61, 13.67, 13.59, 11.28.

UV/Vis (CHCl$_3$): λ$_{abs}$ [nm]=395.

Example 24

Synthesis of bis[silylated ethynyl(phenyl-enediyne)]benzene compound 58

(wherein n-Pr represents an n-propyl group and i-Pr represents an i-propyl group).

Using trans-phenyliodo-enyne compound 57 and 1,4-diethynylbenzene 55, bis[silylated ethynyl(phenyl-enediyne)] benzene compound 58 was obtained at a yield of 65% in the same manner as in Example 23.

m.p.=73-80° C.

$^1$H NMR δ 7.50-7.30 (m, 12H), 2.60 (t, J=7.5 Hz, 8H), 1.82-1.62 (m, 8H), 1.20-1.10 (m, 42H), 1.03 (t, J=7.5 Hz, 12H).

$^{13}$C NMR δ 131.94, 131.26, 131.08, 129.97, 129.93, 123.41, 123.28, 123.21, 106.69, 98.57, 98.52, 92.81, 91.28, 91.13, 37.08 (×2), 21.89 (×2), 18.66, 13.73 (×2), 11.31.

IR (KBr) 2957, 2864, 2151, 1654, 1503, 1458, 1260, 1099, 1016, 881, 833, 759, 672 cm$^{-1}$.

UV/Vis (CHCl$_3$): λ$_{abs}$ [nm]=379.

Example 25

Synthesis of bis[silylated ethynyl(phenyl-enediyne)]-thiophene compound 60

[Chemical Formula 58]

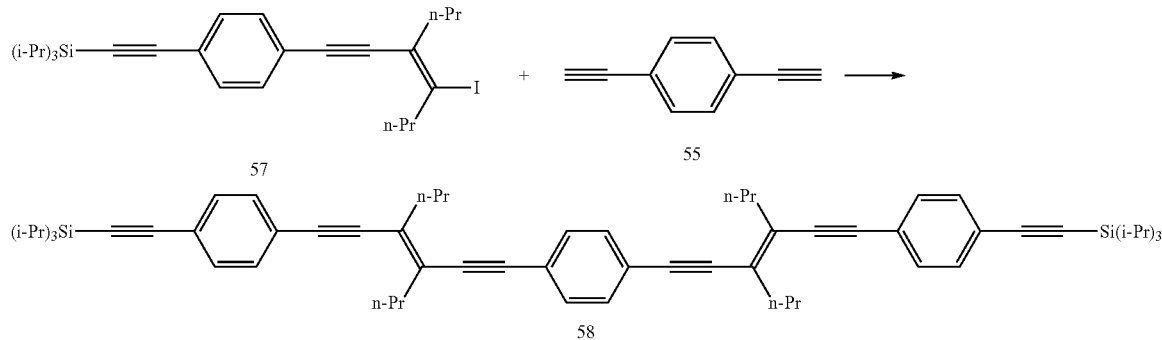

[Chemical Formula 59]

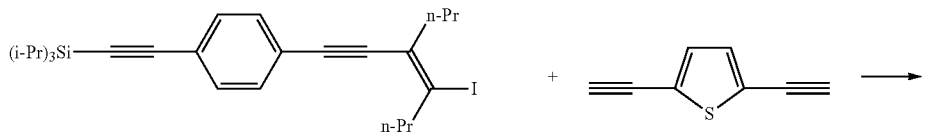

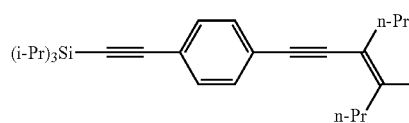 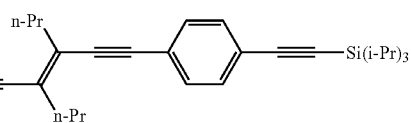

60

(wherein n-Pr represents an n-propyl group and i-Pr represents an i-propyl group).

Using trans-phenyliodo-enyne compound 57 and 2,5-diethynylthiophene 59, bis[silylated thienyl(phenyl-enediyne)]thiophene compound 60 was obtained at a yield of 30% in the same manner as in Example 23.

$^1$H NMR δ 7.45 (d, J=8.4 Hz, 4H), 7.38 (d, J=8.4 Hz, 4H), 7.08 (s, 2H), 2.58 (t, J=7.5 Hz, 4H), 2.55 (t, J=7.5 Hz, 4H), 1.80-1.62 (m, 8H), 1.20-1.10 (m, 42H), 1.024 (t, J=7.5 Hz, 6H), 1.019 (t, J=7.5 Hz, 6H).

$^{13}$C NMR: δ 132.05, 131.58, 131.19, 130.35, 129.60, 125.10, 123.43, 123.38, 106.75, 98.95, 94.67, 92.91, 91.55, 91.10, 37.09, 36.79, 21.79 (×2), 18.55, 13.57 (×2), 11.19.

IR (neat) 2959, 2153, 1600, 1501, 1461, 1381, 1227, 995, 883, 835, 800, 735, 675 cm$^{-1}$.

UV/Vis (CHCl$_3$): λ$_{abs}$ [nm]=401.

Using trans-phenyliodo-enyne compound 57 and 4-ethynyl phenyl ether 61, silylated ethynyl(phenyl-enediyne)phenyl ether compound 62 was obtained at a yield of 49% in the same manner as in Example 23.

m.p.=47-50° C.

$^1$H NMR δ 7.43 (d, J=8.7 Hz, 4H), 7.42 (d, J=8.7 Hz, 4H), 7.36 (d, J=8.7 Hz, 4H), 6.98 (d, J=8.7 Hz, 4H), 2.56 (t, J=7.5 Hz, 8H), 1.78-1.60 (m, 8H), 1.20-1.10 (m, 42H), 1.00 (t, J=7.2 Hz, 12H).

$^{13}$C NMR: δ 156.72, 133.04, 131.93, 131.06, 130.12, 129.24, 123.50, 123.14, 118.93, 118.58, 106.74, 98.19 (×2), 92.72, 91.19, 88.96, 37.13, 37.02, 21.88 (×2), 18.66, 13.72 (×2), 11.31.

IR (KBr) 2957, 2864, 2151, 1654, 1594, 1496, 1459, 1239, 1099, 1015, 878, 832, 673 cm$^{-1}$.

UV/Vis (CHCl$_3$): λ$_{abs}$ [nm]=351.

Example 26

Synthesis of Silylated Ethynyl(Phenyl-Enediyne)Phenyl Ether Compound 62

Example 27

Synthesis of bis[silylated ethynyl(phenyl-enediyne)]-bithiophene compound 64

[Chemical Formula 60]

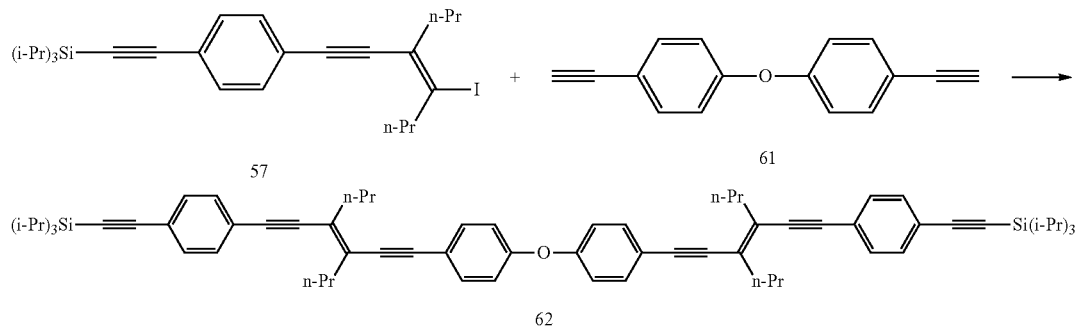

(wherein n-Pr represents an n-propyl group and i-Pr represents an i-propyl group).

[Chemical Formula 61]

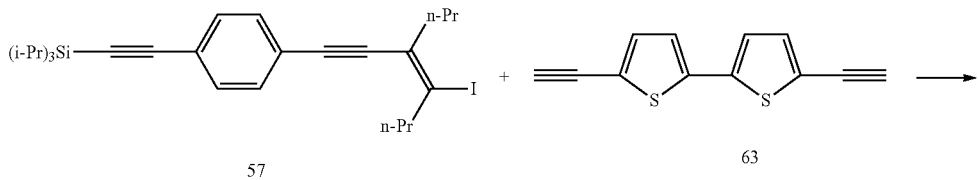

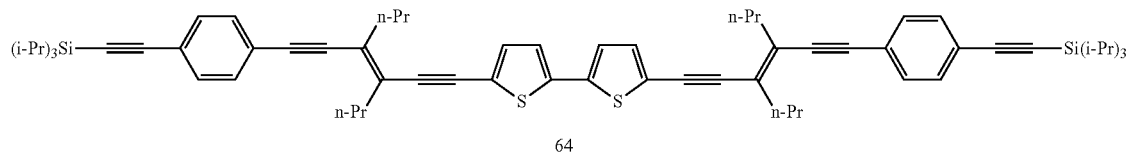

64

(wherein n-Pr represents an n-propyl group and i-Pr represents an i-propyl group).

Using trans-phenyliodo-enyne compound 57 and 5,5'-diethynyl-2,2'-bithiophene 63, bis[silylated ethynyl(phenyl-enediyne)bithiophene compound 64 was obtained at a yield of 58% in the same manner as in Example 23.

m.p.=60-63° C.

$^1$H NMR δ 7.44 (d, J=8.4 Hz, 4H), 7.38 (d, J=8.4 Hz, 4H), 7.10 (d, J=3.9 Hz, 2H), 7.07 (d, J=3.9 Hz, 2H), 2.57 (t, J=7.5 Hz, 4H), 2.55 (t, J=7.5 Hz, 4H), 1.78-1.60 (m, 8H), 1.20-1.10 (m, 42H), 1.02 (t, J=7.2 Hz, 12H).

$^{13}$C NMR: δ 138.32, 132.51, 132.05, 131.18, 130.03, 129.71, 124.13, 123.46, 123.35, 122.94, 106.75, 98.84, 95.00, 92.90, 91.78, 91.16, 37.07, 36.81, 21.80 (×2), 18.55, 13.58 (×2), 11.20.

IR (KBr) 2934, 2862, 2150, 1654, 1502, 1458, 1378, 1223, 994, 881, 833, 791, 759, 674 cm$^{-1}$.

UV/Vis (CHCl$_3$): λ$_{abs}$ [nm]=423.

Example 28

Synthesis of bis[silylated ethynyl(phenyl-enediyne)]-naphthalene compound 66

(wherein n-Pr represents an n-propyl group and i-Pr represents an i-propyl group).

Using trans-phenyliodo-enyne compound 57 and 2,6-diethynylnaphthalene 65, bis[silylated ethynyl(phenyl-enediyne)]naphthalene compound 66 was obtained at a yield of 60% in the same manner as in Example 23.

m.p.=42-46° C.

$^1$H NMR δ 7.93 (s, 2H), 7.76 (d, J=8.1 Hz, 2H), 7.52 (d, J=8.1 Hz, 2H), 7.45 (d, J=8.4 Hz, 4H), 7.39 (d, J=8.4 Hz, 4H), 2.74-2.52 (m, 8H), 1.85-1.65 (m, 8H), 1.20-1.10 (m, 42H), 1.05 (t, J=7.2 Hz, 6H), 1.04 (t, J=7.2 Hz, 6H).

$^{13}$C NMR: δ 132.45, 132.03, 131.17, 130.87, 130.17, 130.00, 129.12, 127.87, 123.56, 123.31, 121.78, 106.82, 99.20, 98.60, 92.81, 91.24, 90.52, 37.09, 37.06, 21.83 (×2), 18.55, 13.64 (×2), 11.21.

IR (KBr) 2957, 2863, 2151, 1654, 1595, 1500, 1458, 1377, 1261, 1098, 1017, 883, 807, 670 cm$^{-1}$.

UV/Vis (CHCl$_3$): λ$_{abs}$ [nm]=384.

[Chemical Formula 62]

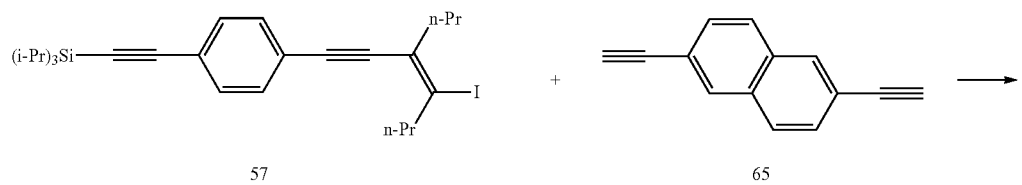

57    65

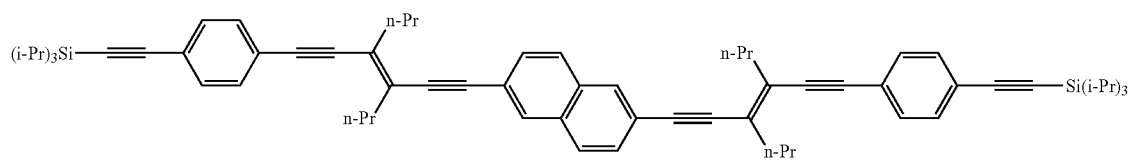

66

Example 29

Synthesis of bis[silylated ethynyl(phenyl-enediyne)]-anthracene compound 68

[Chemical Formula 63]

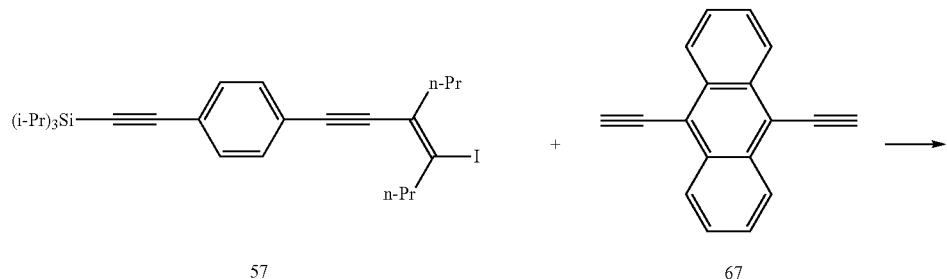

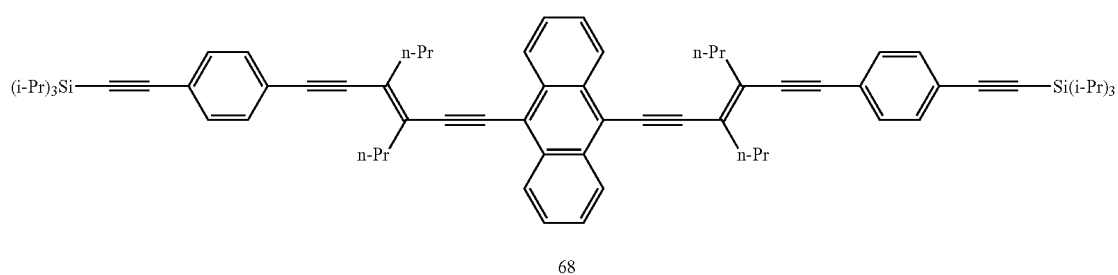

(wherein n-Pr represents an n-propyl group and i-Pr represents an i-propyl group).

Using trans-phenyliodo-enyne compound 57 and 9,10-diethynylanthracene 67, bis[silylated ethynyl(phenyl-enediyne)]anthracene compound 68 was obtained at a yield of 39% in the same manner as in Example 23.

m.p.=127-131° C.

$^1$H NMR δ 8.59 (dd, J=3.3, 6.6 Hz, 4H), 7.63 (dd, J=3.3, 6.6 Hz, 4H), 7.47 (d, J=8.4 Hz, 4H), 7.42 (d, J=8.4 Hz, 4H), 2.84 (t, J=7.5 Hz, 4H), 2.82 (t, J=7.5 Hz, 4H), 2.02-1.76 (m, 8H), 1.20-1.10 (m, 42H), 1.14 (t, J=6.6 Hz, 6H), 1.12 (t, J=7.2 Hz, 6H). $^{13}$C NMR: δ 131.99, 161.15, 130.30, 130.28, 127.15, 126.79 (×2), 123.43, 123.35, 118.82, 106.74, 102.79, 99.11, 96.31, 92.94, 91.46, 37.87, 37.59, 22.31, 22.23, 18.67, 13.94, 13.83, 11.34.

UV/Vis (CHCl$_3$): λ$_{abs}$ [nm]=345, 363, 483, 506.

Example 30

Synthesis of bis[silylated ethynyl(phenyl-enediyne)]-benzothiadiazole compound 70

[Chemical Formula 64]

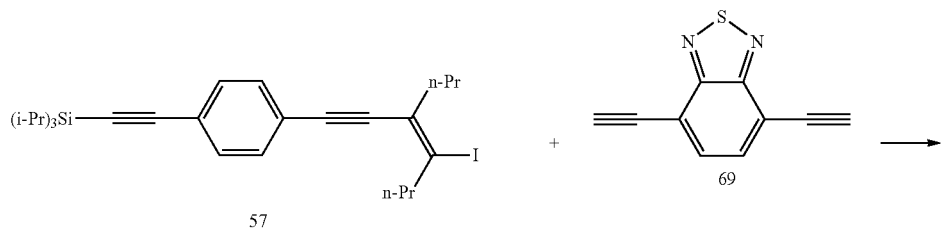

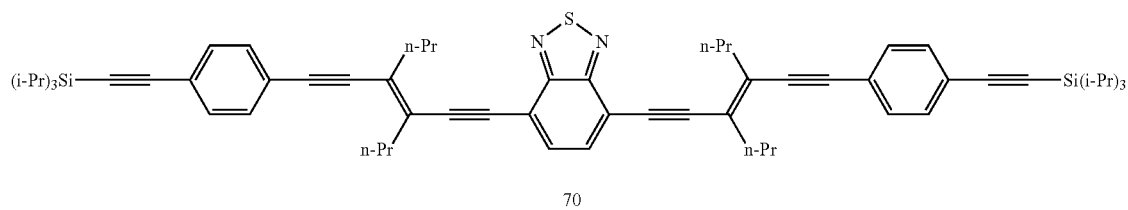

70

(wherein n-Pr represents an n-propyl group and i-Pr represents an i-propyl group).

Using trans-phenyliodo-enyne compound 57 and 4,7-diethynyl-2,1,3-benzothiadiazole 69, bis[silylated ethynyl (phenyl-enediyne)]benzothiadiazole compound 70 was obtained at a yield of 39% in the same manner as in Example 23.

m.p.=191-193° C.

$^1$H NMR δ 7.66 (s, 2H), 7.45 (d, J=8.4 Hz, 4H), 7.40 (d, J=8.4 Hz, 4H), 2.76 (t, J=7.2 Hz, 4H), 2.67 (t, J=7.2 Hz, 4H), 1.90-1.65 (m, 8H), 1.20-1.10 (m, 42H), 1.07 (t, J=7.5 Hz, 6H), 1.06 (t, J=7.2 Hz, 6H).

$^{13}$C NMR: δ 154.41, 131.96, 131.87, 131.65, 131.15, 129.64, 123.34, 123.27, 117.19, 106.65, 99.31, 97.71, 94.97, 92.92, 91.16, 37.29, 36.90, 22.05, 21.91, 18.65, 13.76 (×2), 11.28.

UV/Vis (CHCl$_3$): λ$_{abs}$ [nm]=351, 466.

Example 31

Synthesis of bis[silylated ethynyl(phenyl-enediyne)]-pyridazine compound 72

(wherein n-Pr represents an n-propyl group and i-Pr represents an i-propyl group).

Using trans-phenyliodo-enyne compound 57 and 3,6-diethynylpyrdazine 71, bis[silylated ethynyl(phenyl-enediyne)]pyridazine compound 72 was obtained at a yield of 60% in the same manner as in Example 23.

m.p.=130-135° C.

$^1$H NMR δ 7.47 (s, 2H), 7.44 (d, J=8.1 Hz, 4H), 7.38 (d, J=8.1 Hz, 4H), 2.68-2.52 (m, 8H), 1.80-1.62 (m, 8H), 1.20-1.10 (m, 42H), 1.01 (t, J=7.5 Hz, 12H).

$^{13}$NMR: δ 145.74, 133.52, 132.07, 131.29, 128.64, 128.49, 123.69, 123.11, 106.65, 99.92, 95.31, 94.98, 93.13, 90.55, 37.24, 36.69, 21.77 (×2), 18.52, 13.55, 13.50, 11.18.

IR (KBr) 2955, 2863, 2151, 1654, 1501, 1458, 1393, 1261, 1099, 1017, 880, 833, 806, 671 cm$^{-1}$.

UV/Vis (CHCl$_3$): λ$_{abs}$ [nm]=386.

[Chemical Formula 65]

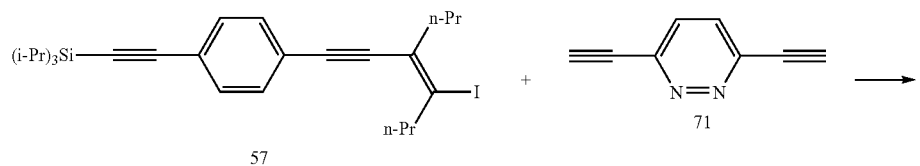

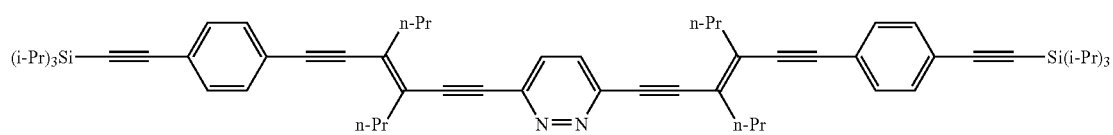

72

Example 32

Synthesis of tri[silylated ethynyl(phenyl-enediyne)]benzene compound 75

(a) Synthesis of 1,3,5-triethynylbenzene compound 74

[Chemical Formula 66]

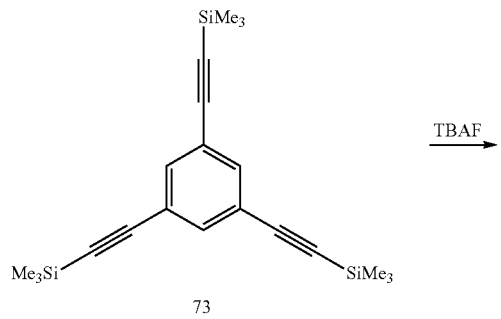

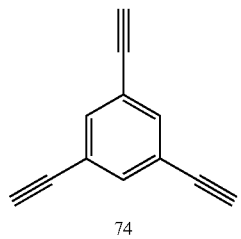

(wherein Me represents a methyl group).

1,3,5-Tris[(trimethylsilyl)ethynyl]benzene 73 (138 mg, 0.376 mmols) was dissolved in THF (3.8 ml), to which tetrabutylammonium fluoride (1.50 ml, 1.0 mmols/l in THF, 1.50 mmols) was added at 0° C. After agitation of the reaction solution at 0° C. for 1 hour, water was added to the reaction solution for quenching.

After extraction with ether from an aqueous phase and washing with a saturated saline solution, the resulting organic phase was dried over anhydrous magnesium sulfate.

After filtration, the crude product obtained by concentrating the resulting filtrate under reduced pressure was confirmed with NMR and used as it is for subsequent reaction.

(b) Synthesis of tri[silylated ethynyl(phenyl-enediyne)]benzene compound 75

[Chemical Formula 67]

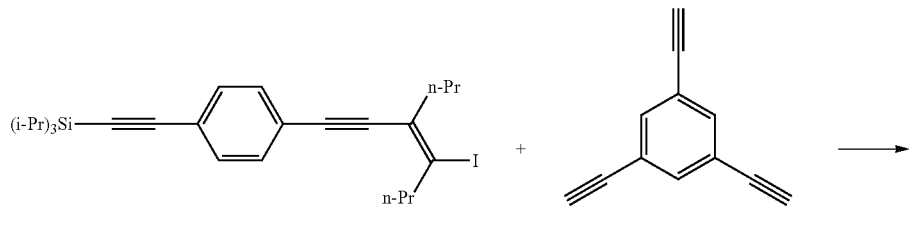

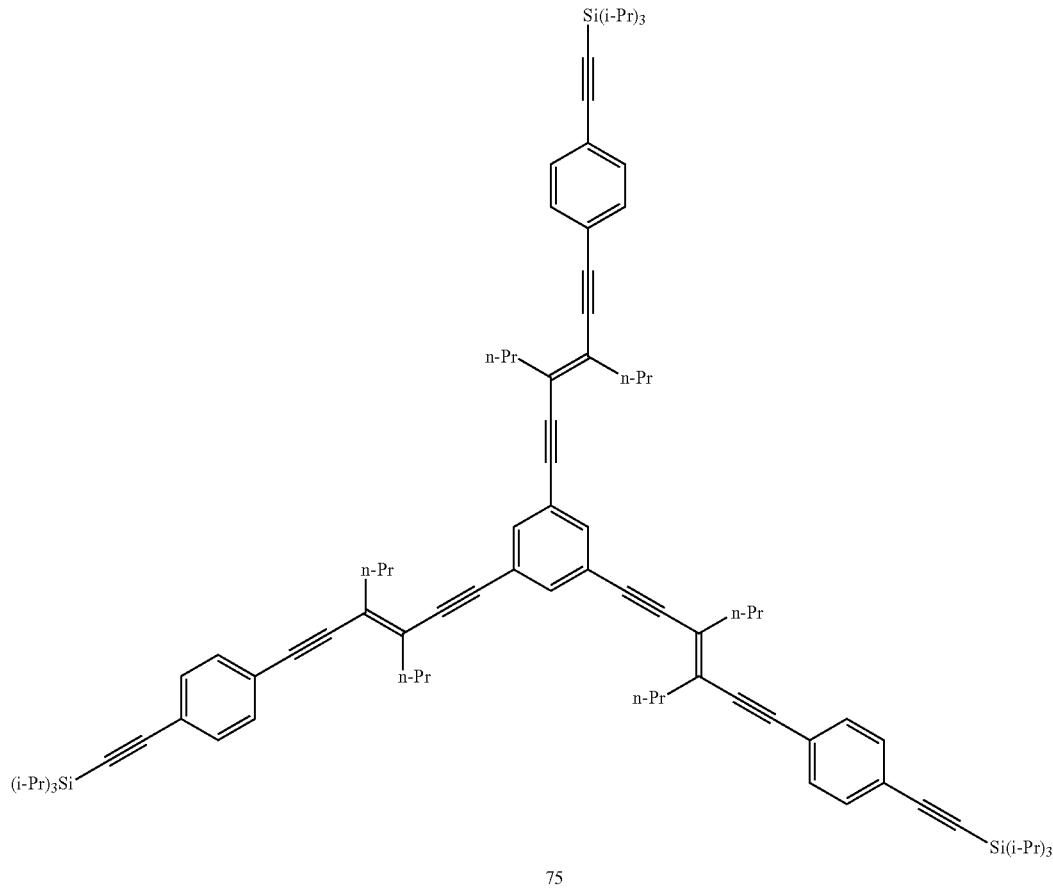

75

(wherein n-Pr represents an n-propyl group and i-Pr represents an i-propyl group).

Trans-phenyliodo-enyne compound 57 (780 mg, 1.50 mmols) was dissolved in degassed THF (2.4 ml), to which tetrakistriphenylphosphine palladium (21.7 mg, 0.0188 mmols), cuprous iodide (7.16 mg, 0.0376 mmols) and diethylamine (1.2 ml) were added at room temperature, followed by dropping a degassed THF (2.4 ml) solution of the terminal acetylene compound 74 obtained above.

The reaction solution was agitated at room temperature for 12 hours, to which water was subsequently added to the reaction solution for quenching. After extraction with ether from the aqueous phase and washing with a saturated saline solution, the resulting organic phase was dried over anhydrous magnesium sulfate.

After filtration, the crude product obtained by concentrating the resulting filtrate under reduced pressure was purified with silica gel column chromatography (hexane/ether=50/1) to obtain tri[silylated ethynyl(phenyl-enediyne)]benzene compound 75 at a yield of 71% (354 mg).

m.p.=87-91° C.

$^1$H NMR δ 7.431 (d, J=8.1 Hz, 6H), 7.427 (s, 3H), 7.37 (d, J=8.1 Hz, 6H), 2.57 (t, J=7.2 Hz, 12H), 1.80-1.60 (m, 12H), 1.20-1.10 (m, 63H), 1.02 (t, J=7.5 Hz, 9H), 1.01 (t, J=7.5 Hz, 9H).

$^{13}$C NMR: δ 133.42, 132.05, 131.20, 130.60, 129.70, 124.46, 123.46, 123.41, 106.78, 98.72, 97.07, 92.87, 90.99, 90.48, 37.08, 37.00, 21.80 (×2), 18.55, 13.58 (×2), 11.22.

IR (KBr) 2958, 2863, 2151, 1658, 1576, 1502, 1461, 1260, 1099, 1016, 879, 832, 674 cm$^{-1}$.

UV/Vis (CHCl$_3$): λ$_{abs}$ [nm]=352.

Example 33

Synthesis of tri[silylated ethynyl(phenyl-enediyne)phenyl]amine compound 77

[Chemical Formula 68]

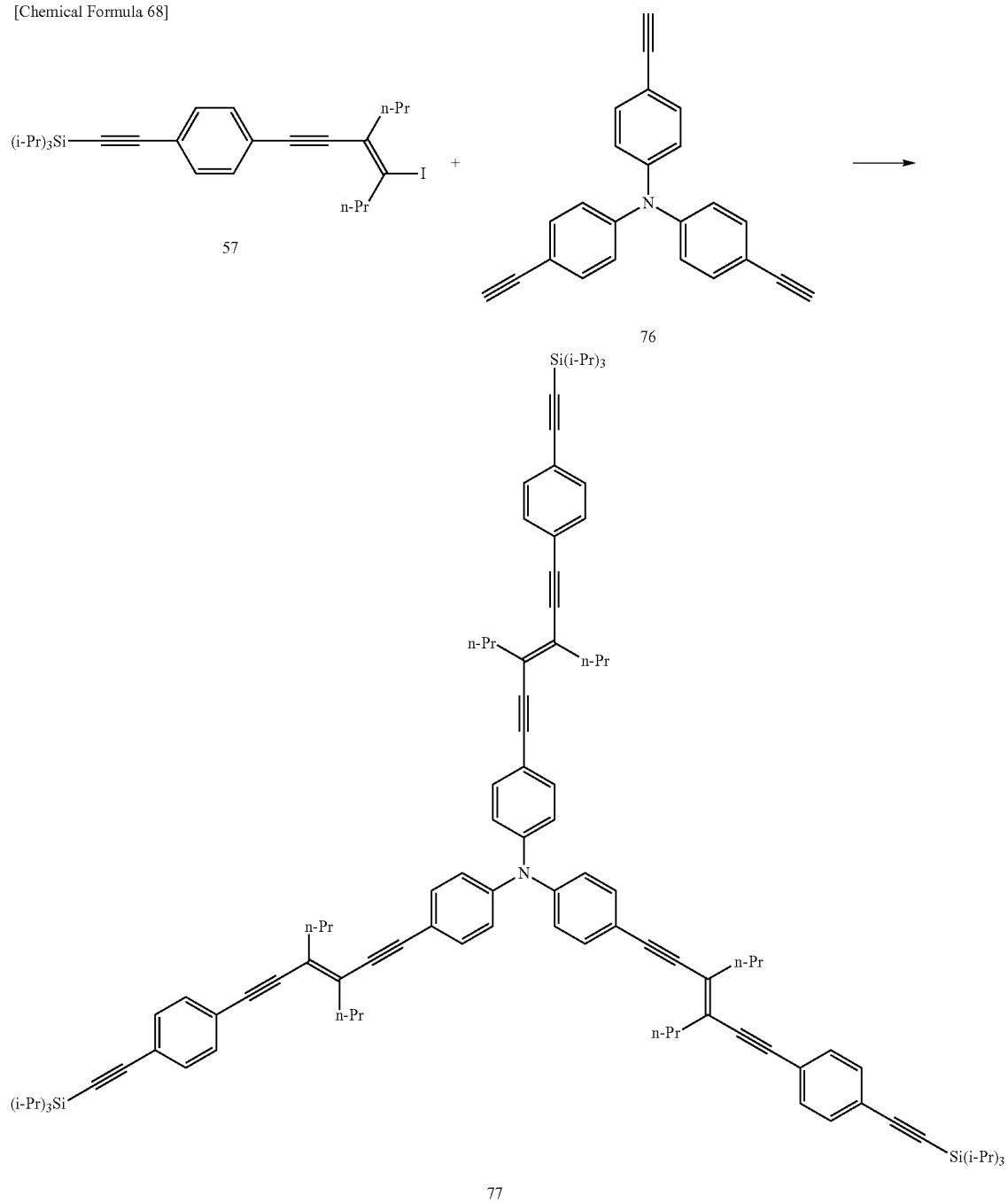

57

76

77

(wherein n-Pr represents an n-propyl group and i-Pr represents an i-propyl group).

Trans-phenyliodo-enyne compound 57 (510 mg, 0.984 mmols) was dissolved in degassed THF (1.6 ml), to which tetrakistriphenylphosphine palladium (14.2 mg, 0.0123 mmols), cuprous iodide (4.69 mg, 0.0246 mmols) and diethylamine (0.77 ml) were added at room temperature, followed by dropping a degassed THF (1.6 ml) solution of tri[(4-ethynyl)phenyl]amine 76 (78.0 mg, 0.250 mmols).

The reaction solution was agitated at room temperature for 12 hours, to which water was subsequently added to the reaction solution for quenching. After extraction with ether from the aqueous phase and washing with a saturated saline solution, the resulting organic phase was dried over anhydrous magnesium sulfate.

After filtration, the crude product obtained by concentrating the resulting filtrate under reduced pressure was purified with silica gel column chromatography (hexane/ether=10/1)

to obtain tri[silylated ethynyl(phenyl-enediyne)phenyl]amine compound 77 at a yield of 71% (264 mg).

m.p.=128-131° C.

$^1$H NMR δ 7.44 (d, J=8.1 Hz, 6H), 7.37 (d, J=8.1 Hz, 6H), 7.36 (d, J=8.4 Hz, 6H), 7.06 (d, J=8.4 Hz, 6H), 2.58 (t, J=7.2 Hz, 12H), 1.80-1.60 (m, 12H), 1.20-1.10 (m, 63H), 1.00 (t, J=7.2 Hz, 18H).

$^{13}$C NMR: δ 146.68, 132.65, 132.02, 131.14, 130.32, 129.19, 124.09, 123.62, 123.21, 118.36, 106.80, 98.76, 98.23, 92.77, 91.33, 89.36, 37.07, 36.96, 21.78 (×2), 18.55, 13.61, 13.58, 11.19.

IR (KBr) 2955, 2862, 2150, 1651, 1595, 1501, 1459, 1316, 1264, 1173, 1100, 1015, 881, 833, 674 cm$^{-1}$.

UV/Vis (CHCl$_3$): λ$_{abs}$ [nm]=339, 399.

Example 34

Synthesis of tri[[(anisylethynyl)phenyl-enediyne]phenyl]-amine compound 80

(a) Synthesis of tri[(phenyl-enediyne)phenyl]amine compound 78

(wherein n-Pr represents an n-propyl group and i-Pr represents an i-propyl group).

Tri[silylated ethynyl(phenyl-enediyne)phenyl]amine compound 77 (100 mg, 0.0671 mmols) was dissolved in THF (0.67 ml), to which tetrabutylammonium fluoride (0.269 mg, 1.0 mol/l in THF, 0.269 mmols) was added at 0° C.

The reaction solution was agitated at 0° C. for 1 hour, to which water was subsequently added to the reaction solution for quenching. After extraction with ether from the aqueous phase and washing with a saturated saline solution, the resulting organic phase was dried over anhydrous magnesium sulfate.

After filtration, the crude product obtained by concentrating the resulting filtrate under reduced pressure was confirmed with NMR and used as it is for subsequent reaction.

[Chemical Formula 69]

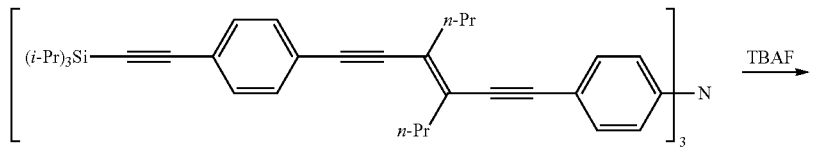

(b) Synthesis of tri[[(anisylethynyl)phenyl-enediyne]phenyl]-amine compound 80

[Chemical Formula 70]

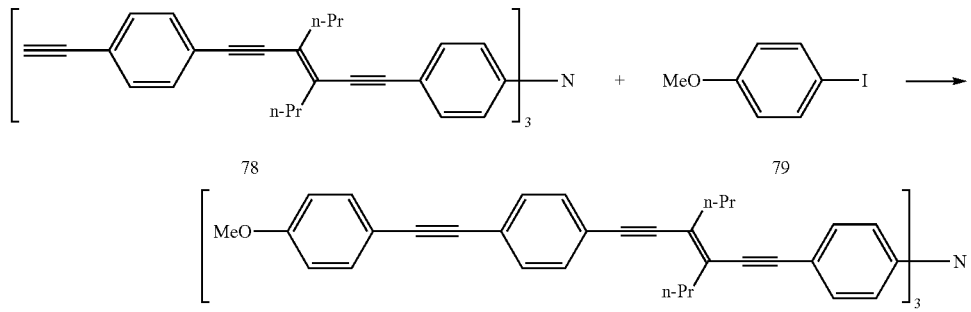

(wherein Me represents a methyl group and n-Pr represents an n-propyl group).

4-Iodoanisole 79 (62.8 mg, 0.268 mmols) was dissolved in degassed THF (0.84 ml), to which tetrakistriphenylphosphine palladium (3.88 mg, 0.00336 mmols), cuprous iodide (1.28 mg, 0.00671 mmols) and diethylamine (0.21 ml) were added at room temperature, followed by dropping a degassed THF (0.84 ml) solution of the terminal acetylene compound 78 obtained above.

The reaction solution was agitated at room temperature for 12 hours, to which water was subsequently added to the reaction solution for quenching.

After extraction with ether from the aqueous phase and washing with a saturated saline solution, the resulting organic phase was dried over anhydrous magnesium sulfate.

After filtration, the crude product obtained by concentrating the resulting filtrate under reduced pressure was purified with silica gel column chromatography (hexane/ether=5/1) to obtain tri[silylated (phenyl-endiyne)]amine compound 80 at a yield of 47% (42.6 mg).

$^1$H NMR δ 7.48 (d, J=8.7 Hz, 6H), 7.47 (d, J=8.7 Hz, 6H), 7.41 (d, J=8.7 Hz, 6H), 7.36 (d, J=8.4 Hz, 6H), 7.06 (d, J=8.4 Hz, 6H), 6.89 (d, J=8.7 Hz, 6H), 3.84 (s, 9H), 2.59 (t, J=7.2 Hz, 12H), 1.80-1.62 (m, 12H), 1.06-0.98 (m, 18H).

$^{13}$C NMR: δ 159.75, 146.52, 133.07, 132.54, 131.31, 131.20, 130.11, 129.13, 124.00, 123.25, 123.06, 118.33, 115.10, 114.03, 98.68, 98.31, 91.34, 91.18, 89.34, 87.96, 55.28, 37.12, 37.04, 21.88 (×2), 13.72 (×2).

UV/Vis (CHCl$_3$): $\lambda_{abs}$ [nm]=346, 401.

[2] Measurement of Fluorescent Spectra

In the following examples, fluorescent spectra were measured by use of F-4010 Fluorescence Spectrophotometer (made by Hitachi Ltd.).

Example 35

The compound 36 obtained in Example 13 was dissolved in chloroform (9.3×10$^{-6}$ M) and excited with light of 372 nm, whereupon red fluorescence was observed at 647 nm (FIG. 1).

Example 36

Figure 2:
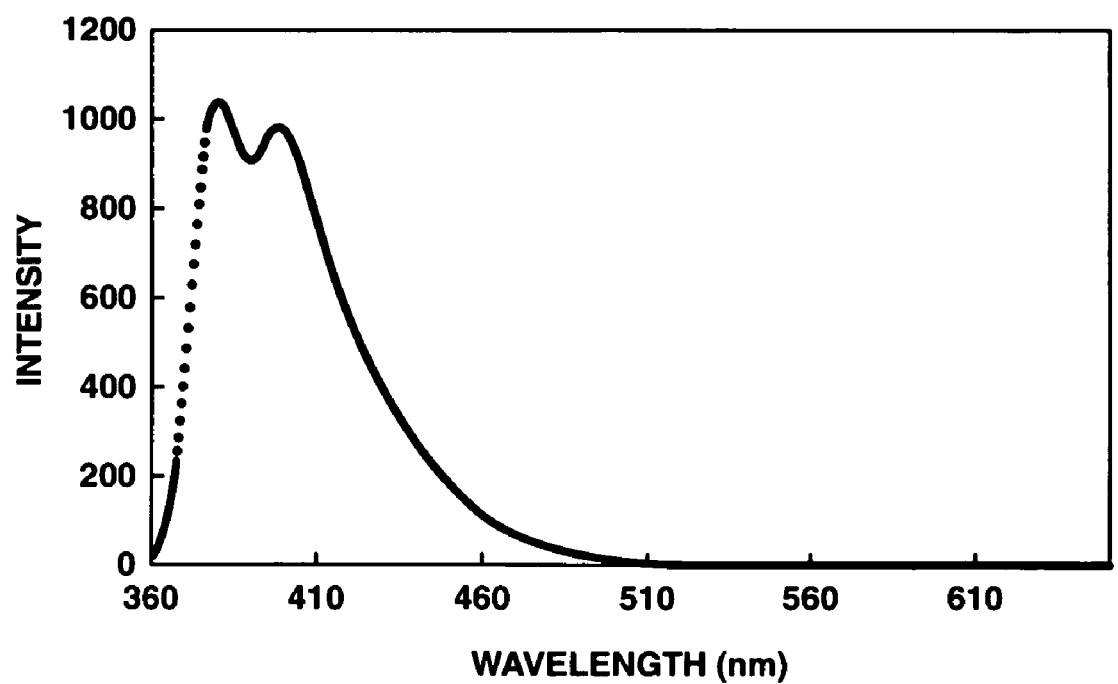
FIG. 2 is a fluorescent spectrum of compound 43.

The compound 43 obtained in Example 14 was dissolved in chloroform (1.6×10$^{-5}$ M) and excited with light of 347 nm, whereupon violet fluorescence was observed at 380 nm (FIG. 2).

Example 37

Figure 3:
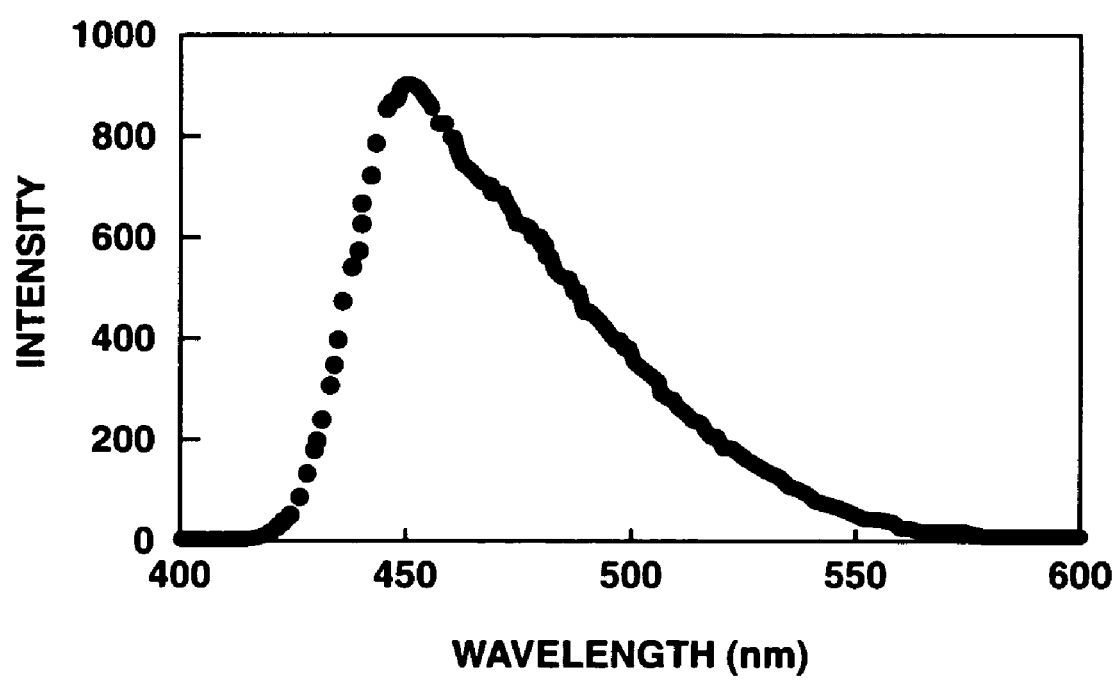
FIG. 3 is a fluorescent spectrum of compound 56.

The compound 56 obtained in Example 24 was dissolved in chloroform (1.0×10$^{-5}$ M) and excited with light of 395 nm, whereupon blue fluorescence was observed at 451 nm (FIG. 3).

Example 38

Figure 4:
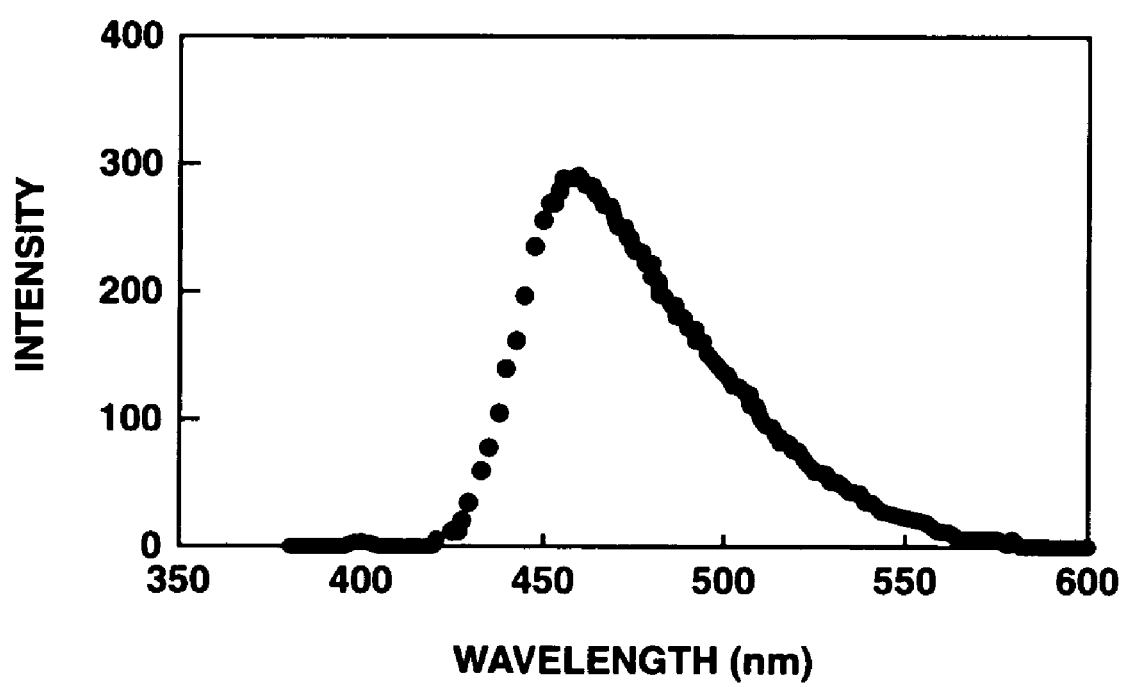
FIG. 4 is a fluorescent spectrum of compound 77.

The compound 77 obtained in Example 33 was dissolved in chloroform (1.0×10$^{-5}$ M) and excited with light of 399 nm, whereupon blue fluorescence was observed at 459 nm (FIG. 4).

Example 39

The compounds obtained in the respective examples were each dissolved in chloroform (about 10$^{-5}$ M) and excited with excitation light with an appropriate wavelength, whereupon fluorescence emission was observed in the respective cases.

The excitation light and fluorescence maximum (λmax) in the fluorescence spectra of each compound are shown in Table 1.

TABLE 1

| Example | Compound | Excitation (nm) | Fluorescence λmax (nm) |
|---|---|---|---|
| 1 | 8 | 385 | 434 |
| 3 | 10 | 407 | 477 |
| 5 | 12 | 427 | 494 |
| 6 | 19 | 359 | 405 |
| 8 | 21 | 386 | 436 |
| 10 | 23 | 394 | 447 |
| 11 | 25 | 375 | 479 |
| 12 | 30 | 473 | 569 |
| 13 | 36 | 541 | 647 |
| 14 | 43 | 345 | 380 |
| 16 | 45 | 376 | 432, 447 |
| 18 | 47 | 393 | 438 |
| 19 | 49 | 366 | 420 |
| 20 | 51 | 340 | 377, 396 |
| 22 | 54 | 363 | 399 |
| 24 | 56 | 395 | 451 |
| 25 | 58 | 379 | 431 |
| 26 | 60 | 401 | 463 |
| 27 | 62 | 351 | 398 |
| 28 | 64 | 423 | 493 |
| 29 | 66 | 384 | 431 |
| 30 | 68 | 483 | 536 |
| 31 | 70 | 466 | 552 |
| 32 | 72 | 386 | 448 |
| 33 | 75 | 352 | 394 |
| 34 | 77 | 399 | 459 |
| 35 | 80 | 401 | 463 |

The invention claimed is:

1. A π-conjugated aromatic ring-containing compound, characterized by being represented by the formula (1)

[Chemical Formula 1]

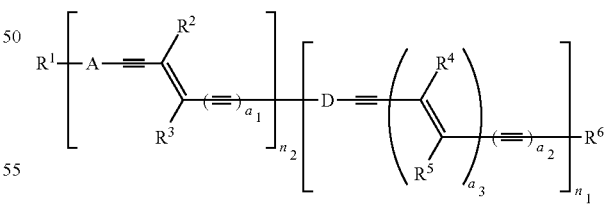

(1)

{wherein R$^1$ represents a hydrogen atom, a halogen atom, a cyano group, a nitro group, a dimethylamino group, a diphenylamino group, an alkoxy group having 1 to 3 carbon atoms, an alkyl group having 1 to 10 carbon atoms, a halogenated alkyl group that has 1 to 10 carbon atoms and may be optionally substituted with a fluorine atom or chlorine atom, or a group represented by the following formula (2) or a group represented by the following formula (3)

[Chemical Formula 2]

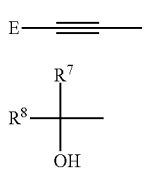

(2)

(3)

[wherein E represents a hydrogen atom, a substituted silyl group, a phenyl group, a naphthyl group, a pyridyl group, a pyrimidinyl group, a pyridazinyl group, a pyrazinyl group, a furanyl group, a pyrrolyl group, a pyrazolyl group, an imidazolyl group or a thienyl group (provided that said phenyl group, naphthyl group, pyridyl group, pyrimidinyl group, pyridazinyl group, pyrazinyl group, furanyl group, pyrrolyl group, pyrazolyl group, imidazolyl group or thienyl group may be optionally substituted with a halogen atom, a cyano group, a nitro group, a dimethylamino group, a diphenylamino group, an alkoxy group having 1 to 3 carbon atoms, an alkyl group having 1 to 10 carbon atoms, or a halogenated alkyl group that has 1 to 10 carbon atoms and may be optionally substituted with a fluorine or chlorine atom), $R^7$ and $R^8$ independently represent an alkyl group having 1 to 10 carbon atoms], $R^2$, $R^3$, $R^4$, and $R^5$ independently represent a hydrogen atom or an alkyl group having 1 to 10 carbon atoms, $R^6$ represents a hydrogen atom, a substituted silyl group, a phenyl group, a naphthyl group, a pyridyl group, a pyrimidinyl group, a pyridazinyl group, a pyrazinyl group, a furanyl group, a pyrrolyl group, a pyrazolyl group, an imidazolyl group, a thienyl group (provided that the phenyl group, naphthyl group, pyridyl group, pyrimidinyl group, pyridazinyl group, pyrazinyl group, furanyl group, pyrrolyl group, pyrazolyl group, imidazolyl group or thienyl group may be optionally substituted with a halogen atom, a cyano group, a nitro group, a dimethylamino group, a diphenylamino group, an alkoxy group having 1 to 3 carbon atoms, an alkyl group having 1 to 10 carbon atoms, or a halogenated alkyl group that has 1 to 10 carbon atoms and may be optionally substituted with a fluorine or chlorine atom), a group represented by the afore-indicated formula (2) or a group represented by the afore-indicated formula (3), A and D independently represent a naphthalene ring, an anthracene ring, a phenanthrene group, a phenarene ring, a fluorene ring, a triphenylene ring, a pyrene ring, a perylene ring, a pyrimidine ring, a pyridazine ring, a pyrazine ring, a furan ring, a pyrrole ring, a pyrazole ring, an imidazole ring, a benzothiadiazole ring, a thieno[3,4-b]pyrazine ring, a furo[3,4-b]pyrazine ring or a 6H-pyrrolo[3,4-b]pyrazine ring (provided that these rings may be optionally substituted with a phenyl group, a halogen atom, a cyano group, a nitro group, a dimethylamino group, a diphenylamino group, an alkoxy group having 1 to 3 carbon atoms, an alkyl group having 1 to 10 carbon atoms or a halogenated alkyl group that has 1 to 10 carbon atoms and may be optionally substituted with a fluorine atom or a chlorine atom), $a_1$, $a_2$, and $a_3$ are independently 0 or 1, and $n_1$ and $n_2$ are independently an integer of 1 to 5].

2. A π-conjugated aromatic ring-containing compound, characterized by being represented by the formula (4)

[Chemical Formula 3]

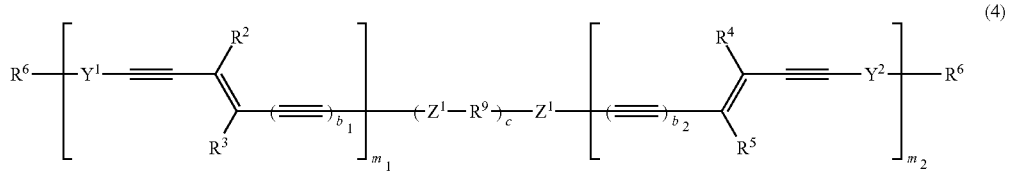

(4)

[wherein $R^2$, $R^3$, $R^4$, and $R^5$ independently represent a hydrogen atom or an alkyl group having 1 to 10 carbon atoms, $R^6$ represents a hydrogen atom, a substituted silyl group, a phenyl group, a naphthyl group, a pyridyl group, a pyrimidinyl group, a pyridazinyl group, a pyrazinyl group, a furanyl group, a pyrrolyl group, a pyrazolyl group, an imidazolyl group, a thienyl group (provided that the phenyl group, naphthyl group, pyridyl group, pyrimidinyl group, pyridazinyl group, pyrazinyl group, furanyl group, pyrrolyl group, pyrazolyl group, imidazolyl group or thienyl group may be optionally substituted with a halogen atom, a cyano group, a nitro group, a dimethylamino group, a diphenylamino group, an alkoxy group having 1 to 3 carbon atoms, an alkyl group having 1 to 10 carbon atoms, or a halogenated alkyl group that has 1 to 10 carbon atoms and may be optionally substituted with a fluorine or chlorine atom), a group represented by the formula (2) or a group represented by the formula (3),

[Chemical Formula 4]

(2)

(3)

[wherein E represents a hydrogen atom, a substituted silyl group, a phenyl group, a naphthyl group, a pyridyl group, a pyrimidinyl group, a pyridazinyl group, a pyrazinyl group, a furanyl group, a pyrrolyl group, a pyrazolyl group, an imidazolyl group or a thienyl group (provided that said phenyl group, naphthyl group, pyridyl group, pyrimidinyl group, pyridazinyl group, pyrazinyl group, furanyl group, pyrrolyl group, pyrazolyl group, imidazolyl group or thienyl group may be optionally substituted with a halogen atom, a cyano group, a nitro group, a dimethylamino group, a diphenylamino group, an alkoxy group having 1 to 3 carbon atoms, an alkyl group having 1 to 10 carbon atoms, or a halogenated alkyl group that has 1 to 10 carbon atoms and may be optionally substituted with a fluorine or chlorine atom), $R^7$ and $R^8$ independently represent an alkyl group having 1 to 10 carbon atoms], $Z^1$, $Y^1$, and $Y^2$ independently represent a paraphenylene group, a naphthalene ring, an anthracene ring, a phenanthrene group, a phenarene ring, a fluorene ring, a triphenylene ring, a pyrene ring, a perylene ring, a pyridine ring, a pyrimidine ring, a pyridazine ring, a pyrazine ring, a furan ring, a pyrrole ring, a pyrazole ring, an imidazole ring, a thiophene ring, a benzothiadiazole ring, a thieno[3,4-b]pyrazine ring, a furo[3,4-b]pyrazine ring or a 6H-pyrrolo[3,4-b]pyrazine ring (provided that these rings and groups may be optionally substituted with a phenyl group, a halogen atom, a cyano group, a nitro group, a dimethylamino group, a diphenylamino group, an alkoxy group having 1 to 3 carbon atoms, an alkyl group having 1 to 10 carbon atoms or a halogenated alkyl group that has 1 to 10 carbon atoms and may be optionally substituted with a fluorine atom or a chlorine atom), $R^9$ represents a single bond, —O—, —S—, —S(O)—, —S(O$_2$)—, —C(O)O—, —OC(O)—, —C(S)O—, —OC(S)—, —C(O)NH—, —NHC(O)—, —C(S)NH—, —NHC(S)—, —NH— or a divalent saturated or unsaturated hydrocarbon group that has 1 to 8 carbon atoms and may be branched, $b_1$ and $b_2$ are independently 0 or 1, c is an integer of 0 to 3, and $m_1$ and $m_2$ are independently an integer of 1 to 5].

3. A π-conjugated aromatic ring-containing compound, characterized by being represented by the formula (5)

[Chemical Formula 4]

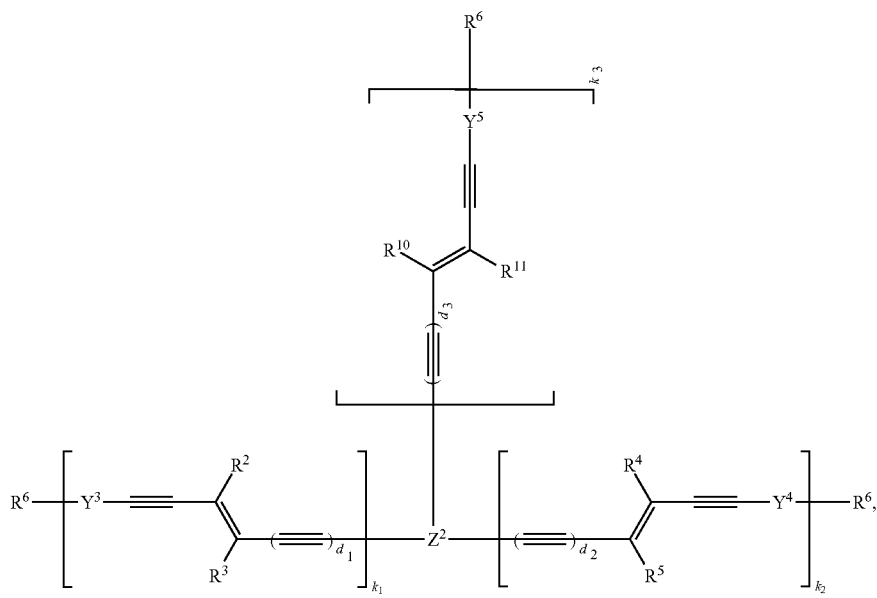

(5)

{wherein $R^2$, $R^3$, $R^4$, and $R^5$ independently represent a hydrogen atom or an alkyl group having 1 to 10 carbon atoms, $R^6$ represents a hydrogen atom, a substituted silyl group, a phenyl group, a naphthyl group, a pyridyl group, a pyrimidinyl group, a pyridazinyl group, a pyrazinyl group, a furanyl group, a pyrrolyl group, a pyrazolyl group, an imidazolyl group, a thienyl group (provided that the phenyl group, naphthyl group, pyridyl group, pyrimidinyl group, pyridazinyl group, pyrazinyl group, furanyl group, pyrrolyl group, pyrazolyl group, imidazolyl group or thienyl group may be optionally substituted with a halogen atom, a cyano group, a nitro group, a dimethylamino group, a diphenylamino group, an alkoxy group having 1 to 3 carbon atoms, an alkyl group having 1 to 10 carbon atoms, or a halogenated alkyl group that has 1 to 10 carbon atoms and may be optionally substituted with a fluorine or chlorine atom), a group represented by the formula (2) or a group represented by the formula (3),

[Chemical Formula 6]

 (2)

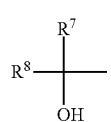 (3)

[wherein E represents a hydrogen atom, a substituted silyl group, a phenyl group, a naphthyl group, a pyridyl group, a pyrimidinyl group, a pyridazinyl group, a pyrazinyl group, a furanyl group, a pyrrolyl group, a pyrazolyl group, an imidazolyl group or a thienyl group (provided that said phenyl group, naphthyl group, pyridyl group, pyrimidinyl group, pyridazinyl group, pyrazinyl group, furanyl group, pyrrolyl group, pyrazolyl group, imidazolyl group or thienyl group may be optionally substituted with a halogen atom, a cyano group, a nitro group, a dimethylamino group, a diphenylamino group, an alkoxy group having 1 to 3 carbon atoms, an alkyl group having 1 to 10 carbon atoms, or a halogenated alkyl group that has 1 to 10 carbon atoms and may be optionally substituted with a fluorine or chlorine atom), $R^7$ and $R^8$ independently represent an alkyl group having 1 to 10 carbon atoms], $R^{10}$ and $R^{11}$ independently represent a hydrogen atom or an alkyl group having 1 to 10 carbon atoms, $Y^3$ to $Y^5$ independently represent a benzene ring, a naphthalene ring, an anthracene ring, a phenanthrene group, a phenarene ring, a fluorene ring, a triphenylene ring, a pyrene ring, a perylene ring, a pyridine ring, a pyrimidine ring, a pyridazine ring, a pyrazine ring, a furan ring, a pyrrole ring, a pyrazole ring, an imidazole ring, a thiophene ring, a benzothiadiazole ring, a thieno[3,4-b]pyrazine ring, a furo[3,4-b]pyrazine ring or a 6H-pyrrolo[3,4-b]pyrazine ring (provided that these rings may be optionally substituted with a phenyl group, a halogen atom, a cyano group, a nitro group, a dimethylamino group, a diphenylamino group, an alkoxy group having 1 to 3 carbon atoms, an alkyl group having 1 to 10 carbon atoms or a halogenated alkyl group that has 1 to 10 carbon atoms and may be optionally substituted with a fluorine atom or a chlorine atom), $Z^2$ represents a trivalent aryl group, a group represented by the following formula (6) or a group represented by the following formula (7)

[Chemical Formula 9]

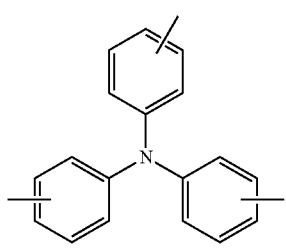

(6)

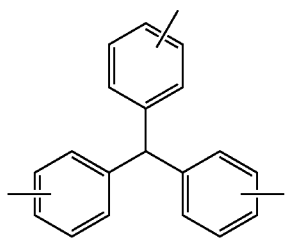

(7)

$d_1$ to $d_3$ are independently 0 or 1, and $k_1$ to $k_3$ are independently an integer of 1 to 5}.

4. A π-conjugated aromatic ring-containing compound, characterized by being represented by the formula (12)

[Chemical Formula 11]

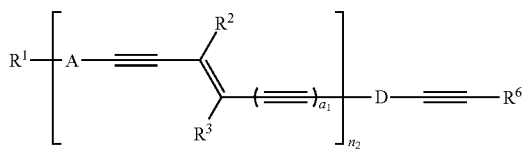

(12)

{wherein $R^1$ represents a hydrogen atom, a halogen atom, a cyano group, a nitro group, a dimethylamino group, a diphenylamino group, an alkoxy group having 1 to 3 carbon atoms, an alkyl group having 1 to 10 atoms, a halogenated alkyl group that has 1 to 10 carbon atoms and may be optionally substituted with a fluorine atom or chlorine atom, or a group represented by the following formula (2)

[Chemical Formula 12]

$$E\equiv \qquad (2)$$

[wherein E represents a hydrogen atom, a substituted silyl group, a phenyl group, a naphthyl group, a pyridyl group, a pyrimidinyl group, a pyridazinyl group, a pyrazinyl group, a furanyl group, a pyrrolyl group, a pyrazolyl group, an imidazolyl group or a thienyl group (provided that said phenyl group, naphthyl group, pyridyl group, pyrimidinyl group, pyridazinyl group, pyrazinyl group, furanyl group, pyrrolyl group, pyrazolyl group, imidazolyl group or thienyl group may be optionally substituted with a halogen atom, a cyano group, a nitro group, a dimethylamino group, a diphenylamino group, an alkoxy group having 1 to 3 carbon atoms, an alkyl group having 1 to 10 atoms, a halogenated alkyl group that has 1 to 10 carbon atoms and may be optionally substituted with a fluorine atom or chlorine atom)], $R^2$ and $R^3$ independently represent a hydrogen atom or an alkyl group having 1 to 10 carbon atoms, $R^6$ represents a hydrogen atom, a substituted silyl group, a phenyl group, a naphthyl group, a pyridyl group, a pyrimidinyl group, a pyridazinyl group, a pyrazinyl group, a furanyl group, a pyrrolyl group, a pyrazolyl group, an imidazolyl group or a thienyl group (provided that said phenyl group, naphthyl group, pyridyl group, pyrimidinyl group, pyridazinyl group, pyrazinyl group, furanyl group, pyrrolyl group, pyrazolyl group, imidazolyl group or thienyl group may be optionally substituted with a halogen atom, a cyano group, a nitro group, a dimethylamino group, a diphenylamino group, an alkoxy group having 1 to 3 carbon atoms, an alkyl group having 1 to 10 atoms, a halogenated alkyl group that has 1 to 10 carbon atoms and may be optionally substituted with a fluorine atom or chlorine atom), or a group represented by the following formula (3),

[Chemical Formula 13]

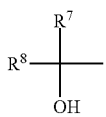

(3)

(wherein $R^7$ and $R^8$ independently represent an alkyl group having 1 to 10 carbons atoms), A and D independently represent a pyridine ring or a thiophene ring (provided that these rings may be optionally substituted with a phenyl group, a halogen atom, a cyano group, a nitro group, a dimethylamino group, a diphenylamino group, an alkoxy group having 1 to 3 carbon atoms, an alkyl group having 1 to 10 carbon atoms or a halogenated alkyl group that has 1 to 10 carbon atoms and may be optionally substituted with a fluorine atom or a chlorine atom), $a_1$ is independently 0 or 1, and $n_2$ is independently an integer or 1 to 5}.

5. The π-conjugated aromatic ring-containing compound according to claim 1, characterized in that said $R^1$ is a hydrogen atom, a cyano group, a nitro group, a dimethylamino group, a diphenylamino group, a methoxy group, a propoxy group, a methyl group, a trifluoromethyl group, a group represented by the following formula (8) or a group represented by the following formula (9)

[Chemical Formula 8]

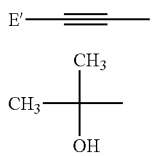

(8)

(9)

[wherein E' represents a hydrogen atom, a trimethylsilyl group, a tri-1-propylsilyl group, a phenyl group, a pyridyl group, a thienyl group (provided that the phenyl group, pyrdyl group or thienyl group may be optionally substituted with a cyano group, a nitro group, a dimethylamino group, a diphenylamino group, a methoxy group, an n-propoxy group, a methyl group or a trifluoromethyl group)].

6. The π-conjugated aromatic ring-containing compound according to any one of claims 1 to 5, characterized in that said $R^2$, $R^3$, $R^4$, and $R^5$ independently represent a hydrogen atom, a methyl group, an ethyl group or an n-propyl group.

7. The π-conjugated aromatic ring-containing compound according to claim 1, characterized in that said $R^6$ is a hydrogen atom, a trimethylsilyl group, a tri-i-propylsilyl group, a phenyl group, a pyridyl group, a thienyl group (provided that said phenyl group, pyridyl group or thienyl group may be optionally substituted with a cyano group, a nitro group, a dimethylamino group, a diphenylamino group, a methoxy group, an n-propoxy group, a methyl group or a trifluoromethyl group), a group represented by the following formula (8) or a group represented by the following formula (9),

[Chemical Formula 9]

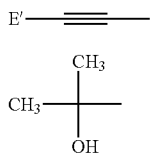

(8)

(9)

[wherein E' represents a hydrogen atom, a trimethylsilyl group, a tri-i-propylsilyl group, a phenyl group, a pyridyl group, a thienyl group (provided that the phenyl group, pyrdyl group or thienyl group may be optionally substituted with a cyano group, a nitro group, a dimethylamino group, a diphenylamino group, a methoxy group, an n-propoxy group, a methyl group or a trifluoromethyl group)].

8. The π-conjugated aromatic ring-containing compound according to claim 1, characterized in that said A and D independently represent a pyrimidine ring, a pyridazine ring, a pyrazine ring, a furan ring, a pyrrole ring, a pyrazole ring, an imidazole ring, a benzothiadiazole ring, a thieno[3,4-b]pyrazine ring, a furo[3,4-b]pyrazine ring or a 6H-pyrrolo[3,4-b]pyrazine ring (provided that these rings may be optionally substituted with a phenyl group, a halogen atom, a cyano group, a nitro group, a dimethylamino group, a diphenylamino group, an alkoxy group having 1 to 3 carbon atoms, an alkyl group having 1 to 10 carbon atoms or a halogenated alkyl group that has 1 to 10 carbon atoms and may be optionally substituted with a fluorine atom or a chlorine atom).

9. The π-conjugated aromatic ring-containing compound according to claim 8, characterized in that said A and D independently represent a pyridazine ring, a benzothiadiazole ring or a thieno[3,4-b]pyrazine ring (provided that these rings may be optionally substituted with a phenyl group, a cyano group, a methoxy group, an n-propoxy group, a methyl group or a trifluoromethyl group).

10. An organic electroluminescent device which comprises an anode and a cathode, and an organic thin film layer interposed there between, characterized in that said organic thin film layer is a layer constituted to contain the π-conjugated aromatic ring-containing compound defined in claim 1.

11. The π-conjugated aromatic ring-containing compound according to claim 2, characterized in that said $Z^1$, $Y^1$, and $Y^2$ independently represent a paraphenylene ring, a naphthalene ring, an anthracene ring, a pyridine ring, a pyridazine ring, a thiophene ring, a pyrrole ring, a benzothiadiazole ring or a thieno[3,4-b]pyrazine ring (provided that these rings may be optionally substituted with a phenyl group, a cyano group, a methoxy group, an n-propoxy group, a methyl group or a trifluoromethyl group), and $R^9$ represents a single bond or —O—, $b_1$ and $b_2$ are both 1, and c is 0 or 1.

12. The π-conjugated aromatic ring-containing compound of claim 2, wherein $Z^1$, $Y^1$ and $Y^2$ independently represent a naphthalene ring, an anthracene ring, a phenanthrene group, a phenarene ring, a fluorene ring, a triphenylene ring, a pyrene ring, a perylene ring, a pyridine ring, a pyrimidine ring, a pyridazine ring, a pyrazine ring, a furan ring, a pyrrole ring, a pyrazole ring, an imidazole ring, a thiophene ring, a benzothiadiazole ring, a thieno[3,4-b]pyrazine ring, a furo[3,4-b]pyrazine ring or a 6H-pyrrolo[3,4-b]pyrazine ring (provided that these rings may be optionally substituted with a phenyl group, a halogen atom, a cyano group, a nitro group, a dimethylamino group, a diphenylamino group, an alkoxy group having 1 to 3 carbon atoms, an alkyl group having 1 to 10 carbon atoms or a halogenated alkyl group that has 1 to 10 carbon atoms and may be optionally substituted with a fluorine atom or a chlorine atom).

13. The π-conjugated aromatic ring-containing compound according to claim 3, characterized in that said $Y^3$ to $Y^5$ independently represent a phenylene ring, a naphthalene ring, an anthracene ring, a pyridine ring, a pyridazine ring, a thiophene ring, a pyrrole ring, a benzothiadiazole ring or a thieno[3,4-b]pyrazine ring (provided that these rings may be optionally substituted with a phenyl group, a cyano group, a methoxy group, an n-propoxy group, a methyl group or a trifluoromethyl group), $Z^2$ is a group represented by the following formula (10) or a group represented by the following formula (11), and $d_1$ to $d_3$ are all 1.

[Chemical Formula 10]

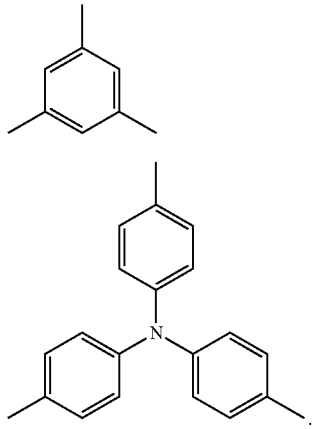

(10)

(11)

14. The π-conjugated aromatic ring-containing compound of claim 4, wherein $R^1$ represents a hydrogen atom, an alkyl group having 1 to 10 carbon atoms or a group represented by the following formula (2)

[Chemical Formula 14] (2)

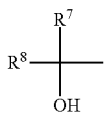

(2)

[wherein E represents a hydrogen atom, a substituted silyl group, a thienyl group (provided that said thienyl group may be optionally substituted with a cyano group)], $R^6$ represents a hydrogen atom, a substituted silyl group, pyridyl group (provided that said pyridyl group may be optionally substituted with a cyano group or an alkoxy group having 1 to 3 carbon atoms), or a group represented by the following formula (3),

[Chemical Formula 13]

$$R^8-\underset{OH}{\overset{R^7}{\underset{|}{C}}}-\quad\quad(3)$$

(wherein $R^7$ and $R^8$ represent an alkyl group having 1 to 10 carbon atoms).

15. The π-conjugated aromatic ring-containing compound of claim 14, wherein $R^7$ and $R^8$ represent a methyl group.

\* \* \* \* \*